(12) United States Patent
Gazit et al.

(10) Patent No.: US 9,096,645 B2
(45) Date of Patent: Aug. 4, 2015

(54) DIPEPTIDE ANALOGS FOR TREATING CONDITIONS ASSOCIATED WITH AMYLOID FIBRIL FORMATION

(75) Inventors: Ehud Gazit, Ramat-HaSharon (IL); Yaniv Amir, Yahud (IL); Ludmila Buzhansky, Ariel (IL); Ulrich Abel, Bad Homburg (DE); Anat Frydman-Marom, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 13/884,989

(22) PCT Filed: Nov. 15, 2011

(86) PCT No.: PCT/IL2011/050010
§ 371 (c)(1),
(2), (4) Date: May 13, 2013

(87) PCT Pub. No.: WO2012/066549
PCT Pub. Date: May 24, 2012

(65) Prior Publication Data
US 2013/0225512 A1   Aug. 29, 2013

Related U.S. Application Data

(60) Provisional application No. 61/413,488, filed on Nov. 15, 2010.

(30) Foreign Application Priority Data

Nov. 15, 2010 (EP) .................................... 10191253

(51) Int. Cl.
*A61K 38/05* (2006.01)
*C07D 209/20* (2006.01)
*C07K 5/078* (2006.01)

(52) U.S. Cl.
CPC .................. *C07K 5/06156* (2013.01)

(58) Field of Classification Search
CPC .................................................. C07K 5/06156
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,626,540 A | 12/1986 | Capps et al. |
| 4,666,828 A | 5/1987 | Gusella |
| 4,683,202 A | 7/1987 | Mullis |
| 4,801,531 A | 1/1989 | Frossard |
| 4,873,316 A | 10/1989 | Meade et al. |
| 4,879,219 A | 11/1989 | Wands et al. |
| 4,970,233 A | 11/1990 | McHugh |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,556,744 A | 9/1996 | Weiner et al. |
| 5,593,937 A | 1/1997 | Saito et al. |
| 5,593,967 A * | 1/1997 | Horwell et al. ................. 514/4.8 |
| 5,659,041 A | 8/1997 | Pollak et al. |
| 5,688,561 A | 11/1997 | Ichikawa et al. |
| 6,261,569 B1 | 7/2001 | Comis et al. |
| 6,303,567 B1 | 10/2001 | Findeis et al. |
| 6,359,112 B2 | 3/2002 | Kapurniotu et al. |
| 6,593,339 B1 | 7/2003 | Eek et al. |
| 6,610,478 B1 | 8/2003 | Takle et al. |
| 6,617,114 B1 | 9/2003 | Fowlkes et al. |
| 6,677,153 B2 | 1/2004 | Iversen |
| 6,689,753 B1 | 2/2004 | Soto-Jara |
| 7,732,479 B2 | 6/2010 | Gazit et al. |

(Continued)

FOREIGN PATENT DOCUMENTS

| AU | 2003207973 | 9/2003 |
|---|---|---|
| AU | 2004203461 | 11/2004 |

(Continued)

OTHER PUBLICATIONS

Trivedi et al "Second Generation 'Peptoid' CCK-B Receptor Antagonists: Identification and Development of N-(Adamantyloxycarbonyl)-alpha-methyl-(R)-tryptophan derivative (CI-1015) with and Improved Pharmacokinetic Profile" J Med Chem 41:38-45. Published 1998.*

Trivedi et al "Second Generatin 'Peptoid' CCK-B Receptor Antagonists: Identification and Development of N-(Adamantyloxycarbonyl)-a-methyl-(R)-tryptophan Derivative (CI-1015) with an Improved Pharmacokinetic Profile" J Med Chem 41:38-45. Published online Jan. 1, 1998.*

Requisition by the Examiner Dated Jun. 25, 2013 From the Canadian Intellectual Property Office Re. Application No. 2,530,927.

(Continued)

*Primary Examiner* — James H Alstrum Acevedo
*Assistant Examiner* — Zachary J Miknis

(57) ABSTRACT

Dipeptide analogs comprising a tryptophan (Trp) moiety coupled to a beta-sheet breaker moiety derived from alpha-aminoisobutyric acid (Aib) are disclosed. The dipeptide analogs exhibit an improved performance in inhibiting amyloid fibril formation, as compared to previously described dipeptides. Compositions containing the dipeptide analogs and uses thereof in treating amyloid-associated diseases and disorders are also disclosed.

9 Claims, 10 Drawing Sheets

(56) References Cited

U.S. PATENT DOCUMENTS

| | | | |
|---|---|---|---|
| 7,781,396 B2* | 8/2010 | Gazit | 514/17.8 |
| 8,012,929 B2 | 9/2011 | Gazit | |
| 2001/0007015 A1 | 7/2001 | Kapurniotu et al. | |
| 2001/0012889 A1 | 8/2001 | LaFleur et al. | |
| 2002/0035061 A1 | 3/2002 | Krieger et al. | |
| 2003/0130484 A1 | 7/2003 | Gordon et al. | |
| 2003/0225155 A1 | 12/2003 | Fernandez-Pol et al. | |
| 2004/0052928 A1 | 3/2004 | Gazit | |
| 2005/0020809 A1 | 1/2005 | Gazit | |
| 2006/0234947 A1 | 10/2006 | Gazit | |
| 2007/0021345 A1 | 1/2007 | Gazit | |
| 2007/0135334 A1 | 6/2007 | Gazit | |
| 2007/0138007 A1 | 6/2007 | Yemini et al. | |
| 2009/0156471 A1 | 6/2009 | Gazit et al. | |
| 2009/0209041 A1 | 8/2009 | Gazit | |
| 2010/0022459 A1 | 1/2010 | Gazit | |
| 2013/0338076 A1 | 12/2013 | Gazit | |

FOREIGN PATENT DOCUMENTS

| | | |
|---|---|---|
| DE | 3412445 | 10/1985 |
| DE | 10043282 | 3/2002 |
| EP | 0081122 | 6/1983 |
| EP | 0264166 | 4/1988 |
| EP | 0421946 | 4/1991 |
| EP | 0885904 | 12/1998 |
| FR | 1373316 | 9/1964 |
| IL | 210418 | 10/2012 |
| JP | 59-044313 | 3/1984 |
| JP | 60-040061 | 3/1985 |
| JP | 63-044895 | 2/1988 |
| JP | 02-295923 | 12/1990 |
| JP | 11-514333 | 12/1999 |
| JP | 2000-193661 | 7/2000 |
| JP | 2001-500852 | 1/2001 |
| JP | 2001-504334 | 4/2001 |
| JP | 2007-537699 | 12/2007 |
| WO | WO 80/00789 | 1/1980 |
| WO | WO 92/19253 | 11/1992 |
| WO | WO 95/08999 | 4/1995 |
| WO | WO 96/28471 | 9/1996 |
| WO | WO 96/39834 | 12/1996 |
| WO | WO 97/16191 | 5/1997 |
| WO | WO 98/08868 | 3/1998 |
| WO | WO 98/20135 | 5/1998 |
| WO | WO 99/27944 | 6/1999 |
| WO | WO 01/10457 | 2/2001 |
| WO | WO 01/21188 | 3/2001 |
| WO | WO 01/34631 | 5/2001 |
| WO | WO 01/45726 | 6/2001 |
| WO | WO 01/93836 | 12/2001 |
| WO | WO 03/063760 | 8/2003 |
| WO | WO 03/077866 | 9/2003 |
| WO | WO 03/077869 | 9/2003 |
| WO | WO 2005/000193 | 1/2005 |
| WO | WO 2006/006172 | 1/2006 |
| WO | WO 2007/043046 | 4/2007 |
| WO | WO 2009/000634 | 12/2008 |
| WO | WO 2009/095265 | 8/2009 |
| WO | WO 2012/066549 | 5/2012 |

OTHER PUBLICATIONS

Schoetz et al. "Determination of the Cis-Trans Isomerization Barrier of Several L-Peptidyl-L-Proline Dipeptides by Dynamic Capillary Electrophoresis and Computer Simulation", Electrophoresis, 22(12): 2409-2415, Aug. 1, 2001.

Summons to Attend Oral Proceedings Pursuant to Rule 115(1) EPC Dated Jul. 23, 2013 From the European Patent Office Re. Application No. 04744917.8.

Restriction Official Action Dated Oct. 29, 2013 From the US Patent and Trademark Office Re. U.S. Appl. No. 13/975,414.

Notice of Allowance Dated Jul. 8, 2013 From the US Patent and Trademark Office Re. U.S. Appl. No. 12/385,471.

Communication Pursuant to Article 94(3) EPC Dated Apr. 14, 2010 From the European Patent Office Re.: Application No. 03704977.2.
Communication Pursuant to Article 94(3) EPC Dated Nov. 18, 2011 From the European Patent Office Re.: Application No. 04744917.8.
European Search Report and the European Search Opinion Dated Mar. 16, 2011 From the European Patent Office Re. Application No. 10191253.3.
Examination Report Dated Jan. 8, 2008 From the Government of India, Patent Office Re.: Application No. 1671/CHENP/2004.
Examination Report Dated Jan. 12, 2011 From the Government of India, Patent Office Re. Application No. 380/CHENP/2006.
Examination Report Dated Jun. 19, 2007 of the Government of India, Patent Office Re.: Application No. 1671/CHENP/2004.
Examiner's Report Dated Apr. 7, 2011 From the Australian Government, IP Australia Re. Application No. 2004251522.
Examiner's Report Dated Feb. 11, 2010 From the Australian Government, IP Australia Re.: Application No. 2004251522.
Examiner's Report Dated Jun. 22, 2009 From the Australian Government, IP Australia Re.: Application No. 2004203461.
International Preliminary Report on Patentability Dated Jan. 22, 2009 From the International Bureau of WIPO Re.: Application No. PCT/IL2004/000577.
International Preliminary Report on Patentability Dated Jan. 25, 2007 From the International Bureau of WIPO Re.: Application No. PCT/IL2005/000754.
International Search Report and the Written Opinion Dated Mar. 28, 2006 From the International Searching Authority Re.: Application No. PCT/IL2005/000754.
International Search Report and the Written Opinion Dated Jan. 31, 2012 From the International Searching Authority Re. Application No. PCT/IL2011/050010.
International Search Report Dated Jul. 19, 2004 From the International Searching Authority Re.: Application No. PCT/IL03/01045.
Office Action Dated Feb. 1, 2009 From the Israeli Patent Office Re.: Application No. 163285 and Its Translation Into English.
Office Action Dated Jun. 4, 2008 From the Israeli Patent Office Re.: Application No. 163285.
Office Action Dated Nov. 5, 2009 From the Israel Patent Office Re.: Application No. 172788 and Its Translation Into English.
Office Action Dated Jan. 8 2009 From the Israeli Patent Office Re.: Application No. 172788 and Its Translation Into English.
Official Action Dated May 2, 2008 From the US Patent and Trademark Office Re.: U.S. Appl. No. 11/656,542.
Official Action Dated Sep. 2, 2008 From the US Patent and Trademark Office Re.: U.S. Appl. No. 11/471,657.
Official Action Dated Oct. 3, 2012 From the US Patent and Trademark Office Re. U.S. Appl. No. 12/654,461.
Official Action Dated Oct. 5, 2010 From the US Patent and Trademark Office Re. U.S. Appl. No. 11/632,410.
Official Action Dated Oct. 7, 2010 From the US Patent and Trademark Office Re.: U.S. Appl. No. 12/385,471.
Official Action Dated Apr. 8, 2013 From the US Patent and Trademark Office Re. U.S. Appl. No. 11/632,410.
Official Action Dated Sep. 10, 2007 From the US Patent and Trademark Office Re.: U.S. Appl. No. 11/471,657.
Official Action Dated Dec. 12, 2008 From the US Patent and Trademark Office Re.: U.S. Appl. No. 11/656,542.
Official Action Dated Jun. 14, 2010 From the US Patent and Trademark Office Re.: U.S. Appl. No. 12/458,163.
Official Action Dated May 15, 2009 From the US Patent and Trademark Office Re.: U.S. Appl. No. 11/471,657.
Official Action Dated Dec. 16, 2008 From the US Patent and Trademark Office Re.: U.S. Appl. No. 10/562,852.
Official Action Dated Mar. 16, 2010 From the US Patent and Trademark Office Re.: U.S. Appl. No. 12/385,471.
Official Action Dated Aug. 21, 2009 From the US Patent and Trademark Office Re.: U.S. Appl. No. 10/562,852.
Official Action Dated Feb. 23, 2006 From the US Patent and Trademark Office Re.: U.S. Appl. No. 10/235,852.
Official Action Dated Jan. 24, 2013 From the US Patent and Trademark Office Re. U.S. Appl. No. 11/632,410.
Official Action Dated Sep. 27, 2012 From the US Patent and Trademark Office Re. U.S. Appl. No. 11/632,410.

(56) References Cited

OTHER PUBLICATIONS

Requisition by the Examiner Dated Aug. 3, 2010 From the Canadian Intellectual Property Office Re. Application No. 2,473,987.
Requisition by the Examiner Dated Oct. 9, 2012 From the Canadian Intellectual Property Office Re. Application No. 2,530,927.
Requisition by the Examiner Dated Jun. 11, 2012 From the Canadian Intellectual Property Office Re. Application No. 2,473,987.
Requisition by the Examiner Dated Jun. 30, 2011 From the Canadian Intellectual Property Office Re. Application No. 2,473,987.
Search Results: STN File, Registry, RN 379722-40-4 and Following Dated Dec. 31, 2001 for the Australian Patent Application No. 2004203461.
Supplementary European Search Report Dated Apr. 18, 2006 From the European Patent Office Re.: Application No. 03704977.2.
Supplementary Partial European Search Report Dated Dec. 9, 2009 From the European Patent Office Re.: Application No. 04744917.8.
Translation of Decision on Rejection Dated Jun. 5, 2012 From the State Intellectual Property Office of the People's Republic of China Re. Application No. 2004800248446.3.
Translation of Notice of Reason for Rejection Dated Jun. 3, 2011 From the Japanese Patent Office Re.: Application No. 2006-518484.
Translation of Notice of Reason for Rejection Dated Mar. 9, 2010 From the Japanese Patent Office Re.: Application No. 2006-518484.
Translation of Notice of the Reason for Rejection Dated Oct. 22, 2009 From the Korean Intellectual Property Office Re.: Application No. 2004-7011868.
Translation of Office Action Dated Aug. 24, 2010 From the State Intellectual Property Office of the People's Republic of China Re. Application No. 2004800248446.3.
Translation of Reason for Rejection Dated Aug. 11, 2009 From the Japanese Patent Office Re.: Application No. 2003-563456.
Translation of the Notice of Reason of Rejection Dated Jul. 11, 2008 From the Japanese Patent Office Re.: Application No. 2003-563456.
Written Opinion Dated Jun. 15, 2006 From the International Preliminary Examining Authority Re.: Application No. PCT/IL03/00079.
Anguiano et al. "Protofibrillar Islet Amyloid Polypeptide Permeabilizes Synthetic Vesicles by a Pore-Like Mechanism That May Be Relevant to Type II Diabetes", Biochemistry, 41: 11338-11343, 2002.
Arvinte et al. "The Structure and Mechanism of Formation of Human Calcitonin Fibrils", The Journal of Biological Chemistry, 268(9): 6415-6422, 1993.
Austin et al. "Medical Progress: Calcitonin. Physiology and Pathophysiology", The New England Journal of Medicine, 304(5): 269-278, 1981.
Ausubel et al. Current Protocols in Molecular Biology, 1(Suppl.63).
Azriel et al. "Analysis of the Minimal Amyloid-Forming Fragment of the Islet Amyloid Polypeptide. An Experimental Support for the Key Role of the Phenylalanine Residue in Amyloid Formation", The Journal of Biological Chemistry, XP002555838, 276(36): 34156-34161, Sep. 7, 2001.
Balaram "De Novo Design: Backbone Conformational Constraints in Nucleating Helices and Beta-Hairpins", Journal of Peptide Research, 54: 195-199, 1999.
Balbach et al. "Supramolecular Structure in Full-Length Alzheimer's Beta-Amyloid Fibrils: Evidence for a Parallel Beta-Sheet Organization From Solid-State Nuclear Magnetic Resonance", Biophysical Journal, 83: 1205-1216, 2002.
Baltzer et al. "De Novo Design of Proteins—What Are the Rules?", Chemical Reviews, 101(10): 3153-3163, 2001.
Banerji et al. "A Lymphocyte-Specific Cellular Enhancer Is Located Downstream of the Joining Region in Immunoglobulin Heavy Chain Genes", Cell, 33: 729-740, 1983.
Bauer et al. "Interfacial Adsorption and Aggregation Associated Changes in Secondary Structure of Human Calcitonin Monitored by ATR-FTIR Spectroscopy", Biochemistry, 33: 12276-12282, 1994.
Benvenga et al. "Homology of Calcitonin With the Amyloid-Related Proteins", Journal of Endocrinological Investigation, 17: 119-122, 1994.
Berger et al. "Calcitonin-Like Immunoreactivity of Amyloid Fibrils in Medullary Thyroid Carcinomas", Virchows Archiv A Pathological Anatomy and Histopathology, 412: 543-551, 1988.
Bird et al. "Single-Chain Antigen-Binding Proteins", Science, 242(4877): 423-426, 1988.
Boerner et al. "Production of Antigen-Specific Human Monoclonal Antibodies From In Vitro-Primed Human Splenocytes", The Journal of Immunology, 147(1): 86-95, 1991.
Booth et al. "Instability, Unfolding and Aggregation of Human Lysozyme Variants Underlying Amyloid Fibrillogenesis", Nature, 385: 787-793, 1997.
Brown et al. "Human Spongiform Encephalopathy: The National Institutes of Health Series of 300 Cases of Experimentally Transmitted Disease", Annals of Neurology, 35(5): 513-529, May 1994.
Burger et al. "Incorporation of ?-Trifluoromethyl Substituted [Alpha]-Amino Acids Into C- and N-Terminal Position of Peptides and Peptide Mimetics Using Multicomponent Reactions", Tetrahedron, 54: 5915-5928, 1998.
Bursavich et al. "Designing Non-Peptide Peptidomimetics in the 21st Century: Inhibitors Targeting Comformational Ensembles", Journal of Medical Chemistry, 45(3): 541-558, 2002.
Byrne et al. "Mutiplex Gene Regulation: A Two-Tiered Approach to Transgene Regulation in Transgenic Mice", Proc. Natl. Acad. Sci. USA, 86: 5473-5477, 1989.
Calame et al. "Transcriptional Controlling Elements in the Immunoglobulin and T Cell Receptor Loci", Advances in Immunology, 43: 235-275, 1988.
Cherny et al. "The Formation of *Escherichia coli* Curli Amyloid Fibrils is Mediated by Prion-Like Peptide Repeats", Journal of Molecular Biology, 352(2): 245-252, 2005.
Chopin et al. "Analysis of Six Prophages in *Lactococcus lactis* IL1403: Different Genetic Structure of Temperate and Virulent Phage Populations", Nucleic Acids Research, 29(3): 644-651, 2001.
Choplin "Computers and the Medicinal Chemist", Comprehensive Medicinal Chemistry, 4(Chap.17.2): 33-58, 1990.
Chou et al. "Conformational Parameters for Amino Acids in Helical, Beta-Sheet, and Random Coil Regions Calculated From Proteins", Biochemistry, 13(2): 211-222, 1974.
Claessens et al. "Review Commentary: Pi-Pi Interactions in Self-Assembly", Journal of Physical Organic Chemistry, 10: 254-272, 1997.
Cole et al. "Review Commentary: Pi-Pi Interactions in Self-Assembly", Journal of Physical Organic Chemistry, 10: 254-272, 1997.
Cole et al. "The EBV-Hybridoma Technique and Its Application to Human Lung Cancer", Monoclonal Antibodies and Cancer Therapy, Proceedings of the Roche-UCLA Symposium, Park City, Utah, p. 77-96, 1985.
Cooper "Selective Amyloid Staining As a Function of Amyloid Composition and Structure. Histochemical Analysis of the Alkaline Congo Red. Standardized Toluidine Blue, and Iodine Methods", Laboratory Investigation, 31(3): 232-238, 1974.
Copp "Endocrine Regulation of Calcium Metabolism", Annual Reviews in Physiology, 32: 61-86, 1970.
Cote et al. "Generation of Human Monoclonal Antibodies Reactive With Cellular Antigens", Proc. Natl. Acad. Sci. USA, 80: 2026-2030, 1983.
Coughlan et al. "Factors Influencing the Processing and Function of the Amyloid Beta Precursor Protein—A Potential Therapeutic Target in Alzheimer's Disease?", Pharmacology and Therapeutics, 86: 111-144, 2000.
Damas et al. "Review: TTR Amyloidosis—Structural Features Leading to Protein Aggregation and Their Implications on Therapeutic Strategies", Journal of Structural Biology, 130: 290-299, 2000.
Edlund et al. "Cell-Specific Expression of the Rat Insulin Gene: Evidence for Role of Two Distinct 5' Flanking Elements", Science, 230(4278): 912-916, 1985.
Ferrannini "Insulin Resistance Versus Insulin Deficiency in Non-Insulin-Dependent Diabetes Mellitus: Problems and Prospects", Endocrine Reviews, 19(4): 477-490, 1998.
Findeis "Approaches to Discovery and Characterization of Inhibitors of Amyloid Beta-Peptide Polymerization", Biochimica et Biophysica Acta, 1502: 76-84, 2000.

(56) References Cited

OTHER PUBLICATIONS

Findeis et al. "Modified-Peptide Inhibitors of Amyloid B-Peptide Polymerization", Biochemistry, 38: 6791-6800, 1999.
Fingl et al. "Inroduction: General Principles", The Pharmacological Basis of Therapeutics, 5th Ed., Sec.I(Chap.1): 1-53, 1975.
Fishwild et al. "High-Avidity Hum IgGK Monoclonal Antibodies From a Novel Strain of Minilocus Transgenic Mice", Nature Biotechnology, 14: 845-851, 1996.
Forloni et al. "Anti-Amyloidogenic Activity of Tetracyclines: Studies in Vitro", FEBS Letters, 487(3): 404-407, 2001. Figs. 1,3.
Freshney "Animal Cell Culture—A Practical Approach", IRL Press.
Friedman "Chemistry, Nutrition, and Microbiology of D-Amino Acids", Journal of Agriculture and Food Chemistry, 47(9): 3457-3479, 1999.
Frydman-Marom et al. "Cognitive-Performance Recovery of Alzheimer's Disease Model Mice by Modulation of Early Soluble Amyloidal Assemblies", Angewnadte Chemie, International Edition, XP002601658, 48(11): 1981-1986, Jan. 1, 2009. p. 1985, col. 1, Line 4—p. 1986, col. 1, Line 4, Fig. 1.
Gait "Oligonucleotide Synthesis—A Practical Approach", IRL Press.
Gajdusek "Unconventional Viruses and the Origin and Disappearance of Kuru", Science, 197(4307): 943-960, 1977.
Garofalo et al. "A Series of C-Terminal Amino Alcohol Dipeptide ABeta Inhibitors", Bioorganic & Medicinal Chemistry Letters, 12(21): 3051-3053, 2002.
Gazit "A Possible Role for 'Phi'-Stacking in the Self-Assembly of Amyloid Fibrils", The FASEB Journal, 16: 77-83, 2002.
Gazit "Global Analysis of Tandem Aromatic Optapeptide Repeats: The Significance of the Aroma-Glycine Motif", Bioinformatics Discovery Note, 18(6): 880-883, 2002.
Gazit "The 'Correctly Folded' State of Proteins: Is it a Metastable State?", Angewandte Chemie, International Edition, 41(2): 257-259, 2002.
Gillard et al. "Controlling Self-Assembly", Chemical European Journal, 3(12): 1933-1940, 1997.
Gillmore et al. "Amyloidosis a Review of Recent Diagnostic and Therapeutic Developments", British Journal of Haematology, 99: 245-256, 1997.
Glenner "Amyloid Deposits and Amyloidosis. The Beta-Fibrilloses (First of Two Parts)", The New England Journal of Medicine, 302(23): 1283-1292, 1980.
Gorman et al. "Alzheimer Beta-Amyloid Peptides, Structures of Amyloid Fibrils and Alternate Aggregation Products", Biopolymers, 60: 381-394, 2001. Claims 1-16, 22-26, 70-80, 91-100.
Grateau "Le Curli du Coli: Une Variete Physiologique d'Amilose [Coli's Curli or How Amyloid Can be Physiological]", Medecine Sciences, 18(6-7): p. 664, 2002.
Haeggqvist et al. "Medin: An Integral Fragment of Aortic Smooth Muscle Cell-Produced Lactadherin Forms the Most Common Human Amyloid", Proc. Natl. Acad. Sci. USA, 96: 8669-8674, 1999.
Han et al. "Technetium Complexes for the Quantitation of Brain Amyloid", Journal of the American Chemical Society, 118: 4506-4507, 1996.
Harlow et al. "Antibodies: A Laboratory Manual", Cold Spring Harbor Laboratory, p. III-IX, 1988.
Harrison et al. "Amyloid Peptides and Proteins in Review", Reviews in Physiology, Biochemistry and Pharmacology, 159: 1-77, 2007.
Hayden et al. "'A' Is for Amylin and Amyloid in Type 2 Diabetes Mellitus", JOP Journal of the Pancreas (Online), 2(4): 124-139, 2001.
Hoeppener et al. "Islet Amyloid and Type 2 Diabetes Mellitus", The New England Journal of Medicine, 343(6): 411-419, 2000.
Hoeppener et al. "The Complete Islet Amyloid Polypeptide Precursor Is Encoded by Two Exons", Biochemical & Biophysical Research Communications, 189: 1569-1577, 1993. Database, Accession No. S04016, 1993. Claims 1-16, 22-26.
Hoogenboom et al. "By-Passing Immunisation. Human Antibodies From Synthetic Repertoires of Germline VH Gene Segments Rearranged In Vitro", Journal of Molecular Biology, 227: 381-388, 1992.

Inbar et al. "Localization of Antibody-Combining Sites Within the Variable Portions of Heavy and Light Chains", Proc. Natl. Acad. Sci. USA, 69(9): 2659-2662, 1972.
Inglot "Comparison of the Antiviral Activity In Vitro of Some Non-Steroidal Anti-Inflammatory Drugs", Journal of General Virology, 4(2): 203-214, 1969.
Inouye et al "Synthesis and Biological Properties of the 10-Substituted Analogues of ACTH-(1-18)-NH2", Shionogi Research Laboratory, Fukushima-Ku, Osaka, p. 177-182, 1978.
Jelokhani-Niaraki et al "Changes in Conformation and Antimicrobial Properties Caused by Replacement of D-Amino Acids With Alpha-Aminoisobutyric Acid in the Gramicidin Backbbone: Synthesis and Circular Dichroic Studies", Journal of the Chemical Society Perkin Transactions, 2: 1 187-1193, 1992.
Johnson et al. "Islet Amyloid, Islet-Amiloid Polypeptide, and Diabetes Mellitus", The New England Journal of Medicine, 321(8): 513-518, 1989. IDS in 45786.
Jones et al. "Replacing the Complementarity-Determining Regions in a Human Antibody With Those From a Mouse", Nature, 321: 522-525, 1986.
Kahn et al. "Islet Amyloid: A Long-Recognized But Underappreciated Pathological Feature of Type 2 Diabetes", Diabetes, 48: 241-253, 1999.
Kamihira et al. "Conformational Transitions and Fibrillation Mechanism of Human Calcitonin as Studied by High-Resolution Solid-State 13C NMR [in Process Citation]", Protein Science, 9: 867-877, 2000.
Kanaori et al. "Study of Human Calcitonin Fibrillation by Proton Nuclear Magnetic Resonance Spectroscopy", Biochemistry, 34: 12138-12143, 1995.
Kapurniotu et al. "Structure-Based Design and Study of Non-Amyloidogenic, Double N-Methylated IAPP Amyloid Core Sequences as Inhibitors of IAPP Amyloid Formation and Cytotoxicity", Journal of Molecular Biology, 315: 339-350, 2002.
Kapurniotu et al. Database, Accession No. AAW93015, 1991.
Karle et al. "Structural Characteristics of Alpha-Helical Peptide Molecules Containing Aib Residues", Biochemistry, 29(29): 6747-6756, Jul. 24, 1990.
Kedar et al. "In Vitro Synthesis of 'Amyloid' Fibrils From Insulin, Calcitonin and Parathormone", Israel Journal of Medical Science, 12(10): 1137-1140, 1976.
Kilkarni et al. "Investigation of the Effect of Antisense Oligodeoxynucleotides to Islet Amyloid Polypeptide mRNA on Insulin Release, Content and Expression", Journal of Endocrinology, 151: 341-348, 1996.
Kohler et al. "Continuous Cultures of Fused Cells Secreting Antibody of Predefined Specifity", Nature, 256: 495-497. 1975.
Kozbor et al. "Specific Immunoglobulin Production and Enhanced Tumorigenicity Following Ascites Growth of Human Hybridomas", Journal of Immunological Methods, 81: 31-42, 1985.
Kuner et al. "Controlling Polmerization of Beta-Amyloid and Prion-Derived Peptides With Synthetic Smal Molecule Ligands", Journal of Biological Chemistry, 275(3): 1673-1678, 2000.
Kyte et al. "A Simple Method for Displaying the Hydropathic Character of a Protein", Journal of Molecular Biology, 157: 105-132, 1982.
Lansbury "Following Nature's Anti-Amyloid Strategy", Nature Biotechnology, 19(2): 112-113, 2001. p. 112, Left-Hand Col., Paragraph 1—Middle Col., Paragraph 1.
Larrick et al. "PCR Amplification of Antibody Genes", Methods: A Companion to Methods in Enzymology, 2(2): 106-110, 1991.
Lonberg et al. "Antigen-Specific Human Antibodies From Mice Comprising Four Distinct Genetic Modifications", Nature, 368(6474): 856-859, 1994.
Lonberg et al. "Human Antibodies From Transgenic Mice", International Review of Immunology, 13: 65-93, 1995.
Lowe et al. "Structure-Function Relationships for Inhibitors of Beta-Amyloid Toxicity Containing the Recognition Sequence KLVFF", Biochemistry, 40: 7882-7889, 2001.
Lyon et al. "Self-Assembly and Gelation of Oxidized Gluthathione in Organic Solvents", Journal of the American Chemical Society, 123: 4408-4413, 2001.

(56) References Cited

OTHER PUBLICATIONS

Maji et al. "Fibril-Forming Model Synthetic Peptides Containing 3-Aminophenylacetic Acid", Tetrahedron, 58(43): 8695-8702, 2002.
Marks et al. "By-Passing Immunization—Human Antibodies From V-Gene Libraries Displayed on Phage", Journal of Molecular Biology, 222: 581-597, 1991.
Marks et al. "By-Passing Immunization: Building High Affinity Human Antibodies by Chain Shuffling", Bio/Technology, 10: 779-783, 1992.
Marshak et al. "Strategies for Protein Purification and Charcterization, A Laboratory Course Manual", Cold Spring Harbor Laboratory Press, 1996.
Mason et al. "Design Strategies for Anti-Amyloid Agents", Current Opinion in Structural Biology, 13: 1-7, 2003.
Maury et al. "Creation of Amyloid Fibrils From Mutant ASN187 Gelsolin Peptides", Biochemical and Biophysical Research Communications, 183(1): 227-231, 1992.
Mazor et al. "Identification and Characterization of a Novel Molecular-Recognition and Self-Assembly Domain Within the Islet Amyloid Polypeptide", Journal of Molecular Biology, 322: 1013-1024, 2002.
McGaughey et al. "Pi-Stacking Interactions. Alive and Well in Proteins", The Journal of Biological Chemistry, 273(25): 15458-15463, Jun. 19, 1998.
McLaurin et al. "Cyclohexanehexol Inhibitors of A? Aggregation Prevent and Reverse Alzheimer Phenotype in a Mouse Model", Nature Medicine, 12(7): 801-808, Jul. 2006.
Medore et al. "Fatal Familial Insomnia, A Priori Disease With a Mutation at Codon 178 of the Prion Protein Gene", The New England Journal of Medicine, 326(7): 444-449, 1992.
Merlini et al. "Intereaction of the Anthracycline 4'-Iodo-4'-Deoxydoxorubicin With Amyloid Fibrils: Inhibition of Amyloidogenesis", Proc. Natl. Acad. Sci. USA, 92: 2959-2963, 1995.
Moriatry et al. "Effects of Sequential Proline Substitutions on Amoyloid Formation by Human Amylin20-29", Biochemistry, 38: 1811-1818, 1999.
Morrison "Success in Specification", Nature, 368(6474): 812-813, 1994.
Mosmann "Rapid Colorimetric Assay for Cellular Growth and Survival: Application to Proliferation and Cytotoxicity Assays", Journal of Immunological Methods, 65: 55-63, 1983.
Mosselman et al. "Islet Amyloid Polipeptide: Identification and Chromosomal Localization of the Human Gene", FEBS Letters, 239(2): 227-232, 1988.
Mosselman et al. "The Complete Islet Amyloid Polypeptide Precursor Is Encoded by Two Exons", FEBS Letters, 247: 154-158, 1989, Database Accession No. 504016.
Mutter "Studies on the Coupling Rates in Liquid-Phase Peptide Synthesis Using Competition Experiments", International Journal of Peptide Protein Research, 13: 274-277, 1979.
Nadin et al. "Synthesis and Gamma-Secretase Activity of APP Substrate-Based Hydroxyethylene Dipeptide Isosteres", Bioorganic & Medicinal Chemistry Letters, 13(1): 37-41, Jan. 2003.
Neuberger "Generating High-Avidity Human Mabs in Mice", Nature Biotechnology, 14: 826, 1996.
Noursadeghi et al. "Role of Serum Amyloid P. Component in Bacterial Infection: Protection of the Host or Protection of the Pathogen", Proc. Natl. Acad. Sci. USA, PNAS, 97(26): 14584-14589, Dec. 19, 2000.
Novials et al. "Reduction of Islet Amylin Expression and Basal Secretion by Adenovirus-Mediated Delivery of Amylin Antisense cDNA", Pancreas, 17(2): 182-186, 1998.
Offen et al. "A Low Molecular Weight Copper Chelator Crosses the Blood-Brain Barrier and Attenuates Experimental Autoimmune Encephalomyelitis", Journal of Neurochemistry, 89: 1241-1251, 2004.
Orlandi et al. "Cloning Immunoglobulin Variable Domains for Expression by the Polymerase Chain Reaction", Proc. Natl. Acad. Sci. USA, 86: 3833-3837, 1989.
Pack et al. "Improved Bivalent Miniantibodies, With Identical Avidity as Whole Anitbodies, Produced by High Cell Density Fermentation of *Escherichia coli*", Bio/Technology, 11: 1271-1277, 1993.
Pavia et al. "Antimicrobial Activity of Nicotine Against a Spectrum of Bacterial and Fungal Pathogens", Journal of Medical Microbiology, 49(7): 675-676, 2000.
Perbal "A Practical Guide to Molecular Cloning", Wiley-Interscience Publication.
Petkova et al. "A Structural Model for Alzheimer's Beta-Amyloid Fibrils Based on Experimental Constraints From Solid State NMR", Proc. Natl. Acad. Sci. USA, 99(26): 16742-16747, 2002.
Pettmann et al. "Morphological and Biochemical Maturation of Neurones Cultured in the Absence of Glial Cells", Nature, 281: 378-380, 1979.
Pinkert et al. "An Albumin Enhancer Located 10 Kb Upstream Functions Along With Its Promoter to Direct Efficient, Liver-Specific Expression in Transgenic Mice", Genes & Development, 1: 268-276, 1987.
Pispisa et al. "A Spectroscopic and Molecular Mechanics Investigation on a Series of AIB-Based Linear Peptides and a Peptide Template, Both Containing Tryptophan and a Nitroxide Derivative as Probes", Biopolymers, 53: 169-181, 2000.
Porter "The Hydrolysis of Rabbit Gamma-Globulin and Antibodies With Crystalline Papain", Biochemical Journal, 73: 119-126, 1959.
Presta "Antibody Engineering", Current Opinion in Structural Biology, 2: 593-596, 1992.
Puchtler et al. "A Review of Early Concepts of Amyloid in Context With Contemporary Chemical Literature From 1839 to 1859", The Journal of Histochemistry and Cytochemistry, 14(2): 123-134, 1966.
Reches et al. "Amyloid Fibril Formation by Pentapeptide and Tetrapeptide Fragments of Human Calcitonin", The Journal of Biological Chemistry, XP002276670, 277(38): 35475-35480, 2002.
Reches et al. "Casting Metal Nanowires Within Discrete Self-Assembled Peptide Nanotubes", Science, 300: 625-627, Apr. 2003.
Reza et al "Self-Assembling Organic Nanotubes Based on a Cyclic Peptide Architecture", Nature, 366: 324-327, 1993.
Riechmann et al. "Reshaping Human Antibodies for Therapy", Nature, 332: 323-329, 1988.
Sambrook et al. "Molecular Cloning: A Laboratory Manual", 2nd Edition, Cold Spring Harbor Laboratory,1989.
Sano "Prevention of Alzheimer's Disease: Where We Stand", Current Neurology and Neuroscience Reports, 2(5): 392-399, Oct. 2002. Abstract.
Seino "S20G Mutation of the Amylin Gene Is Associated With Type II Diabetes in Japans", Diabetologia, 44: 906-909, 2001.
Shetty et al. "Aromatic Pi-Stacking in Solution as Revealed Through the Aggregation of Phenylacetylene Macrocycles", Journal of the American Chemical Society, 118: 1019-1027, 1996.
Sigel-Causey et al. "Phylogeny of the Pelecaniformes: Molecular Systematics of a Privative Group", Avian Molecular Evolution and Systematics, academic Press, p. 159-171, NBCI GenBank, Accession No. AAB58518, 1997.
Sigma "Alphabetical List of Compounds: Phe-Phe, Phe-Pro, Phe-Val", Biochemicals and Reagents for Life Science Research, p. 774, 2000-2001.
Solomon et al. "Disaggregation of Alzheimer Beta-Amyloid by Site-Directed MAb", Proc. Natl. Acad. Sci. USA, 94: 4109-4112, 1997.
Soto et al. "Beta-Sheet Breaker Peptides Inhibit Fibrillogenesis in a Rat Brain Model of Amyloidosis: Implications for Alzheimer's Therapy", Nature Medicine, 4(7): 822-826, Jul. 1998.
Soto et al. "Inhibition of Alzheimer's Amyloidosis by Peptides That Prevent Beta-Sheet Conformation", Biochemical and Biophysical Research Communications, 226(3): 672-680, 1996.
Stephenson et al. "The 'Promiscuous Drug Concept' With Applications to Alzheimer's Disease", FEBS Letters, 579: 1338-1342, 2005.
Stites et al. "Tables of Content", Basic & Clinical Immunology, 8th Ed.: 12 P.
Sun et al. "Aromatic Van der Waals Clusters: Structure and Nonrigidity", Journal of Physical Chemistry, 100: 13348-13366, 1996.
Tenidis et al. "Identification of a Penta- and Hexapeptide of Islet Amyloid Polypeptide (LAPP) With Amyloidogenic and Cytotoxic Propereties", Journal of Molecular Biology, 295(4): 1055-1071, 2000.

(56) References Cited

OTHER PUBLICATIONS

Tjernberg et al. "Arrest of Beta-Amyloid Fibril Formation by a Pentapeptide Ligand", The Journal of Biological Chemistry, 271(15): 8545-8548, Apr. 12, 1996.
Tjernberg et al. "Controlling Amyloid Beta-Peptide Fibril Formation With Protease-Stable Ligands", The Journal of Biological Chemistry, 272(19): 12601-12605, 1997.
Toniolo et al. "Control of Peptide Conformation by the Thorpe-Ingold Effect (CAlpha-Tetrasubstitution)", Biopolymers (Peptide Science), 60(6): 396-419, 2001.
Tonkinson et al. "Antisense Oligodeoxynucleotides as Clinical Therapeutic Agents", Cancer Investigation, 14(1): 54-65, 1996.
Trivedi et al. "Second Generation 'Peptoid'CCK-B Receptor Antagonists: Identification and Development of N-(Adamantyloxycarbonyl)-Alpha-Methyl-(R)-Tryptophan Derivative (CI-1015) With an Improved Pharmacokinetic Profile", Journal of Medicinal Chemistry, XP002625505, 41: 38-45, Jan. 1, 1998. p. 44, col. 1, Lines 35-54, Compounds 25, 26.
Tsai et al. "Synthesis of AIB-Containing Peptidomimetics as Potential Inhibitors of Alzheimer's Gamma-Secretase", 218th ACS National Meeting, New Orleans, USA, Meeting Abstract, MEDI-018, 1999. Abstract.
Verhoeyen et al. "Reshaping Human Antibodies: Grafting an Antilysozyme Activity", Science, 239: 1534-1536, 1988.
Vescovi et al. "Synthesis and Functional Studies of THF-Gramicidin Hybrid Ion Channels", Organic & Biomolecular Chemistry, 1(16): 2983-2997, Aug. 21, 2003.
Vidal et al. "A Stop-Codon Mutation in the BRI Gene Associated With Familial British Dementia", Nature, 399: 776-781, 1999.
Westermark "Amyloid and Polypeptide Hormones: What is Their Interrelationship?", Amyloid: International Journal of Experimental & Clinical Investigation, 1: 47-60, 1994.
Westermark "Islet Amyloid Polypeptide: Pinpointing Amino Acid Residues Linked to Amyloid Fibril Formation", Proc. Natl. Acad. Sci. USA, 87: 5036-5040, 1990.
Whitlow et al. "Single-Chain Fv Proteins and Their Fusion Proteins", Methods: A Companion to Methods in Enzymology, 2(2): 97-105, 1991.
Wilesmith et al. "Bovine Spongiform Encephalopathy", Current Topics in Microbiology & Immunology, 172: 21-38, 1991.
Winoto et al. "A Novel, Inducible and T Cell-Specific Enhancer Located at the 3' End of the T Cell Receptor Alpha Locus", The EMBO Journal, 8(3): 729-733, 1989.
Winter et al. "Man-Made Antibodies", Nature, 349: 293-299, 1991.
Wolfenden et al. "Affinities of Amino Acid Side Chains for Solvent Water", Biochemistry, 20: 849-855, 1981.
Yamada et al. "Study of the Enzymatic Degradation of Endomorphin Analogs Containing Alpha,Alpha-Disubstituted Glycine", Peptide Science, 2000: 421-424, 2001.
Yang et al. "Curcumin Inhibits Formation of Amyloid Beta Oligomers and Fibrils, Binds Plaques, and Reduces Amyloid In Vivo", The Journal of Biological Chemistry, 280(7): 5892-5901, Feb. 18, 2005.
Zaidi et al. "Forty Years of Calcitonin—Where Are We Now? A Tribute to the Work of Iain Macintyre, FRS", Bone, 30(5): 655-663, 2002.
Notice of Allowance Dated May 28, 2013 From the US Patent and Trademark Office Re. U.S. Appl. No. 12/654,461.
International Preliminary Report on Patentability Dated May 30, 2013 From the International Bureau of WIPO Re. Application No. PCT/IL2011/050010.
Notice of Reason for Rejection Dated Feb. 25, 2014 From the Japanese Patent Office Re. Application No. 2012-165656 and Its Translation Into English.
Gazit "Mechanistic Studies of Process of Amyolid Fibrils Formation by the Use of Peptide Fragments and Analogues: Implications for the Design of Fibrillization Inhibitors", Current Medicinal Chemistry, 9(19): 1725-1735, Oct. 2002.
European Search Report and the European Search Report Dated Mar. 19, 2014 From the European Patent Office Re. Application No. 13191182.8.
Venkatraman et al. "Design of Folded Peptides", Chemical Reviews, XP002720975, 101(10): 3131-3152, Oct. 2001. p. 3134-3135.
Official Action Dated Apr. 14, 2014 From the US Patent and Trademark Office Re. U.S. Appl. No. 13/975,414.
Notification of Office Action Dated Jun. 12, 2014 From the State Intellectual Property Office of the People's Republic of China Re. Application No. 201180055035.X and Its Translation Into English.
Notice of Reason for Rejection Dated Dec. 2, 2014 From the Japanese Patent Office Re. Application No. 2012-165656 and Its Translation Into English.
Formaggio et al. "Disruption of the Beta-Sheet Structure of a Protected Pentapeptide, Related to the Beta-Amyloid Sequence 17-21, Induced by a Single, Helicogenic C[Alpha]-Tetrasubstituted Alpha-Amino Acid", Journal of Peptide Science, 9: 461-466, 2003.

\* cited by examiner

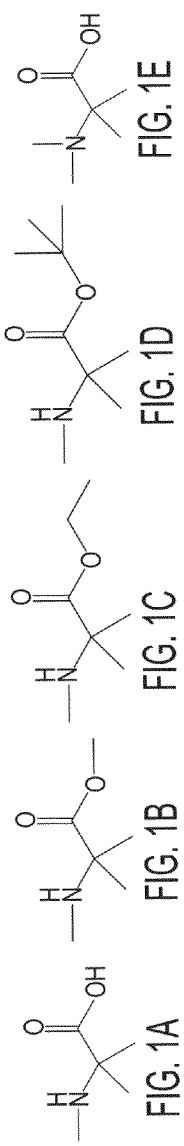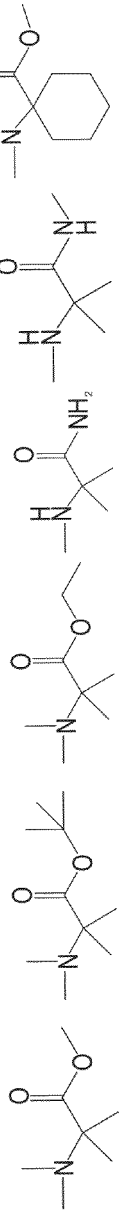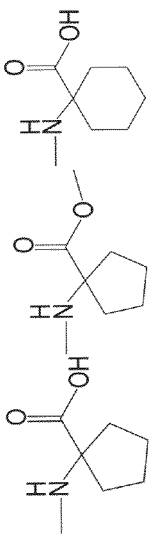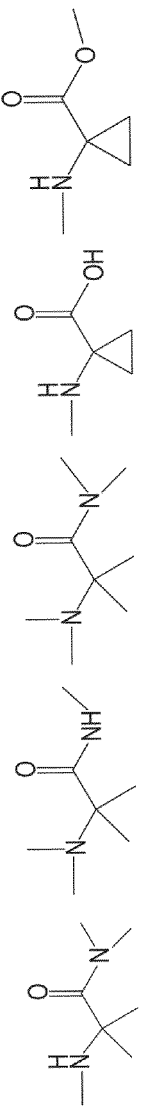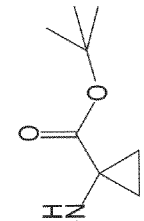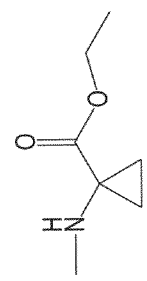

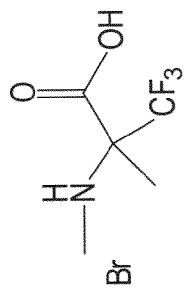
FIG. 1A*
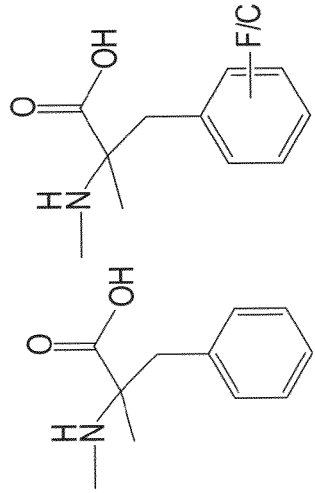
FIG. 1Z
FIG. 1Y
FIG. 1X
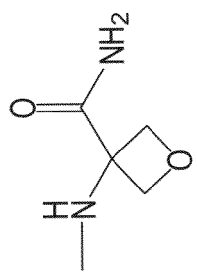
FIG. 1C*
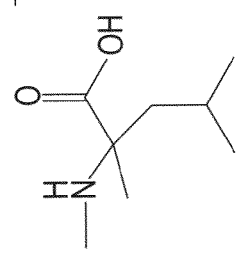
FIG. 1W
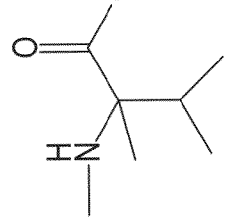
FIG. 1V
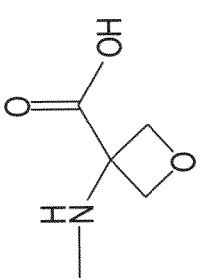
FIG. 1B*
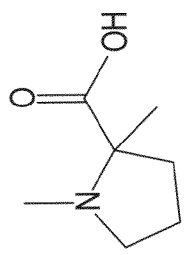

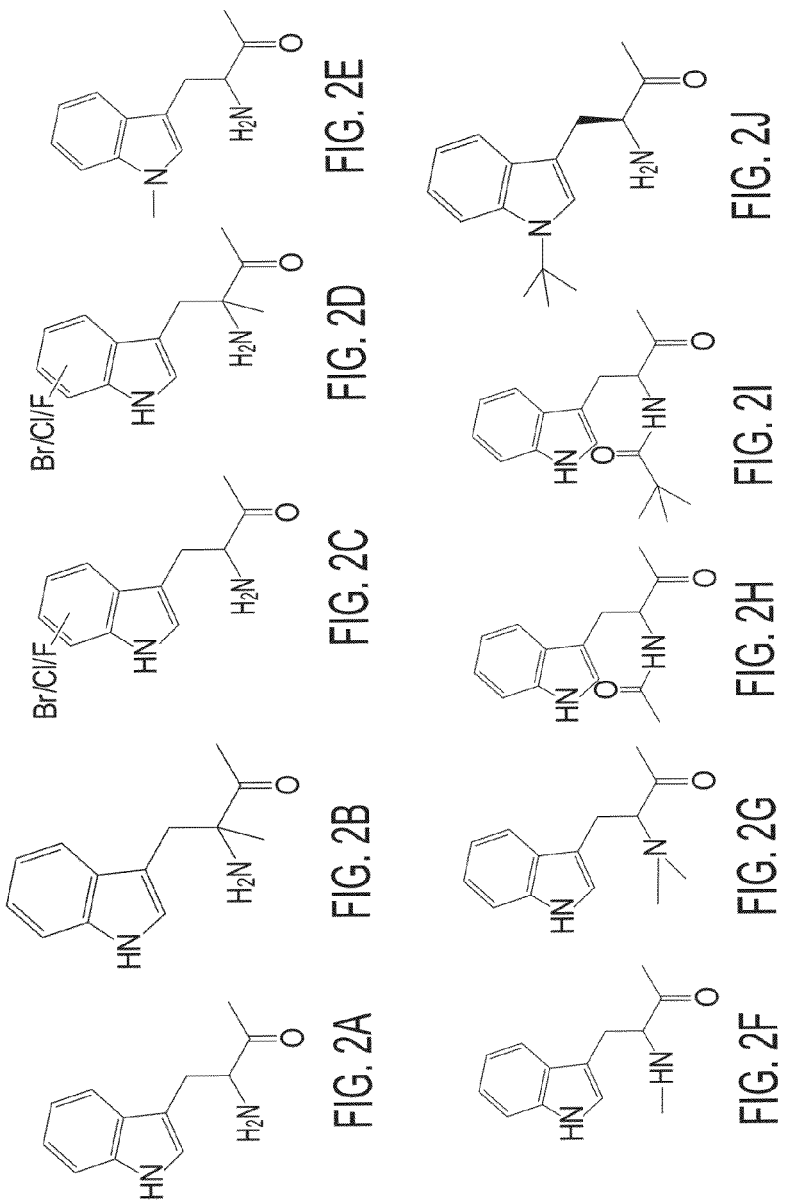

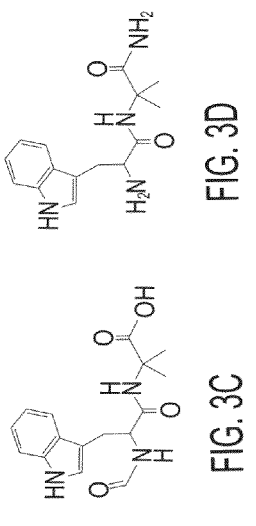
FIG. 3A
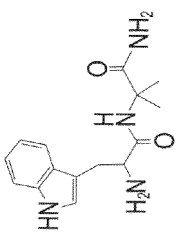
FIG. 3B
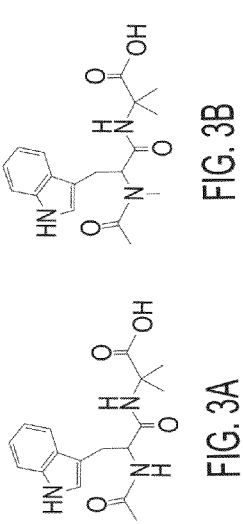
FIG. 3C
FIG. 3D
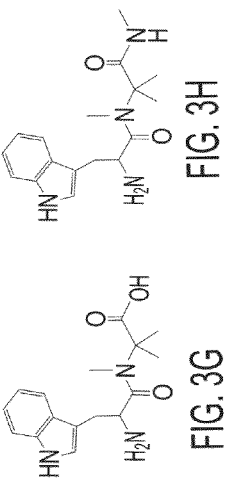
FIG. 3E
FIG. 3F
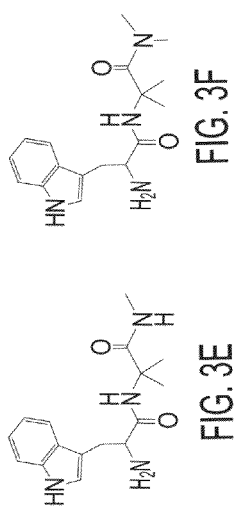
FIG. 3G
FIG. 3H
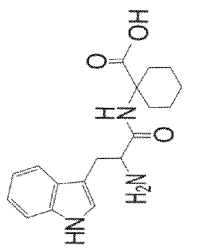
FIG. 3I
FIG. 3J
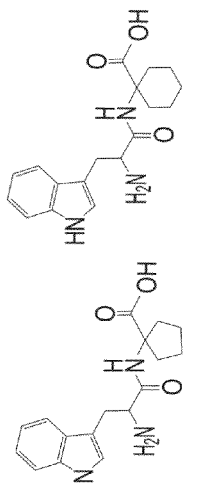
FIG. 3K
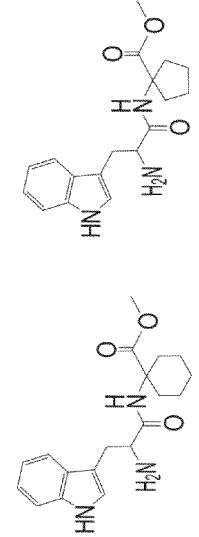
FIG. 3L

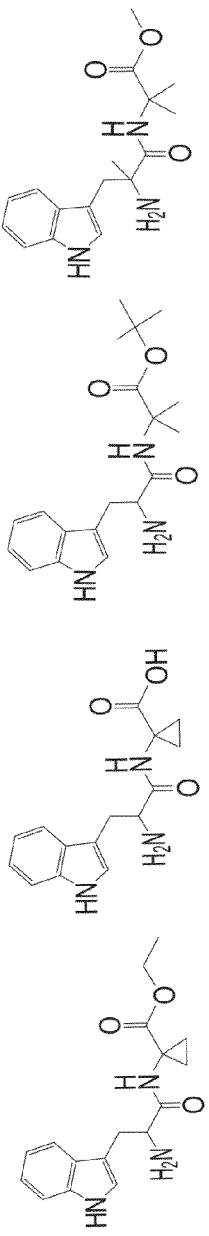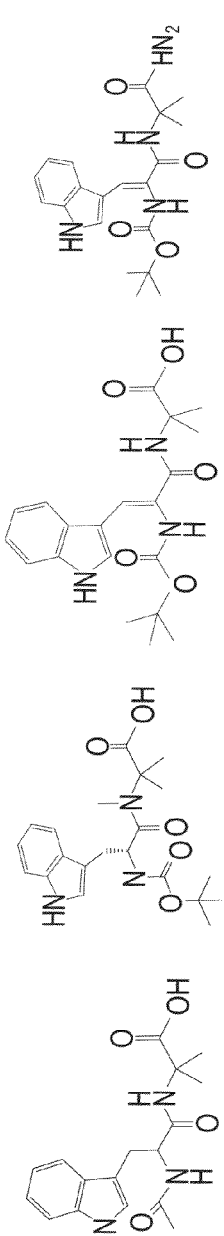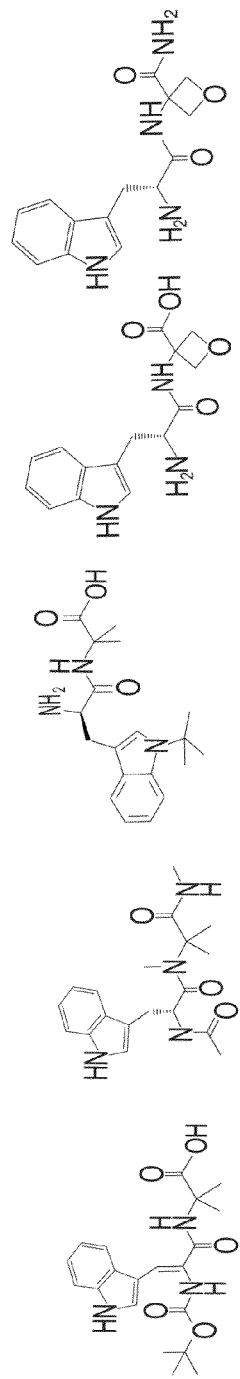

DIPEPTIDE ANALOGS FOR TREATING CONDITIONS ASSOCIATED WITH AMYLOID FIBRIL FORMATION

RELATED APPLICATIONS

This application is a National Phase of PCT Patent Application No. PCT/IL2011/050010 having International filing date of Nov. 15, 2011, which claims the benefit of priority under 35 USC §119(e) of U.S. Provisional Patent Application No. 61/413,488 filed on Nov. 15, 2010 and European Patent Application No. 10191253.3 filed on Nov. 15, 2010. The contents of the above applications are all incorporated by reference as if fully set forth herein in their entirety.

FIELD AND BACKGROUND OF THE INVENTION

The present invention, in some embodiments thereof, relates to novel therapeutic agents and, more particularly, but not exclusively, to dipeptides and analogs thereof, which prevent amyloid fibril formation and thus can be used in the treatment of amyloid associated diseases, such as type II diabetes mellitus, Alzheimer's dementia or diseases, systemic and localized amyloidosis, ocular diseases or disorders (e.g., glaucoma) and prion-related encephalopathies.

Amyloid material deposition (also referred to as amyloid plaque formation) is a central feature of a variety of unrelated pathological conditions including Alzheimer's disease, prion-related encephalopathies, type II diabetes mellitus, familial amyloidosis and light-chain amyloidosis.

Amyloid material is composed of a dense network of rigid, nonbranching proteinaceous fibrils of indefinite length that are about 80 to 100 Å in diameter. Amyloid fibrils contain a core structure of polypeptide chains arranged in antiparallel or parallel β-pleated sheets lying with their long axes perpendicular to the long axis of the fibril [Both et al. (1997) Nature 385:787-93; Glenner (1980) N. Eng. J. Med. 302:1283-92; Balbach et al. (2002) Biophys J. 83:1205-16].

Approximately twenty amyloid fibril proteins have been identified in-vivo and correlated with specific diseases. These proteins share little or no amino acid sequence homology, however the core structure of the amyloid fibrils is essentially the same. This common core structure of amyloid fibrils and the presence of common substances in amyloid deposits suggest that data characterizing a particular form of amyloid material may also be relevant to other forms of amyloid material and thus can be implemented in template design for the development of drugs against amyloid-associated diseases such as type II diabetes mellitus, Alzheimer's dementia or diseases, ocular diseases and disorders and prion-related encephalopathies.

Furthermore, amyloid deposits do not appear to be inert in vivo, but rather are in a dynamic state of turnover and can even regress if the formation of fibrils is halted [Gillmore et al. (1997) Br. J. Haematol. 99:245-56].

Thus, therapies designed to inhibiting the production of amyloid polypeptides or inhibiting amyloidosis may be useful for treating amyloid associated diseases.

One of the currently investigated therapeutic approaches of preventing amyloid fibril formation involves small molecules which can enter the CNS and disrupt polymerization of amyloid-beta peptides. Exemplary such compounds that have been reported in the art as effective in animal models include cyclohexanehexyl [McLaurin et al., Nature Medicine 12(7), 2006, pp. 801-808], including AZD-103; curcumin (Yang et al., J. Biol. Chem., 208(7), 2005, 5892-5901; and hydroxycholesterol derivatives, described and claims in WO 03/077869.

Some of the present inventors have previously disclosed that peptide aggregation into amyloid fibrils is governed by aromatic interactions. Based on these findings, a series of short peptides comprising an aromatic amino acids and a beta-sheet breaker amino acid was prepared and found effective in inhibiting amyloid fibril formation. U.S. Pat. No. 7,781,396 describes and claims such dipeptides. A potential peptide disclosed therein is the dipeptide D-Trp-Aib. Derivatives of this dipeptide are also disclosed therein.

Additional background art includes U.S. Pat. No. 7,732,479, and Yescovi et al. [Org. Biomol. Chem., 2003, 1, 2983-2997].

SUMMARY OF THE INVENTION

In a search for novel small molecules with improved performance in inhibiting amyloid fibril formation, the present inventors have designed and successfully prepared and practiced modified dipeptides based on the previously described D-Trp-Aib. These novel dipeptides thus include a Tryptophan moiety coupled to a beta-sheet breaking moiety, each of which being selected so as to impart to the dipeptidic compound stearic and/or lipophilic characteristics for achieving the desired performance.

According to as aspect of some embodiments of the present invention there is provided a dipeptide analog comprising a tryptophan (Trp) moiety coupled to a beta-sheet breaker moiety, with the proviso that either said Trp moiety is not Trp or said beta-sheet breaker moiety is not α-aminoisobutyric acid (Aib) or an ester thereof.

According to some embodiments of the invention, said beta-sheet breaker moiety is derived from α-aminoisobutyric acid (Aib).

According to some embodiments of the invention, the dipeptide analog is being of the general Formula I:

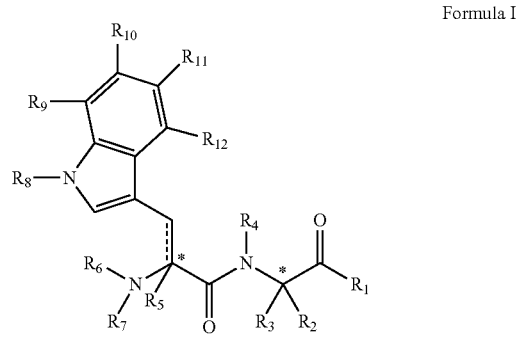

Formula I wherein:
 the dashed line denotes an optional double bond;
 each * independently denotes either (R) configuration or (S) configuration (relevant for the carbon substituted by $NR_6R_7$ in case the dashed line is absent);
 $R_1$ is selected from the group consisting of hydrogen, alkyl, aryl, hydroxy, alkoxy, aryloxy, thiol, thioalkoxy, thioaryloxy, halo and amine;
 $R_2$ and $R_3$ are each independently selected from the group consisting of alkyl, cycloalkyl, aryl, halo, haloalkyl, benzyl, or, alternatively, $R_2$ and $R_3$ form together a 3-8-membered saturated or unsaturated ring;

$R_4$ is selected from the group consisting of hydrogen, alkyl, cycloalkyl, aryl, carbonyl, thiocarbonyl, carboxylate and thiocarboxylate, or, alternatively, $R_4$ and $R_3$ form together a 4-8 membered saturated or unsaturated ring;

$R_5$ is selected from the group consisting of hydrogen and alkyl, or is absent in case the dashed line is a double bond;

$R_6$ and $R_7$ are each independently selected from the group consisting of hydrogen, alkyl, cycloalkyl, aryl, carbonyl, thiocarbonyl, carboxylate and thiocarboxylate, or, alternatively, $R_6$ and $R_7$ form together a 4-8-membered saturated or unsaturated ring;

$R_8$ is selected from the group consisting of hydrogen, alkyl, cycloalkyl, aryl, carbonyl, thiocarbonyl, carboxylate and thiocarboxylate; and $R_9$-$R_{12}$ are each independently selected from the group consisting of hydrogen, alkyl, cycloalkyl, aryl, alkoxy, thioalkoxy, aryloxy, thioaryloxy, halo, hydroxy, thiol, carbonyl, carboxylate and carbamate, provided that when $R_2$ is alkyl and $R_3$ is methyl, at least one of $R_4$, $R_5$ and $R_8$-$R_{12}$ is not hydrogen.

According to some embodiments of the invention, $R_1$ is selected from the group consisting of hydroxy, alkoxy and amine.

According to some embodiments of the invention, $R_2$ and $R_3$ are each independently an alkyl.

According to some embodiments of the invention, each of $R_2$ and $R_3$ is methyl.

According to some embodiments of the invention, $R_2$ and $R_3$ form together said ring.

According to some embodiments of the invention, said ring is a saturated 3-6-membered ring.

According to some embodiments of the invention, $R_4$ is selected from the group consisting of hydrogen and alkyl.

According to some embodiments of the invention, $R_5$ is alkyl.

According to some embodiments of the invention, $R_6$ is hydrogen and $R_7$ is selected from the group consisting of hydrogen and carbonyl.

According to some embodiments of the invention, $R_8$ is selected from the group consisting of hydrogen and alkyl.

According to some embodiments of the invention, $R_9$-$R_{12}$ are each hydrogen.

According to some embodiments of the invention, at least one of $R_9$-$R_{12}$ is halo.

According to some embodiments of the invention, the dipeptide analog comprises at least one halo group.

According to some embodiments of the invention, the dipeptide analog is characterized as inhibiting amyloid fibril formation.

According to some embodiments of the invention, the dipeptide analog is identified for use in the treatment of an amyloid-associated disease or disorder.

According to an aspect of some embodiments of the present invention there is provided a pharmaceutical composition comprising the peptide analog as described herein and a pharmaceutically acceptable carrier.

According to some embodiments of the invention, the pharmaceutical composition is being packaged in a packaging material and identified in print, in or on said packaging material, for use in the treatment of an amyloid-associated disease or disorder.

According to an aspect of some embodiments of the present invention there is provided a use of the dipeptide analog as described herein in the manufacture of a medicament for treating an amyloid-associated disease or disorder.

According to an aspect of some embodiments of the present invention there is provided a method of treating an amyloid-associated disease or disorder in a subject in need thereof, the method comprising administering to the subject a therapeutically effective amount of the dipeptide analog as described herein.

According to an aspect of some embodiments of the present invention there is provided a process of preparing the dipeptide analog as described herein, the process comprising coupling a tryptophane moiety, as described herein and a beta-sheet breaker moiety.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-C* present the chemical structures of exemplary beta-sheet breaker moieties according to some embodiments of the invention, wherein the moiety is coupled to a Trp moiety via the alpha-amine;

FIGS. 2A-J present the chemical structures of exemplary Trp moieties according to some embodiments of the invention, wherein the moiety is coupled to a beta-sheet breaker moiety via the alpha-carboxylate;

FIGS. 3A-Y present the chemical structures of exemplary dipeptide analogs according to some embodiments of the invention;

DESCRIPTION OF SPECIFIC EMBODIMENTS OF THE INVENTION

Figure 4:
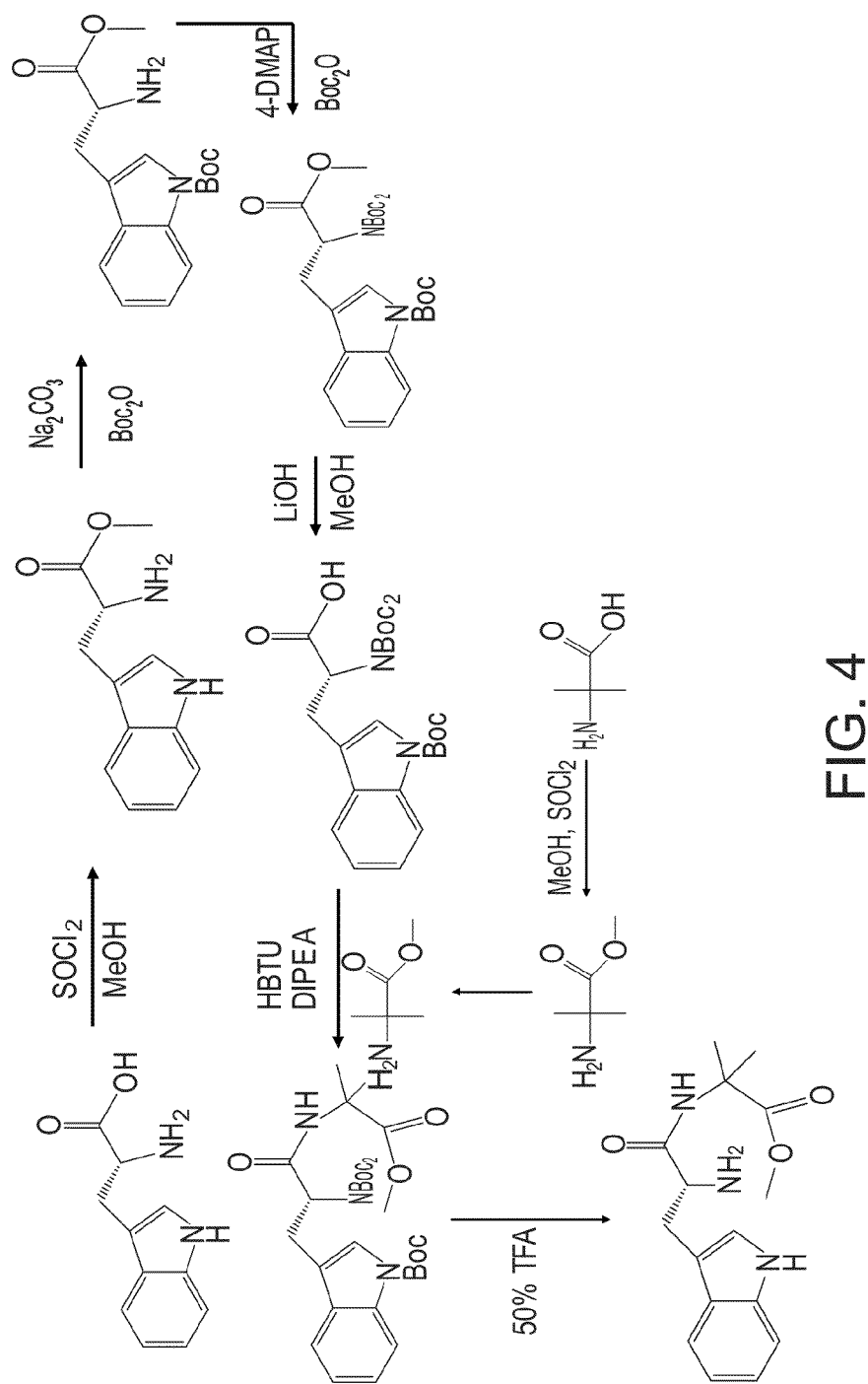
FIG. 4 is a schematic illustration of a synthetic pathway for preparing an exemplary dipeptide analog according to some embodiments of the invention.

The present invention, in some embodiments thereof, relates to novel therapeutic agents and, more particularly, but not exclusively, to dipeptides and analogs thereof, which inhibit amyloid fibril formation and thus can be used in the treatment of amyloid associated diseases, such as type II diabetes mellitus, Alzheimer's dementia or diseases, systemic and localized amyloidosis, ocular diseases and disorders and prion-related encephalopathies.

The dipeptides described herein are based on a previously described dipeptide D-Trp-Aib (also referred to herein and in the art as EG030), which incorporates an aromatic amino acid moiety (Trp) coupled to a beta-sheet breaker moiety (the unnatural amino acid Aib), and which has been defined as highly efficacious inhibitor of amyloid fibril formation. The dipeptides described herein are therefore small molecules that are considered as analogs of the D-Trp-Aib dipeptide, in which one or more of the aromatic amino acid moiety (Trp) and the beta-sheet breaker moiety are modified so as to impart to the analog improved performance as compared to D-Trp-Aib.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for novel therapeutic agents for preventing amyloid plaque formation, the present inventors have designed and successfully prepared and practiced dipeptides with improved performance. More specifically, the novel dipeptides were designed to exhibit improved pharmacokinetic characteristics, such as, for example, improved BBB permeability and improved inhibition activity of amyloid plaque formation, and optionally improved biostability (e.g., increased half-life), improved solubility, and the like.

While reducing the present invention to practice, the present inventors have identified some structural characteristics that impart to the dipeptide analog a desired pharmacokinetic profile. These include, for non-limiting examples, incorporation of a beta-sheet breaker moiety with increased stearic hindrance and/or increased lipophilicity (as compared to Aib); an aromatic moiety which incorporates a beta-sheet breaker moiety; and an aromatic moiety with increased lipophilicity and/or with functionalities that increase the half-life of the molecule.

Thus, according to an aspect of some embodiments of the present invention there is provided a dipeptide analog which comprises a tryptophan (Trp) moiety coupled to a beta-sheet breaker moiety.

As used herein, the phrase "tryptophan moiety" describes a chemical moiety that is derived from the amino acid tryptophan. The phrase "tryptophan moiety" encompasses tryptophan per se, as well as derivatives and structural analogs thereof.

The term "derivative" as used herein in the context of any of the described moieties, describes a moiety that has been modified so as to include a new chemical functionality (namely, a functionality not present in the moiety per se). Derivatization of a chemical moiety includes replacement of one functional group by another, addition of a functional group or omission of a functional group. By "functional group" it is meant, for example, a substituent other than hydrogen.

A "tryptophan derivative" thus includes, according to some embodiments of the invention, a tryptophan derivatized so as to include one or more substituents on the indole ring, a substituent on the indole nitrogen, a substituent on the alpha carbon, and one or more substituents on the alpha nitrogen. Other derivatives are also contemplated.

The term "analog" as used herein in the context of any of the described moieties, describes chemical moieties that have similar yet not identical structural features as the original moiety. An analog can therefore differ from the original moiety by a degree of saturation, a number of atoms in a ring, a type of heteroatom, a length of an alkylene chain, a configuration of a double bond, a configuration of one or more asymmetric carbons, and the like.

A "tryptophan analog" thus includes, according to some embodiments of the invention, an amino acid in which an indole moiety is linked to the alpha carbon directly, via an ethylene chain, or via a double bond, a tryptophan modified to include a heteroaromatic moiety other than indole, and a tryptophan modified to include a heterocyclic moiety, as defined herein, other than indole, as non-limiting examples.

As used herein, the phrase "beta-sheet breaker moiety" encompasses moieties that are derived from natural and non-natural amino acids, and which are characterized by a limited phi angle of about −60 to +25 rather than the typical beta sheet phi angle of about −120 to −140 degrees, thereby disrupting the beta sheet structure of the amyloid fibril.

An exemplary natural amino acid known as a beta-sheet breaker is proline. Other β-sheet breaker amino acids include, but are not limited to, aspartic acid, glutamic acid, glycine, lysine and serine (according to Chou and Fasman (1978) Annu. Rev. Biochem. 47, 258).

According to some embodiments of the invention, the β-sheet breaker moiety is a synthetic amino acid such as a Cα-methylated amino acid, which conformational constrains are restricted [Balaram, (1999) J. Pept. Res. 54, 195-199]. Unlike natural amino acids, which have a hydrogen atom attached to the $C_\alpha$, Cα-methylated amino acids have a methyl group attached to the $C_\alpha$, which affects widely their sterical properties regarding the $\phi$ and $\psi$ angles of the amide bond. Thus, while alanine has a wide range of allowed $\phi$ and $\psi$ conformations, α-aminoisobutyric acid (Aib, see Table 2, above) has limited $\phi$ and $\psi$ conformations.

In some embodiments, the beat-sheet breaker moiety is derived from alpha-aminoisobutyric acid (Aib), such that it is either Aib per se or a derivative or an analog of Aib, as defined herein.

A derivative of Aib includes, according to some embodiments of the invention, Aib derivatized to replace one or more of the methyl substituents at the C-alpha, to replace the alpha-carboxylic acid with e.g., an ester, an amide, an acyl chloride, a thiocarboxylate, etc., and to include a substituent on the alpha nitrogen. Other derivatives are also contemplated.

In some embodiments, the beat-sheet breaker moiety is an alpha-methylated amino acid, such as, for example, alpha-methyl-lysine, alpha-methyl-valine, and alpha-methyl-phenylalanine.

It is to be understood that when the indicated moieties are referred to in the context of the described dipeptide analogs, a portion of each moiety formed upon coupling to the other moiety is referred to. In this context, the term "moiety" is equivalent to the term "residue" as used in the context of amino acids in a peptide, such that it represents that portion of an amino acid or of an analog or a derivative thereof, that is present in the dipeptide upon being coupled to another amino acid (or a derivative or an analog thereof) via a peptide bond or an analogous bond.

Accordingly, a "dipeptide analog" as used herein, describes a peptide composed of residues of a Trp moiety and a beta-sheet breaker moiety, as defined herein, and encompasses any of the tryptophan moieties described herein, covalently linked to any of the beta-sheet breaker moieties as described herein, by means of forming a peptide bond between an amine group of one moiety and a carboxylic group of another moiety. The "dipeptide analog" can thus also be referred to as a chemical conjugate that comprises a tryptophan moiety covalently linked to an Aib moiety. The dipeptide analog is also referred to herein simply as a compound or a molecule.

Excluded from the scope of embodiments of the present invention is the dipeptide Trp-Aib, and an ester derivative thereof. Embodiments of the invention encompass, however, dipeptide analogs in which one of the moieties is Trp or Aib (including an ester thereof), provided that the other moiety is not Aib (or an ester thereof) or Trp, respectively.

The dipeptide analogs described herein can be collectively represented by the general Formula I:

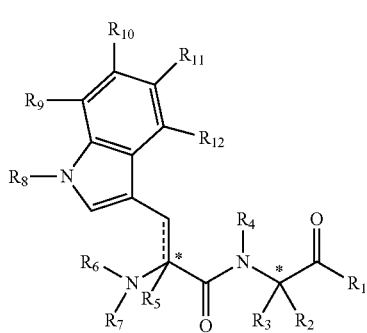

Formula I wherein:
the dashed line denotes an optional double bond;
* denotes either (R) configuration or (S) configuration (relevant for the carbon substituted by $NR_6R_7$ in case of a single bond, where the dashed line is absent);
$R_1$ is selected from the group consisting of hydrogen, alkyl, aryl, hydroxy, alkoxy, aryloxy, thiol, thioalkoxy, thioaryloxy, halo and amine;
$R_2$ and $R_3$ are each independently selected from the group consisting of alkyl, cycloalkyl, aryl, halo, haloalkyl and benzyl, or, alternatively, $R_2$ and $R_3$ form together a 3-8-membered saturated or unsaturated ring;
$R_4$ is selected from the group consisting of hydrogen, alkyl, cycloalkyl, aryl, carbonyl, thiocarbonyl, carboxylate and thiocarboxylate, or, alternatively, $R_4$ and $R_3$ form together a 4-8 membered saturated or unsaturated ring;
$R_5$ is selected from the group consisting of hydrogen and alkyl, or is absent in case the dashed line denotes a double bond;
$R_6$ and $R_7$ are each independently selected from the group consisting of hydrogen, alkyl, cycloalkyl, aryl, carbonyl, thiocarbonyl, carboxylate, and thiocarboxylate, or, alternatively, $R_6$ and $R_7$ form together a 4-8-membered saturated or unsaturated ring;
$R_8$ is selected from the group consisting of hydrogen, alkyl, cycloalkyl, aryl, carbonyl, thiocarbonyl, carboxylate and thiocarboxylate; and
$R_9$-$R_{12}$ are each independently selected from the group consisting of hydrogen, alkyl, cycloalkyl, aryl, alkoxy, thioalkoxy, aryloxy, thioaryloxy, halo, hydroxy, thiol, carbonyl, carboxylate and carbamate;
provided that when $R_2$ is alkyl and $R_3$ is methyl, at least one of $R_4$, $R_5$ and $R_8$-$R_{12}$ is not hydrogen.

In general Formula I, the fragment —($R_4$)—N—C($R_2$)($R_3$)—C(=O)—$R_1$ is considered as deriving from Aib moiety.

In some embodiments, $R_4$ is hydrogen, $R_2$ and $R_3$ are each methyl and $R_1$ is hydroxy, such that the dipeptide analog comprises amino-isobutyric acid (Aib) as the beta-sheet breaker moiety.

In some embodiments, the Aib moiety is derivatized so as to include other substituents on the alpha-carbon.

Thus, in some embodiments, at least one of $R_2$ and $R_3$ is an alkyl higher than methyl (namely, is being of more than one carbon atom).

In some embodiments, one or both of $R_2$ and $R_3$ is a bulky alkyl such as, but not limited to, isopropyl, isobutyl, tert-butyl, and the like.

As used herein and in the art the expression "bulky" with reference to a substituent or a certain group describes a chemical moiety that occupies a large volume. A bulkiness of a group is determined by the number and size of the atoms composing the group, by their arrangement, and by the interactions between the atoms (e.g., bond lengths, repulsive interactions). In the context of the present embodiments, bulky groups are groups that comprise 3 or more carbon atoms. Further in the context of the present embodiments, bulky alkyl groups encompass branched alkyls or substituted alkyls.

In some embodiments, one or both of $R_2$ and $R_3$ is an alkyl substituted by an aryl or a cycloalkyl, so as to form bulky substituent(s). The alkyl can be substituted by other groups that impart bulkiness. In exemplary embodiments, one or both of $R_2$ and $R_3$ is benzyl, in which the phenyl is substituted or unsubstituted.

In some embodiments, one of $R_2$ and $R_3$ is methyl and the other is a higher alkyl or a substituted alkyl, as described herein. Exemplary such beta-sheet breaker moieties include, but are not limited to, alpha-methylated amino acids such as α-Me-Valine, α-Me-Leucine, and α-Me-Phenylalanine.

In some embodiments, $R_2$ and $R_3$ form together a 3-8-membered saturated or unsaturated ring.

The ring can be alicyclic (cycloalkyl), heteroalicyclic, aromatic or heteroaromatic.

In some embodiments, $R_2$ and $R_3$ form together a saturated alicyclic 3-membered ring (cyclopropane), 4-membered ring (cyclobutane), 5-membered ring (cyclopentane), or 6-membered ring (cyclohexane).

Alternatively, $R_2$ and $R_3$ form together an unsaturated, non-aromatic ring (e.g., cyclopentene, cyclohexene).

Further alternatively, $R_2$ and $R_3$ form together a heteroalicyclic ring, as defined herein.

In some embodiments, $R_2$ and $R_3$ form together an oxetane, a tetrahydrofuran, a terahydropyrane, a dihydrofuran or a dihyropyrane.

In some embodiments, $R_2$ and $R_3$ form together an oxetane.

The ring formed by $R_2$ and $R_3$ can be substituted or unsubstituted, as defined herein.

As demonstrated in the Examples section that follows, it has been demonstrated that dipeptide analogs in which $R_2$ and $R_3$ represent groups with higher bulkiness as compared to the two corresponding methyl groups in Aib (e.g., dipeptide analogs in which $R_2$ and $R_3$ form together a ring) exhibit a superior inhibition activity as compared to the D-Trp-Aib dipeptide.

In some embodiments, $R_4$ is hydrogen, as in Aib.
In some embodiments, $R_4$ is other than hydrogen.
Thus, in some embodiments, $R_4$ is alkyl (e.g., methyl).
In some embodiments, $R_4$ and $R_3$ form together a ring, as described herein for $R_2$ and $R_3$. Such a ring can be substituted or unsubstituted heteroalicyclic or heteroaromatic ring, as defined herein.

In exemplary embodiments, when $R_4$ and $R_3$ form together said ring, $R_2$ is an alkyl.

In some embodiments, $R_4$ and $R_3$ form together a saturated 5-membered ring, such that the beta-sheet breaker moiety is α-Me-Proline.

In some embodiments, the beta-sheet breaker moiety comprises one or more halo groups (e.g., chloro, fluoro or bromo).

Without being bound by any particular theory, it is suggested that the presence of a halo group increases the lipophilicity and/or increases the half-life of the dipeptide analog, and thus imparts to the peptide analog improved pharmacokinetic characteristics.

A halo group can be introduced to the dipeptide analog as being one of $R_2$ and $R_3$, as a substituent of an alkyl, cycloalkyl or an aryl that form one or more of $R_2$, $R_3$, or $R_4$, or as a substituent of a ring formed by $R_2$ and $R_3$ and/or $R_3$ and $R_4$.

In some embodiments, one or more of $R_2$ and $R_3$ is a haloalkyl such as trihaloalkyl (e.g., trifluoromethyl). In an exemplary embodiment, the beta-sheet breaker moiety is amino trifluoroisobutiric acid.

In some embodiments, one or more of $R_2$ and $R_3$ is a halogenated benzyl. In an exemplary embodiment, the beta-sheet breaker moiety is a halogenated α-Me-Phenylalanine.

Each of the beta-sheet breaker moieties described herein can terminate by a carboxylic acid group, such that $R_1$ in Formula I is hydroxy.

However, the present inventors have demonstrated that derivatizing the carboxylic group so as to include an ester or an amide results in improved inhibition activity and may also impart the dipeptide analog with improved pharmacokinetic characteristics such as improved lipophilicity and BBB permeability.

Thus, in some embodiments, for any of the beta-sheet breaker moieties described herein, $R_1$ is alkoxy or amine.

In some embodiments, the alkoxy is a bulky group, as defined herein, such that the alkoxy is an O-alkyl group wherein the alkyl is a bulky alkyl, as defined herein. Representative examples include, but not limited to, t-butoxy, isopropoxy, and the like.

In some embodiments, when $R_1$ in formula I is amine, the amine can be a primary amine (—$NH_2$), a secondary amine (—NHR') or a tertiary amine (NR'R"), where R' and R" can each independently be alkyl, cycloalkyl or aryl, preferably each being independently an alkyl.

In some embodiments, $R_1$ is a secondary amine.

Referring now to the Trp moiety, presented in Formula I by the fragment not included in the —($R_4$)—N—C($R_2$)($R_3$)—C(=O)—$R_1$ fragment.

In some embodiments, the Trp moiety in the described dipeptide analog includes a beta-sheet breaker moiety, for example, in the form of a methyl substituent on the alpha-carbon, such that the Trp moiety is α-Me-tryptophan.

Accordingly, in some embodiments, $R_5$ is alkyl.

In some embodiments, $R_5$ is methyl.

In some embodiments, the alpha-amine of the Trp moiety is derivatized, such that at least one of $R_6$ and $R_7$ is other than hydrogen, and the alpha-amine is a secondary amine or tertiary amine.

A secondary or tertiary amine imparts to the dipeptide analog improved lipophilicity and BBB permeability.

In some embodiments, the alpha-amine of the Trp moiety is substituted by a carboxylate, carbonyl (including aldehyde), thiocarbonyl and/or thiocarboxylate, so as to form an amide or a carbamate.

In some embodiments, the alpha amine of the Trp moiety is substituted by t-BOC.

In some embodiments, $R_6$ and $R_7$ form together a heteroalicyclic or heteroaromatic ring, as described hereinabove for $R_4$ and $R_3$.

In some embodiments, the Trp moiety is such that the indole moiety is derivatized so as to include one or more substituents. In some embodiments, the N-indole is substituted, such that $R_8$ is other than hydrogen.

In some embodiments, $R_8$ is an alkyl (e.g., methyl).

In some embodiments, $R_8$ is a bulky alkyl (e.g., isopropyl, isobutyl or t-butyl).

In some embodiments, $R_8$ is t-butyl.

In some embodiments, the indole group is substituted by one or more substituents, denoted as $R_9$-$R_{12}$, as detailed hereinabove.

In some embodiments, one or more of $R_9$-$R_{12}$ is halo, as defined herein.

Without being bound by any particular theory, it is suggested that introducing one or more halo groups to the indole moiety provides for improved pharmacokinetic characteristics as a result of improved lipophilicity and/or prolonged half-life.

Since one of the main obstacles in using short peptide fragments in therapy is their proteolytic degradation by stereospecific cellular proteases, in some embodiments, one or both optional asymmetric carbons (marked by * in Formula I) are derived from D-isomers of the indicated amino acid moieties, and accordingly has an (R) configuration.

In some embodiments the alpha-carbon of the Trp-moiety is an asymmetric carbon that has an (R) configuration.

In some embodiments, an indole group, as described herein, is attached to the alpha carbon via a double bond.

It is to be noted that the number and nature of the modifications introduced to the dipeptide analog is governed by stearic and electronic considerations that may affect both the stability of the obtained product and the feasibility of its synthesis.

Accordingly, in some embodiments, the dipeptide analogs are such that do not contain two or more bulky groups in close proximity to one another or two or more electronegative groups in close proximity to one another.

As used herein, the term "amine" describes both a —NR'R" group and a —NR'— group, wherein R' and R" are each independently hydrogen, alkyl, cycloalkyl, aryl, as these terms are defined herein.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms. In some embodiments, unless otherwise indicated, the alkyl is a lower alkyl having 1 to 6 or 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, oxetane, tetrahydrofurane, tetrahydropyrane, morpholino and the like.

The term "halo" is also referred to herein as "halide" and describes fluorine, chlorine, bromine or iodine.

The term "haloalkyl" describes an alkyl group as defined above, further substituted by one or more halide. A "trihaloalkyl" describes, for example, a trihaloalkyl (e.g., —$CX_3$, where X is halide).

The term "carbonyl" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "hydroxyl" or "hydroxy" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" or "thiol" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —$NO_2$ group.

The term "acyl halide" describes a —(C=O)R'''' group wherein R''' is halide, as defined hereinabove.

The term "carboxylate" encompasses C-carboxylate, O-carboxylate, C-thiocarboxylate, and O-thiocarboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "amide" encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "azo" or "diazo" describes an —N=NR' end group or an —N=N— linking group, as these phrases are defined hereinabove, with R' as defined hereinabove.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "phosphonate" describes a —P(=O)(OR')(OR") end group or a —P(=O)(OR')(O)— linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "phosphinyl" describes a —PR'R" end group or a —PR'— linking group, as these phrases are defined hereinabove, with R' and R" as defined hereinabove.

The term "phosphine oxide" describes a —P(=O)(R')(R") end group or a —P(=O)(R')— linking group, as these phrases are defined hereinabove, with R' and R" as defined herein.

The term "phosphine sulfide" describes a —P(=S)(R')(R") end group or a —P(=S)(R')— linking group, as these phrases are defined hereinabove, with R' and R" as defined herein.

The term "phosphite" describes an —O—PR'(=O)(OR") end group or an —O—PH(=O)(O)— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R'" end group or a —R'NC(=N)—NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

A list of non-limiting examples of beta-sheet breaker moieties that are suitable for use in the context of embodiments of the invention is presented in Table 3 (see, Example 1, that follows) and in FIG. 1.

A list of non-limiting examples of Trp moieties that are suitable for use in the context of embodiments of the invention is presented in Table 2 (see, Example 1, that follows) and in FIG. 2.

It is to be noted that embodiments of the present invention encompass any combination of one of the Trp moieties described herein and one of the beta-sheet breaker moieties described herein.

A list of non-limiting examples of dipeptide analogs according to some embodiments of the invention is presented in Table 1 (see, Example 1 that follows).

A list of non-limiting examples dipeptide analogs according to some embodiments of the invention is also presented in FIG. 3.

As noted hereinabove and is further demonstrated in the Examples section that follows, the present inventors have uncovered that modifications of some structural and functional features of a Trp moiety and/or an Aib moiety in a dipeptide composed of these two moieties, result in dipeptide analogs of the previously described D-Trp-Aib that are characterized by an improved performance and hence can be efficiently utilized as therapeutic agents for inhibiting amyloid fibril formation.

Accordingly, in some embodiments, a dipeptide analog as described herein is characterized by an improved performance as compared to D-Trp-Aib and previously described derivatives thereof.

In some embodiments, a dipeptide analog as described herein is characterized by amyloid fibril formation inhibitory activity that is greater than such an inhibitory activity of D-Trp-Aib. In some embodiments, an enhanced inhibitory activity of the dipeptide analogs described herein is measured by the minimal amyloid-beta protein:inhibitor ratio required for inhibiting the formation of globulomers of the amyloid-beta protein. In some embodiments, the dipeptide analogs described herein exhibit substantially complete inhibition of the formation of globulomers of the amyloid-beta protein at a 1:20 amyloid-beta protein:inhibitor molar ratio. Such a ratio is 2-folds lower that the corresponding minimal amyloid-beta protein:inhibitor ratio required for inhibiting the formation of globulomers of the amyloid-beta protein of D-Trp-Aib, and indicates a substantially improved inhibitory activity of the dipeptide analogs described herein.

In some embodiments, the dipeptide analogs described herein exhibit substantially complete inhibition of the formation of globulomers of the amyloid-beta protein at a 1:10 amyloid-beta protein:inhibitor molar ratio. In some embodiments, the dipeptide analogs described herein exhibit substantially complete inhibition of the formation of globulomers of the amyloid-beta protein at a 1:1 amyloid-beta protein:inhibitor molar ratio and even at lower ratios.

In some embodiments, a dipeptide analog as described herein is characterized by BBB permeability that is greater than a BBB permeability of D-Trp-Aib. In some embodiments, a dipeptide analog as described herein is characterized by lipophilicity that is greater than a lipophilicity of D-Trp-Aib.

In some embodiments, a dipeptide analog as described herein is characterized by half-life that is greater than a half-life of D-Trp-Aib.

Altogether, a dipeptide analog as described herein is characterized by an improved therapeutic effect as compared to the previously described D-Trp-Aib and ester derivatives thereof. Such an improved effect can be manifested by a reduced amount of the dipeptide analog required to treat an indicated condition, as is detailed hereinbelow, by reduced number of administrations of the dipeptide analog, as compared to D-Trp-Aib, and/or by reduced side effects.

Accordingly, according to some embodiments of the invention, each of the dipeptide analogs described herein is independently characterized as an inhibitor of amyloid fibril formation.

According to some embodiments, each of the dipeptide analogs described herein is independently identified for use in the treatment of an amyloid-associated disease or disorder.

According to an aspect of some embodiments of the invention there is provided a use of any of the dipeptide analogs described herein in the manufacture of a medicament for treating an amyloid-associated disease or disorder.

According to an aspect of some embodiments of the invention there is provided a method of treating an amyloid-associated disease or disorder in a subject in need thereof, the method comprising administering to the subject a therapeutically effective amount of a dipeptide analog as described herein.

Preferred individual subjects according to embodiments of the present invention are mammals such as canines, felines, ovines, porcines, equines, bovines, humans and the like.

As used herein throughout, the phrases "inhibiting (or preventing) amyloid fibril formation", "inhibiting (or preventing) amyloid plaque formation", "disaggregating amyloid fibrils", "inhibiting (or preventing) amyloid-beta globulomerization", as well as grammatical diversions and combinations thereof, are used interchangeably, and generally relate to interference with biological processes that result in aggregation of amyloid beta peptides into oligomers and polymers, thus forming an amyloid plaque. These phrases thus describe an activity of the described peptide analogs that results in reducing or preventing amyloid plaque formation, or substantially decreasing plaque occurrence in the affected tissue.

The phrase "amyloid plaque" refers to fibrillar amyloid as well as aggregated but not fibrillar amyloid, hereinafter "protofibrillar amyloid", which may be pathogenic as well.

It will be appreciated that when utilized for treatment of amyloid diseases, the dipeptide analogs described herein are capable of preventing fibril formation, reducing fibril formation, or disaggregating formed aggregates by competitive destabilization of the preformed aggregate. Alternatively, the described dipeptide analogs can act by self-aggregation and formation of heteromolecular complexes which are not as ordered as the homomolecular assemblies formed by amyloid fragments.

The phrase "amyloid-associated disease or disorder", as used herein, describe a medical condition with a pathology that involves amyloid plaque formation. Such a medical condition can involve other pathologies, yet, is treatable, at least to some extent, by reducing, preventing or inhibiting amyloid plaque formation.

Examples of amyloid-associated diseases treatable according to embodiments of the present invention include, but are not limited to, type II diabetes mellitus, Alzheimer's disease (AD), early onset Alzheimer's disease, late onset Alzheimer's disease, presymptomatic Alzheimer's disease, Perkinson's disease, SAA amyloidosis, hereditary Icelandic syndrome, multiple myeloma, medullary carcinoma, aortic medical amyloid, Insulin injection amyloidosis, prion-systematic amyloidosis, choronic inflammation amyloidosis, Huntington's disease, senile systemic amyloidosis, pituitary gland amyloidosis, Hereditary renal amyloidosis, familial British dementia, Finnish hereditary amyloidosis, familial non-neuropathic amyloidosis [Gazit (2002) Curr. Med. Chem. 9:1667-1675], amyloid-related ocular diseases and disorders such as glaucoma [Guo et al., *PNAS* (2007), 104(33), pp. 13444-13449] and age-related macular degeneration (AMD), and prion diseases including scrapie of sheep and goats and bovine spongiform encephalopathy (BSE) of cattle [Wilesmith and Wells (1991) Curr Top Microbiol Immunol 172: 21-38] and human prion diseases including (i) kuru, (ii) Creutzfeldt-Jakob Disease (CJD), (iii) Gerstmann-Streussler-Sheinker Disease (GSS), and (iv) fatal familial insomnia (FFI) [Gajdusek (1977) Science 197: 943-960; Medori, Tritschler et al. (1992) N Engl J Med 326: 444-449].

In any of the methods and uses described herein, a therapeutically effective amount, as defined herein, of the dipeptide analog is provided to the subject. The dipeptide analog can be provided using any one of a variety of delivery methods. Delivery methods and suitable formulations are described hereinbelow with respect to pharmaceutical compositions.

Suitable routes of administration may, for example, include oral, sublingual, inhalation, rectal, transmucosal, transdermal, intracavemosal, topical, intestinal or parenteral delivery, including intramuscular, subcutaneous and intramedullary injections as well as intrathecal, direct intraventricular, intravenous, intraperitoneal, intranasal, or intraocular injections.

The dipeptide analogs described herein can be provided to an individual subject per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the dipeptide analog, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

Formulations for topical administration include but are not limited to lotions, ointments, gels, creams, suppositories, drops, liquids, sprays and powders. Conventional carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

Pharmaceutical compositions suitable for use in context of the present embodiments include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the dipeptide analog as described herein, formulated in a compatible pharmaceutical carrier may also be prepared, placed in an appropriate container, and labeled for treatment of an indicated condition, as described herein.

The compositions may, if desired, be presented in a pack or dispenser device, such as an FDA (the U.S. Food and Drug Administration) approved kit, which may contain the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert.

In some embodiments, the pharmaceutical composition is packaged in a packaging material and identified in print, in or on the packaging material, for use in the treatment of an amyloid-associated disease or disorder, as described herein.

It will be appreciated that treatment of amyloid-associated diseases according to the present invention may be combined with other treatment methods known in the art (i.e., combination therapy). Thus, compounds according to embodiments of the present invention may be co-administered (simultaneously or separately) with additional anti-amyloid drugs. Examples of such anti-amyloid drugs include, but are not limited to, amyloid-destabilizing antibodies, amyloid-destabilizing peptides and anti-amyloid small molecules (further details on such drugs are provided in the preceding Background section). Compounds according to embodiments of the present invention may be co-administered (simultaneously or separately) with additional anti-drugs for treating an indicated disease or disorder.

Further according to an aspect of embodiments of the present invention, there is provided a process of preparing the dipeptide analogs described herein, which is effected by coupling a tryptophane moiety and a beta-sheet breaker moiety.

In some embodiments, the process is effected in the presence of a peptide coupling agent. Any coupling agents suitable for use for coupling amino acids are contemplated.

In some embodiments, the process further comprises, prior to the coupling, protecting one or more functional groups of either or both the tryptophane moiety and the beta-sheet breaker moiety. Any suitable protecting group is contemplated. Suitable protecting groups are typically selected as suitable for the functional to be protected and as being readily removed under conditions that do not affect other functionalities in the final dipeptide product or any intermediate thereof.

In case where protected Trp moiety and/or protected beta-sheet breaker moiety are used, the process further comprises, subsequent to the coupling, removing the protecting group(s). In case more than one protecting group is present in the coupled dipeptide, removal of the protecting groups can be performed simultaneously or sequentially, depending on the protecting groups used.

Selecting, and practicing the disclosed process with, suitable protecting groups is well recognized by those skilled in the art.

In some embodiments, the process further comprises, either prior to or subsequent to the coupling, preparing the tryptophane moiety and/or the beta-sheet breaker moiety of the dipeptide analog.

Accordingly, in some embodiments, Trp is coupled to a beta-sheet breaker moiety as described herein, to thereby provide a dipeptide analog with comprises Trp as the Trp moiety, and subsequently, the Trp in this dipeptide analog is derivatized so as to produce a dipeptide analog with a Trp moiety, as described herein for dipeptide analogs that comprises a Trp moiety different from Trp.

In some embodiments, a Trp moiety, as described herein, already modified as described herein, is first prepared and is then coupled to the beta-sheet breaker.

Similarly, in some embodiments, Aib is coupled to a Trp moiety, to thereby provide a dipeptide analog with Aib as the beta-sheet breaker moiety, and subsequently, the Aib in this dipeptide analog is derivatized so as to produce a dipeptide analog with a beta-sheet breaker moiety, as described herein for dipeptide analogs that comprises a beta-sheet breaker moiety different from Aib or an ester thereof.

An exemplary general procedure for preparing the described dipeptide analogs is presented in the Examples section that follows.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or to "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Chemical Syntheses

Materials and Methods:

Chemical reagents were purchased from Sigma-Aldrich, unless otherwise indicated.

Solvents were purchased from Bio-Lab, unless otherwise indicated.

NMR measurements were performed on a Bruker AVANCE-200 MHz NMR, using $SiMe_4$ as standard.

Electrospray Mass Spectroscopy (ESI-MS) measurements were performed on Waters Micromass SYNAPT HDMS Mass spectrometer.

General Procedure:

The dipeptide compounds described herein are prepared using a standard procedure for coupling two amino-acids, as follows:

D-Trp or an analog thereof (e.g., D/L-α-methyl-Trp) is coupled to a beta-sheet breaker moiety derived from the unnatural amino acid 2-amino-isobutiric acid (Aib).

Protection of the Carboxylic Function:

Amino acids are protected in their carboxylic function via a methyl-, ethyl- or tert-butyl-ester using thionyl chloride as reagent and either methanol, ethanol, or tert-butanol as solvent, based on the procedure described in *Bioorganic & medicinal chemistry* 15(14):4903-9, 2007, with the following changes: Thionyl chloride was not distilled prior to reaction; and the intermediate product was not purified via recrystallization but rather using a silica-gel 60 column, with ethyl acetate in hexane as eluent. The intermediate product is verified by 200 MHz $^1$H-NMR using $CDCl_3$ as solvent.

N-Boc Protection:

N-Boc protection of the tryptophan moiety (e.g., D-Trp-methyl-ester or D/L-alpha-methyl-Trp-methyl-ester) is performed according to the procedure described in J. Org. Chem. 71, 7106-9, 2006. The intermediate product is purified using silica-gel 60 column using 20%-50% ethyl acetate in hexane as eluent. The product is verified by 200 MHz $^1$H-NMR using $CDCl_3$ as solvent.

De-Esterification of Boc-Protected Amino Acid:

De-esterification of Boc-protected Trp moiety (e.g., D-Trp-methyl-ester or D/L-alpha-methyl-Trp-methyl-ester) is carried out using lithium hydroxide as follows:

The protected amino acid is dissolved in two volumes of methanol and cooled in an ice bath. Three equivalents of lithium hydroxide are dissolved in one volume of water and added to the solution, and the mixture is stirred at room temperature for a time period ranging from 2 hours to overnight, while being monitored by TLC. The obtained product is purified using silica gel 60 column using 1% acetic acid in ethyl acetate, as eluent. The product is verified via 200 MHz $^1$H-NMR using $CDCl_3$ as solvent.

Coupling:

Coupling of Boc-protected Trp moiety (e.g., D-Trp or D/L-alpha-Methyl-Trp) is performed using HBTU as a coupling reagent, DIEA as a catalyst and DMF as solvent, according to the procedure described in *J. Med. Chem.* 48 (22), 6908-6917, 2005. Coupling can also be effected using other coupling agents. The product is purified via silica-gel column, using 20%-50% ethyl acetate in hexane as eluent. The product structure is verified by 200 MHz $^1$H-NMR using $CDCl_3$ or DMSO-$d_6$ as solvent.

Boc Deprotection:

Boc deprotection is carried out using 50% TFA in methylene chloride for 6 minutes, followed by evaporation under reduced pressure. In order to remove remnants of TFA, addition of benzene and evaporation under reduced pressure is performed repetitively 2-3 times. Water is thereafter added and the pH of the solution is neutralized. Water is then removed by evaporation under reduced pressure followed by overnight lyophilization. The product is verified by 200 MHz $^1$H-NMR using $d_6$-DMSO as solvent.

Optional additional de-esterification is then performed, if desired, using the procedure described hereinabove. The final product is purified on a silica-gel column, using 1% acetic acid in ethanol as eluent. The product is verified by 200 MHz $^1$H-NMR using $d_6$-DMSO as solvent.

An exemplary synthetic scheme, depicting the synthesis of a $H_2N$-Trp-Aib-OMe, for illustrative purposes, is presented in FIG. 4.

Using the general procedure described hereinabove, the following exemplary dipeptide compounds were synthesized, as follows:

Preparation of $H_2N$-Trp-Aib-OtBu ((R)-(tert-butyl 2-(2-amino-3-(1H-indol-3-yl)propanamido)-2-methylpropanoate; Compound 1)

Compound 1 was prepared by coupling D-Trp and Aib-OtBu as described hereinabove.

$^1$H-NMR (200 MHz; DMSO-$d_6$): δ=1.22 (bs, 9H, —$(CH_3)_3$) 1.58 (bs, 6H, $(CH_3)_2$), 3.09-3.45 (m, 1H, CH & 2H, $CH_2$), 7.01-7.14 (m, 3H, Ar—CH), 7.37 (d, 1H, Ar—CH), 7.71 (d, 1H, Ar—CH), 8.07 (bs, 2H, amide-NH), 10.97 (bs, 1H, indol-NH).

MS (ESI): m/z=344.2 ($M^+$–$H^+$), 10%.

Preparation of (D/L)-H₂N-α-Me-Trp-Aib-OMe (methyl 2-(2-amino-3-(1H-indol-3-yl)-2-methylpropanamido)-2-methylpropanoate; Compound 2)

Compound 2 was prepared by coupling L/D-α-Me-Trp (racemic mixture) and Aib-OMe as described hereinabove.
¹H-NMR (200 MHz; DMSO-d₆): δ=1.38-1.48 (m, 9H, CH₃&CH₃)₂), 3.05-3.39 (m, 2H, CH₂), 3.66 (s, 3H, CH₃), 3.85 (m, 1H, CH), 7.08-7.77 (m, 5H, Ar—CH), 11.13 (bs, 1H, indol-NH);
MS (ESI): m/z=337.2 (M⁺+Li⁺) 100%.

Preparation of (D/L)-H₂N-α-Me-Trp-cyclopentane-OMe (methyl 1-(2-amino-3-(1H-indol-3-yl)-2-methylpropanamido)cyclopentanecarboxylate; Compound 3

Compound 3 was prepared by coupling L/D-α-Me-Trp and methyl 1-aminocyclopentanecarboxylate as described hereinabove.
¹H-NMR (200 MHz; CDCl₃): δ=0.83-1.79 (m, 11H, CH₃& 4CH₂), 3.18-3.58 (m, 2H, CH₂), 3.89 (s, 3H, CH₃), 4.3 (bs, 2H, NH₂), 6.91-7.57 (m, 5H, Ar—CH), 7.67 (bs, 1H, amide-NH);
MS (ESI): m/z=345.0 (M⁺+2H⁺) 10%.

Preparation of H₂N-Trp-cyclopentane-OH ((R)-1-(2-amino-3-(1H-indol-3-yl)propanamido)cyclopentanecarboxylic acid; Compound 4)

Compound 4 was prepared by coupling D-Trp and 1-aminocyclopentanecarboxylic acid as described hereinabove.
¹H-NMR (200 MHz; CDCl₃): δ=1.51-1.58 (m, 4H, CH₂), 1.90-2.25 (m, 4H, 2CH₂), 3.39-3.6 (m, 2H, CH₂), 4.12 (m, 1H, CH), 7.24-7.75 (m, 5H, Ar—CH), 8.1 (bs, 1H, amide-NH);
MS (ESI): m/z=346.2 (M⁺NaCl) 100%.

Preparation of H₂N-Trp-cyclopropane-OH ((R)-(1-(2-amino-3-(1H-indol-3-yl)propanamido)cyclopropanecarboxylic acid; Compound 5)

Compound 5 was prepared by coupling D-Trp and 1-aminocyclopropanecarboxylic acid as described hereinabove.
¹H-NMR (200 MHz; DMSO-d₆): δ=1.33-1.90 (m, 4H, CH₂), 3.25-3.62 (m, 2H, CH₂), 4.22 (m, 1H, CH), 7.07-8.17 (m, 6H, Ar—CH&1H, amide NH);
MS (ESI): m/z=346.2 (M⁺+NaCl) 100%.

Preparation of H₂N-Trp-cyclopropane-OEt ((ethyl 1-(2-amino-3-(1H-indol-3-yl)propanamido)cyclopropanecarboxylate); Compound 6)

Compound 6 was prepared by coupling D-Trp and ethyl 1-aminocyclopropanecarboxylate as described hereinabove.
¹H-NMR (200 MHz; CDCl₃): δ=1.15-1.52 (m, 7H, 2CH₂ & Et-CH₃), 2.96-3.52 (m, 2H, CH₂), 4.24 (q, 2H), 4.56-4.66 (m, 1H, CH), 6.96-7.59 (m, 5H, Ar—CH), 7.72-8.0 (bs, 1H, amide NH);
MS, ESI, MS (ESI): m/z=351.1 (M⁺+K⁺) 100%.

Preparation of H₂N-Trp-cyclohexane-OH (1-(2-amino-3-(1H-indol-3-yl)propanamido)cyclohexanecarboxylic acid; Compound 7)

Compound 7 was prepared by coupling D-Trp and 1-aminocyclohexanecarboxylic acid as described hereinabove.
¹H-NMR (200 MHz; CDCl₃): δ=0.76-0.92 (m, 6H, 3CH₂), 1.29-1.56 (m, 4H, 2CH₂), 3.03-3.55 (m, 2H, CH₂), 3.89 (m, 1H, CH), 7.02-7.62 (5H, Ar—CH), 7.88 (bs, 1H, amide NH);
MS (ESI): m/z=346.2 (M⁺+H₂O) 100%.

Preparation of H₂N-Trp-cyclohexane-OEt ((ethyl 1-(2-amino-3-(1H-indol-3-yl)propanamido)cyclohexanecarboxylate; Compound 8)

Compound 8 was prepared by coupling D-Trp and ethyl 1-aminocyclohexanecarboxylate as described hereinabove.
¹H-NMR (200 MHz; DMSO-d₆): δ=0.90-2.01 (m, 13H, Et-CH₃&5CH₂), 3.04-3.43 (m, 2H, CH₂), 4.01 (q, 2H), 6.99-8.10 (m, 5H, Ar—CH), 10.94 (bs, 1H, indol-NH);
MS (ESI): m/z=413.3 (M⁺+NaCl) 100%.

Preparation of H₂N-Trp-α-Me-Proline-OMe (methyl 1-(2-amino-3-(1H-indol-3-yl)propanoyl)-2-methylpyrrolidine-2-carboxylate; Compound 9)

Compound 9 was prepared by coupling D-Trp and α-Me-Proline-OMe as described hereinabove.
¹H-NMR (200 MHz; CDCl₃): δ=1.27-1.70 (m, 7H, CH₃&2CH₂), 3.22 (m, 3H, CH₂), 3.51-3.81 (m, 2H, CH₂), 4.7 (m, 1H, CH), 7.23-7.70 (m, 5H, Ar—CH);
MS (ESI): m/z=395.1 (M⁺+2Na⁺&+Cl⁻) 100%.

Preparation of H₂N-Trp-oxetane-OH ((R)-3-(2-amino-3-(1H-indol-3-yl)propanamido)oxetane-3-carboxylic acid; Compound 10)

Compound 10 was prepared by coupling D-Trp and 1-aminooxetanecarboxylic acid as described hereinabove.

Preparation of H₂N-Trp-oxetane-NH₂ ((R)-3-(2-amino-3-(1H-indol-3-yl)propanamido)oxetane-3-carboxamide; Compound 11)

Compound 11 was prepared by coupling D-Trp and 1-aminooxetanecarboxamide as described hereinabove.
The chemical structures of the described conjugates are presented in Table 1 below.

TABLE 1

| | Compound (Non-Systematic and IUPAC) | Chemical Structure |
|---|---|---|
| 1 | H₂N-Trp-Aib-OtBu (R)-(tert-butyl 2-(2-amino-3-(1H-indol-3-yl)propanamido)-2-methylpropanoate) | 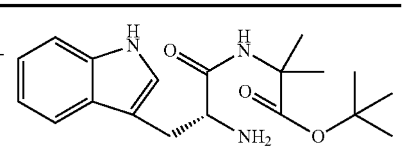 |

TABLE 1-continued

| | Compound (Non-Systematic and IUPAC) | Chemical Structure |
|---|---|---|
| 2 | (D/L)-H$_2$N-α-Me-Trp-Aib-OMe (methyl 2-(2-amino-3-(1H-indol-3-yl)-2-methylpropanamido)-2-methylpropanoate) | 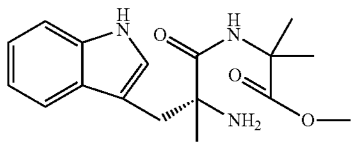 [SMILES: COC(=O)C(C)(C)NC(=O)[C@](C)(N)Cc1c[nH]c2ccccc12] |
| 3 | (D/L)-H$_2$N-α-Me-Trp-cyclopentane-OMe (methyl 1-(2-amino-3-(1H-indol-3-yl)-2-methylpropanamido)cyclopentane carboxylate) | 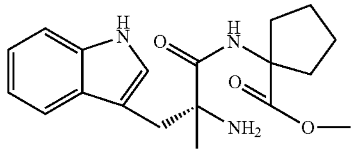 [SMILES: COC(=O)C1(NC(=O)[C@](C)(N)Cc2c[nH]c3ccccc23)CCCC1] |
| 4 | H$_2$N-Trp-cyclopentane-OH (R)-1-(2-amino-3-(1H-indol-3-yl)propanamido)cyclopentane-carboxylic acid | 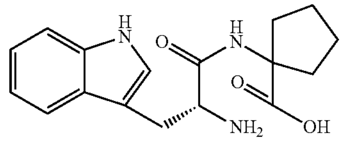 [SMILES: N[C@H](Cc1c[nH]c2ccccc12)C(=O)NC1(C(=O)O)CCCC1] |
| 5 | H$_2$N-Trp-cyclopropane-OH (R)-(1-(2-amino-3-(1H-indol-3-yl)propanamido)cyclopropane-carboxylic acid) | 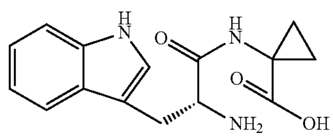 [SMILES: N[C@H](Cc1c[nH]c2ccccc12)C(=O)NC1(C(=O)O)CC1] |
| 6 | H$_2$N-Trp-cyclopropane-OEt (ethyl 1-(2-amino-3-(1H-indol-3-yl)propanamido)cyclopropane-carboxylate) | 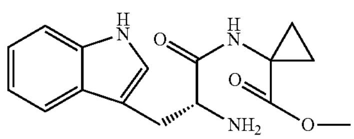 [SMILES: COC(=O)C1(NC(=O)[C@H](N)Cc2c[nH]c3ccccc23)CC1] |
| 7 | H$_2$N-Trp-cyclohexane-OH 1-(2-amino-3-(1H-indol-3-yl)propanamido)cyclohexane carboxylic acid | 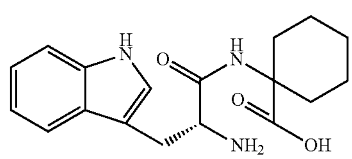 [SMILES: N[C@H](Cc1c[nH]c2ccccc12)C(=O)NC1(C(=O)O)CCCCC1] |
| 8 | H$_2$N-Trp-cyclohexane-OEt ethyl 1-(2-amino-3-(1H-indol-3-yl)propanamido)cyclohexane carboxylate | 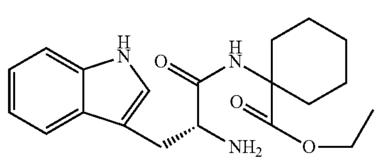 [SMILES: CCOC(=O)C1(NC(=O)[C@H](N)Cc2c[nH]c3ccccc23)CCCCC1] |
| 9 | H$_2$N-Trp-α-Me-Proline-OMe methyl 1-(2-amino-3-(1H-indol-3-yl)propanoyl)-2-methylpyrrolidine-2-carboxylate | 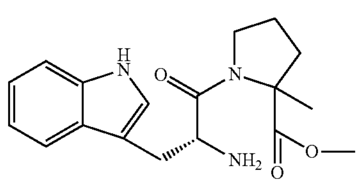 [SMILES: COC(=O)C1(C)CCCN1C(=O)[C@H](N)Cc1c[nH]c2ccccc12] |
| 10 | H$_2$N-Trp-oxetane-OH (R)-3-(2-amino-3-(1H-indol-3-yl)propanamido)oxetane-3-carboxylic acid | 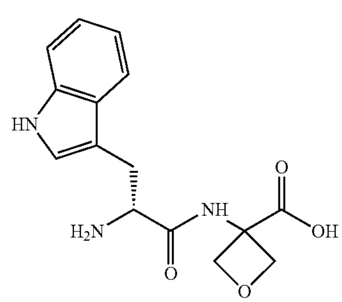 [SMILES: N[C@H](Cc1c[nH]c2ccccc12)C(=O)NC1(C(=O)O)COC1] |

TABLE 1-continued

| Compound (Non-Systematic and IUPAC) | Chemical Structure |
| --- | --- |
| 11 H₂N-Trp-oxetane-NH₂ (R)-3-(2-amino-3-(1H-indol-3-yl)propanamido)oxetane-3-carboxamide | |

It is to be noted that while in Table 1 the chemical structures are presented for D-Trp moieties, conjugates comprising a corresponding L-Trp moiety are also contemplated.

Using the above-described general procedure, compounds comprising a Trp moiety as depicted in Table 2 below are prepared:

TABLE 2

| Tryptophan analogs | |
| --- | --- |
| Name | Structure |
| Tryptophan | |
| α-Me-Tryptophan | |
| N-methyl-Tryptophan | |
| N-t-butyl-Tryptophan | |
| 4-halogenated-Tryptophan | |
| 5-halogenated-Tryptophan | |
| 6-halogenated-Tryptophan | |

Each of the Trp moieties depicted in Table 2 is coupled to one of the beta sheet breaker moieties depicted in Table 3 below.

TABLE 3

| Aib analogs | |
| --- | --- |
| Name | Structure |
| Amino-cyclopropane-carboxylic acid | |
| Amino-oxetane-carboxylic acid | |
| Amino-oxetane-carboxamide | |

TABLE 3-continued

Aib analogs

| Name | Structure |
|---|---|
| Amino-cyclopentane-carboxylic acid | 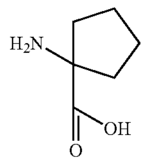 |
| Amino-cyclohexane-carboxylic acid | 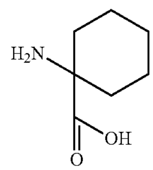 |
| α-Me-Proline | 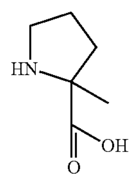 |
| α-Me-Valine | 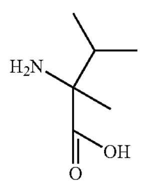 |
| α-Me-Leucine | 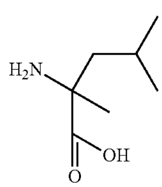 |
| α-Me-Phenyl | 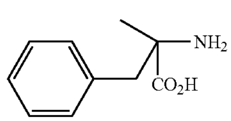 |
| α-Me-halogenated-Phenyl | 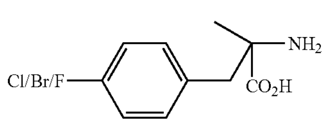 |
| Trifluoro-amino-isobutiric acid | 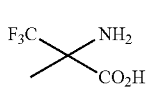 |

Further using the general procedure described herein above, the following compounds were prepared as follows:

Preparation of Compound A

FIG. 3

Compound A was prepared as depicted in Scheme 1 below.

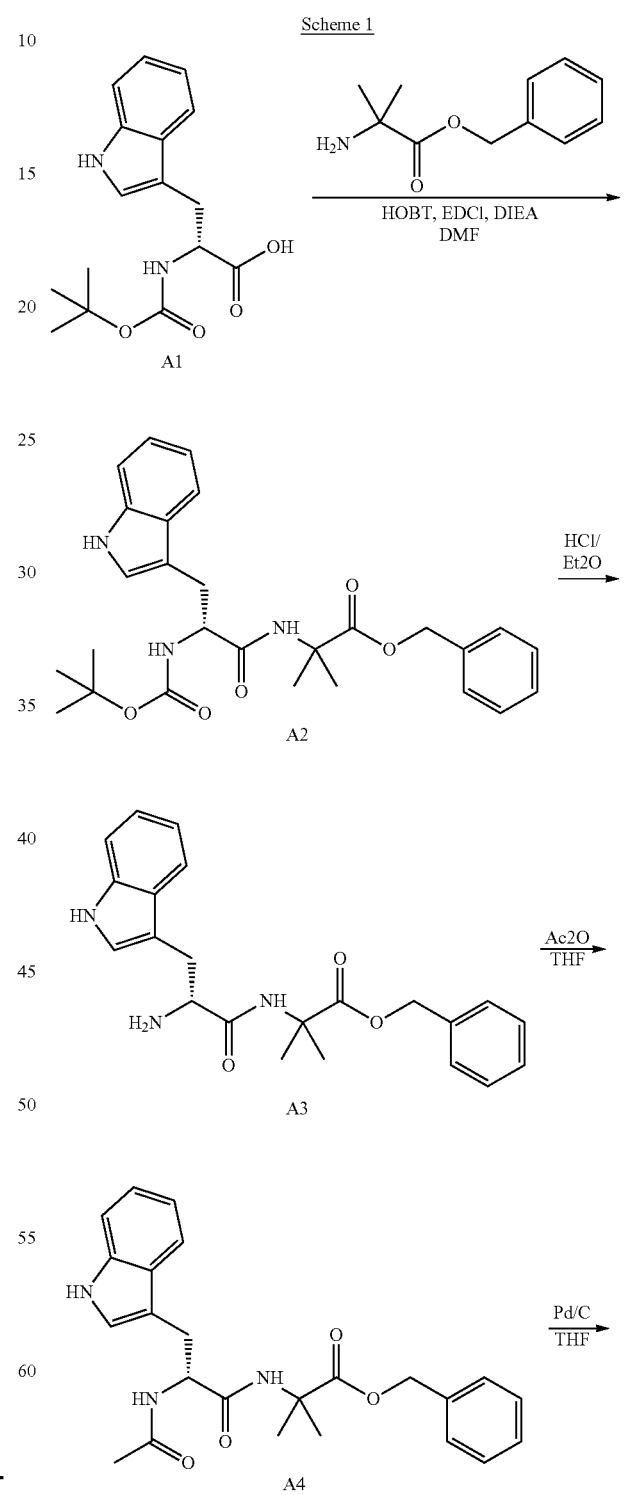

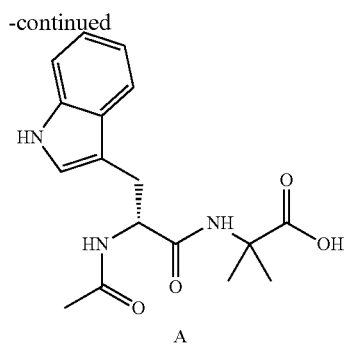

A

Preparation of Compound A2

To a stirred solution of compound A1 (5.10 grams, 16.7 mmol) and phenylmethyl-2-amino-2-methylpropanoate HCl salt (3.60 grams, 18.4 mmol) in DMF (100 ml) was added HOBT (3.40 grams, 25.1 mmol), DIEA (8.9 ml, 50.1 mmol) and EDCI (4.50 grams, 25.1 mmol) at room temperature. After stirring for 16 hours at room temperature under $N_2$ atmosphere, the mixture was poured into ice/water (100 ml) and was extracted with EtOAc (100 ml×2). The organic phase was washed with 1N HCl aqueous solution (80 ml×2), saturated $NaHCO_3$ solution (80 ml×2), brine (80 ml) and dried over $Na_2SO_4$. Then, the EtOAc solvent was removed in vacuo. The residue was purified by flash chromatography on silica gel (PE/EtOAc=2:1) to afford compound A2 (6.00 grams, 75%) as a white solid.

Preparation of Compound A3

The solution of compound A2 (6.00 grams, 12.4 mmol) in $Et_2O$/HCl (30 ml, 2.5 M) was stirred for 2 hours at room temperature under $N_2$ atmosphere. The reaction mixture was concentrated, then added $NaHCO_3$ (sat.) to make PH to 7 then extracted with DCM (80 ml) and washed with brine (80 ml). The organic phase was dried over $Na_2SO_4$ and concentrated in vacuo to give compound A3 (4.50 grams, 96%) as a white solid.

$^1$HNMR (400 MHz, DMSO-$d_6$): δ=1.50 (s, 6H), 2.86-2.91 (m, 1H), 3.35-3.40 (m, 1H), 3.67-3.71 (m, 1H), 5.21 (s, 2H), 7.56 (d, J=1.6 Hz, 1H), 7.12-7.25 (m, 2H), 7.33-7.41 (m, 5H), 7.66 (d, J=12 Hz, 1H), 7.81 (s, 1H), 8.39 (br, 1H).

Preparation of Compound A4

To a stirred solution of compound A3 (731 mg, 1.73 mmol) in THF (20 ml) was added $Ac_2O$ (4.0 ml). After stirring for 2 hours at room temperature under $N_2$ atmosphere, the reaction mixture was concentrated in vacuo. To this residue, DCM (30 ml) was added and washed with saturated $NaHCO_3$ (30 ml×2) and brine (30 ml). The organic phase was dried over $Na_2SO_4$ and concentrated in vacuo to give compound A4 (780 mg, 96%) as a white solid.

$^1$HNMR (400 MHz, DMSO-$d_6$): δ=1.39 (s, 6H), 1.94 (s, 3H), 3.05-3.11 (m, 1H), 3.27-3.32 (m, 1H), 4.73-4.76 (m, 1H), 5.09-5.18 (m, 2H), 6.32 (s, 1H), 6.40 (d, J=7.6 Hz, 1H), 7.02 (d, J=2.0 Hz, 1H), 7.13-7.24 (m, 2H), 7.32-7.40 (m, 6H), 7.65 (d, J=8.0 Hz, 1H), 8.24 (s, 1H).

Preparation of Compound A

To a stirred solution of compound A4 (780 mg, 1.85 mmol) in THF (10 ml) was added 10% Pd/C (330 mg) and stirred for 2 hours under $H_2$ (1 atm) at room temperature. The reaction mixture was filtered, the filtrate was concentrate to give Compound A (321 mg, 52%) as white solid.

$^1$HNMR (400 MHz, DMSO-$d_6$): δ=1.21 (s, 3H), 1.26 (s, 3H), 1.71 (s, 3H), 2.83-2.89 (m, 1H), 3.04-3.09 (m, 1H), 4.54-4.60 (m, 1H), 6.96-7.08 (m, 2H), 7.13 (d, J=13.2 Hz, 1H), 7.32 (d, J=8.0 Hz, 1H), 7.62 (d, J=7.6 Hz, 1H), 8.00 (d, J=8.4 Hz, 1H), 8.17 (d, J=10.0 Hz, 1H), 10.80 (s, 1H), 12.22 (s, 1H).

LC-MS (mobile phase: from 90% water and 10% $CH_3CN$ to 5% water and 95% $CH_3CN$ in 6 minutes, finally under these conditions for 0.5 minutes): purity is 97.9%, Retention time=2.336 minutes.

MS: Calcd.: 331.1; Found: 330.0 (M−H)$^−$.

Preparation of Compound C

FIG. 3

The synthesis of Compound C is depicted in Scheme 2 below.

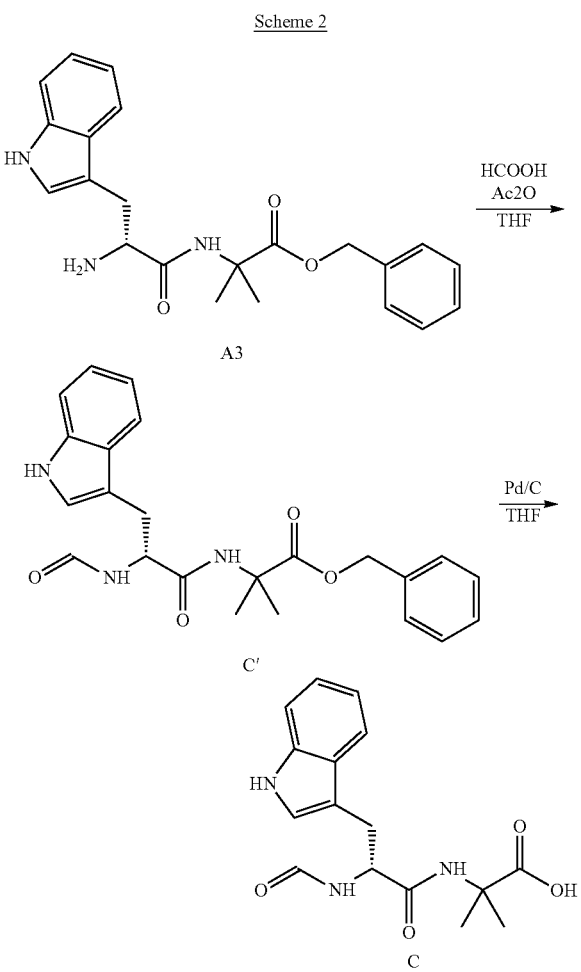

Scheme 2

Preparation of Compound C'

A mixture of HCOOH (1.5 ml, 30.4 mmol) and $Ac_2O$ (2.2 ml, 24.0 mmol) was stirred for 2 hours at 60° C., and then cooled to room temperature. To this reaction mixture was added a solution of compound A3 (2.88 grams, 7.60 mmol, described hereinabove) in THF (20 ml). The mixture was stirred for 2 hours at room temperature under N$_2$ atmosphere, concentrated in vacuo, and the residue was diluted with DCM (100 ml), then washed with saturated NaHCO$_3$ (100 ml×2) and brine (100 ml), and dried over Na$_2$SO$_4$. The organic phase was concentrated in vacuum to give compound C' (780 mg, 96%) as white solid.

$^1$HNMR (400 MHz, DMSO-d$_6$): δ=1.39 (s, 6H), 3.05-3.11 (m, 1H), 3.32-3.37 (m, 1H), 4.78-4.80 (m, 1H), 5.10-5.19 (m, 2H), 6.09 (s, 1H), 6.40 (d, J=7.2 Hz, 1H), 7.04 (d, J=1.5 Hz, 1H), 7.16-7.27 (m, 3H), 7.34-7.42 (m, 5H), 8.06 (br s, 1H), 8.16 (s, 1H).

Preparation of Compound C

A mixture of compound C' (350 mg, 0.86 mmol) and Pd/C (10%, 250 mg) in THF (10 ml) were stirred for 2 hours under H$_2$ (1 atm) at room temperature under N$_2$ atmosphere. The reaction mixture was filtered, the filtrate was concentrated in vacuo to give compound C (200 mg, 73%) as a white solid.

$^1$HNMR (400 MHz, DMSO-d$_6$): δ=1.35 (s, 3H), 1.1.38 (s, 3H), 2.86-2.92 (m, 1H), 3.07-3.12 (m, 1H), 4.64-4.70 (m, 1H), 6.96-7.08 (m, 2H), 7.14 (s, 1H), 7.32 (d, J=8.0 Hz, 1H), 7.62 (d, J=8.0 Hz, 1H), 7.92 (m, 1H), 8.22 (d, J=8.4 Hz, 1H), 8.29 (s, 1H), 10.83 (s, 1H), 12.26 (s, 1H).

LC-MS (mobile phase: from 95% water and 5% CH$_3$CN to 5% water and 95% CH$_3$CN in 6 minutes, finally under these conditions for 0.5 minutes): purity is 98.6%, Retention time=2.309 minutes.

MS: Calcd.: 317.1; Found: 316.0 (M–H)$^-$.

Preparation of Compound B

FIG. 3

The synthesis of Compound B is depicted in Scheme 3 below.

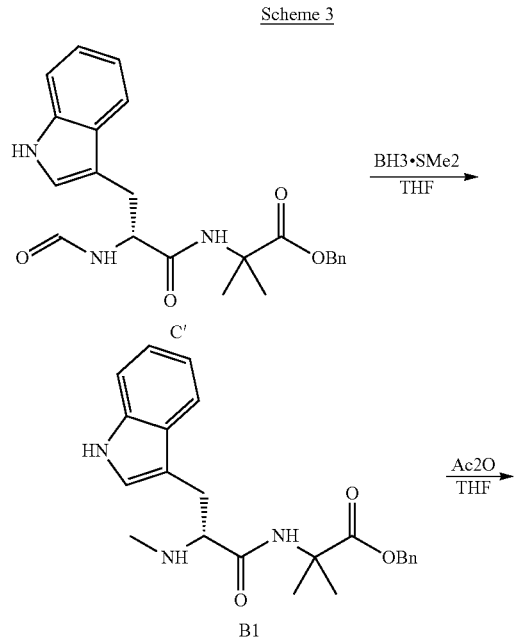

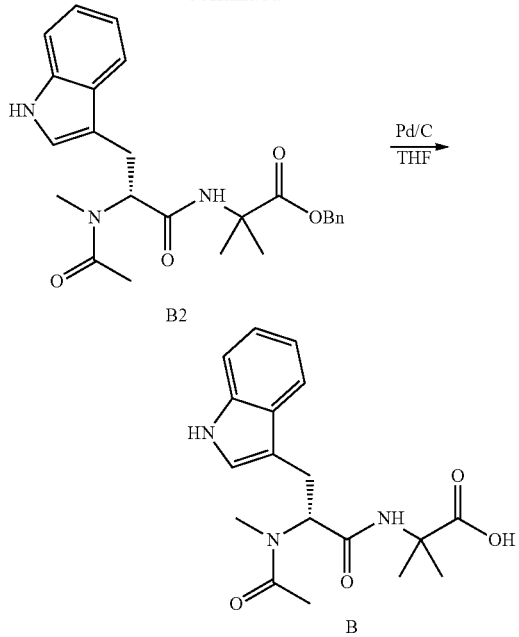

Preparation of Compound B1

To a stirred solution of compound C' (780 mg, 1.85 mmol, described hereinabove) in anhydrous THF (20 ml) was added BH$_3$·SMe$_2$ (1.6 ml, 16 mmol, 10 M in THF) at 0° C. After stirring for 3 hours at room temperature under N$_2$ atmosphere, the reaction mixture was quenched with HCl (con.) at 0° C., then added NaHCO$_3$ (sat.) to make PH to 8 and extracted with EtOAc (40 ml×2). The combined organic phase was washed with brine (40 ml), dried over Na$_2$SO$_4$ and purified by flash chromatography on silica gel (EtOAc) to give compound B1 (400 mg, 17%) as a white solid.

Preparation of Compound B2

To a stirred solution of compound B1 (400 mg, 1.0 mmol) in THF (20 ml) was added Ac$_2$O (2 ml) at room temperature. After stirring for 2 hours under N$_2$ atmosphere, the reaction mixture was diluted with DCM (30 ml), washed with saturated NaHCO$_3$ (30 ml×2) and brine (30 ml), and the organic phase was dried over Na$_2$SO$_4$, concentrated in vacuo and purified by flash chromatography on silica gel (PE/EtOAc=1:1-1:4) to give compound B2 (300 mg, 68%) as a white solid.

$^1$HNMR (400 MHz, DMSO-d$_6$): δ=1.39 (s, 3H), 1.53 (s, 3H), 1.98 (s, 3H), 2.81 (s, 3H), 3.08-3.14 (m, 1H), 3.31-3.36 (m, 1H), 5.21 (s, 2H), 5.40-5.44 (m, 1H), 6.71 (s, 1H), 6.97 (d, J=2.0 Hz, 1H), 7.12-7.23 (m, 2H), 7.34-7.41 (m, 6H), 7.58-7.64 (m, 1H), 8.1 (s, 1H).

Preparation of Compound B

To a stirred solution of compound B2 (300 mg, 0.690 mmol) in THF (10 ml) was added 10% Pd/C (200 mg), and the mixture was stirred for 2 hours under H$_2$ (1 atm) at room temperature, and then filtered. The filtrate was concentrated in vacuo to give Compound B (200 mg, 84%) as a white solid.

$^1$HNMR (400 MHz, DMSO-d$_6$): δ=1.31-1.39 (m, 6H), 1.65 (s, 1.5H), 1.92 (s, 1.5H), 2.78 (s, 1.5H), 2.91 (s, 1.5H), 2.96-3.06 (m, 1H), 3.17-3.21 (m, 1H), 4.55-4.57 (m, 0.5H), 5.31-5.34 (m, 0.5H), 6.98-7.12 (m, 3H), 7.31-7.36 (m, 1H), 6.61-7.66 (m, 1H), 8.05 (s, 0.5H), 8.33 (s, 0.5H), 10.79 (s, 0.5H), 10.89 (s, 0.5H), 12.24 (s, 1H).

LC-MS (mobile phase: from 95% water and 5% $CH_3CN$ to 5% water and 95% $CH_3CN$ in 6 minutes, finally under these conditions for 0.5 minutes): purity is 97.2%, Retention time=2.415 minutes.

MS: Calcd.: 345.1; Found: 346.1 $(M+H)^+$.

Preparation of Compounds U and T

FIG. 3

The preparation of Compounds U and T is depicted in Scheme 4 below.

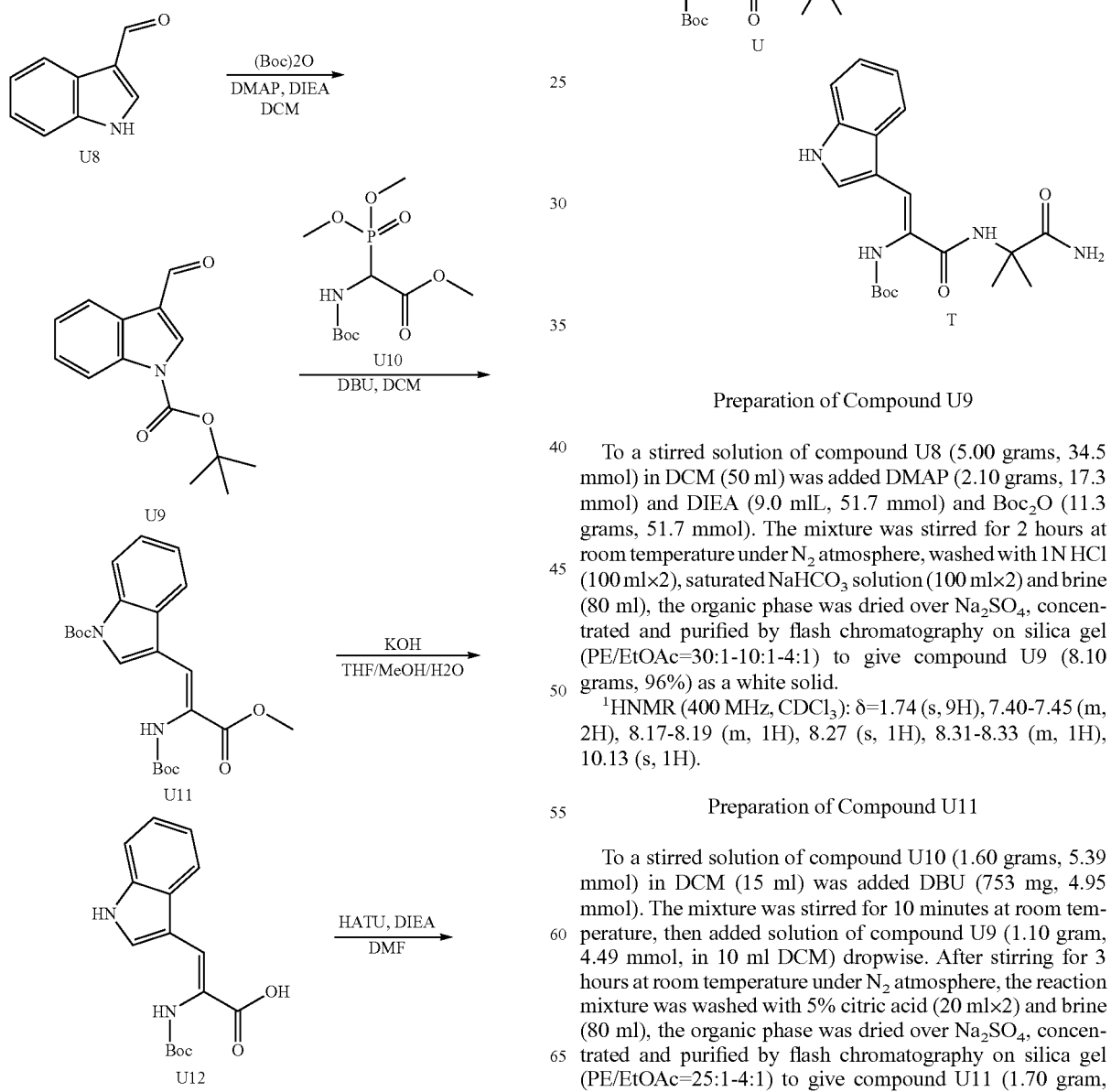

Preparation of Compound U9

To a stirred solution of compound U8 (5.00 grams, 34.5 mmol) in DCM (50 ml) was added DMAP (2.10 grams, 17.3 mmol) and DIEA (9.0 mlL, 51.7 mmol) and $Boc_2O$ (11.3 grams, 51.7 mmol). The mixture was stirred for 2 hours at room temperature under $N_2$ atmosphere, washed with 1N HCl (100 ml×2), saturated $NaHCO_3$ solution (100 ml×2) and brine (80 ml), the organic phase was dried over $Na_2SO_4$, concentrated and purified by flash chromatography on silica gel (PE/EtOAc=30:1-10:1-4:1) to give compound U9 (8.10 grams, 96%) as a white solid.

$^1$HNMR (400 MHz, $CDCl_3$): δ=1.74 (s, 9H), 7.40-7.45 (m, 2H), 8.17-8.19 (m, 1H), 8.27 (s, 1H), 8.31-8.33 (m, 1H), 10.13 (s, 1H).

Preparation of Compound U11

To a stirred solution of compound U10 (1.60 grams, 5.39 mmol) in DCM (15 ml) was added DBU (753 mg, 4.95 mmol). The mixture was stirred for 10 minutes at room temperature, then added solution of compound U9 (1.10 gram, 4.49 mmol, in 10 ml DCM) dropwise. After stirring for 3 hours at room temperature under $N_2$ atmosphere, the reaction mixture was washed with 5% citric acid (20 ml×2) and brine (80 ml), the organic phase was dried over $Na_2SO_4$, concentrated and purified by flash chromatography on silica gel (PE/EtOAc=25:1-4:1) to give compound U11 (1.70 gram, 89%) as a yellow solid.

¹HNMR (400 MHz, CDCl₃): δ=1.48 (s, 9H), 1.71 (s, 9H), 3.90 (s, 3H), 6.24 (br, s, 1H), 7.29-7.40 (m, 2H), 7.62 (s, 1H), 7.74 (d, J=8.0 Hz, 1H), 7.97 (s, 1H), 8.18 (d, J=8.0 Hz, 1H).

Preparation of Compound U12

To a stirred solution of compound U11 (1.70 gram, 4.10 mmol) in THF/MeOH (1:1, 20 ml) was added solution of KOH (1.80 gram, 32.0 mmol, in 10 ml H₂O). After stirring for 2 hours at 60° C. under N₂ atmosphere, HCl (con) was added to the mixture to make PH=3-4 under ice cooled, diluted with H₂O (80 ml), extracted with EtOAc (100 ml×2), the combined organic phase was washed brine (80 ml×2), dried over Na₂SO₄ and concentrated in vacuo to give compound U12 (900 mg, 75%) as a yellow solid.

¹HNMR (400 MHz, DMSO-d₆): δ=1.38 (br, 9H), 7.11-7.21 (m, 2H), 7.42 (d, J=8.0 Hz, 1H), 7.64 (br s, 1H), 7.74 (d, J=8.0 Hz, 1H), 7.81 (s, 1H), 8.27 (br, 1H), 11.71 (br, 1H), 12.24 (br, 1H).

Preparation of Compound U13

To a stirred solution of compound U12 (660 mg, 2.19 mmol) and methyl-2-amino-2-methylpropanoate (HCl) in DMF (20 ml) was added HATU (1.70 gram, 4.40 mmol) and DIEA (1.2 ml, 6.60 mmol) at room temperature, and the mixture was stirred for 16 hours at room temperature under N₂ atmosphere, then poured into ice/water (50 ml), extracted with EtOAc (50 ml×2), and the combined organic phase was washed with 1N HCl (80 ml×2), saturated NaHCO₃ (50 ml×2) and brine (50 ml), dried over Na₂SO₄, the solvent was concentrated in vacuo and the residue was purified by flash chromatography on silica gel (PE/EtOAc=2:1) to give compound U13 (450 mg, 51%) as a yellow solid.

¹HNMR (400 MHz, DMSO-d₆): δ=1.47 (s, 6H), 1.67 (s, 9H), 3.82 (s, 3H), 6.94 (s, 1H), 7.21-7.30 (m, 3H), 7.43-7.45 (m, 1H), 7.61 (s, 1H), 7.76-7.80 (m, 2H), 8.84 (s, 1H).

Preparation of Compound U

To a stirred solution of compound U13 (250 mg, 0.63 mmol) in THF/MeOH (1:1, 20 ml) was added solution of LiOH (120 mg, 2.7 mmol, in 3 ml H₂O), and the reaction mixture was stirred for 2 hours at 60° C. under N₂ atmosphere, then added HCl (concentrated) to make PH to 3 under ice cooled water. The mixture was then diluted with 30 ml H₂O and extracted with EtOAc (50 ml×2), the combined organic phase was washed with brine (50 ml×2), dried over Na₂SO₄ and concentrated in vacuo to give compound U (200 mg, 83%) as a red solid.

¹HNMR (400 MHz, DMSO-d₆): δ=1.40 (s, 6H), 1.48 (s, 9H), 7.11-7.13 (m, 2H), 7.43-7.45 (m, 2H), 7.69-7.75 (m, 4H), 8.6 (s, 1H), 11.64 (s, 1H).
¹³C NMR (100 MHz, MeOH-d₄): δ=13.11, 19.52, 23.48, 23.73, 27.08, 27.29, 56.18, 60.19, 80.29, 109.74, 111.31, 111.43, 117.92, 120.11, 120.23, 122.18, 122.76, 124.54, 126.08, 126.63, 127.48, 135.98, 166.54, 171.66, 176.82.

LCMS (mobile phase: from 95% water and 5% CH₃CN to 5% water and 95% CH₃CN in 6 minutes, finally under these conditions for 0.5 minutes): purity is 97.5%, Retention time=3.415 minutes.
MS: Calcd.: 387.1; Found: 388.1 (M+H)⁺.

Preparation of Compound T

To a stirred solution of compound U (150 mg, 0.39 mmol) and NH₄Cl (70.0 mg, 1.30 mmol) in DMF (10 ml) was added HATU (240 mg, 0.630 mmol) and DIEA (0.5 ml, 2.80 mmol). After stirring for 16 hours at room temperature under N₂ atmosphere, the reaction mixture was poured into ice water (30 ml) and extracted with EtOAc (50 ml×2). The combined organic phase was washed with 1N HCl (50 ml×2), saturated NaHCO₃ (50 ml×2), and brine (50 ml) and dried over Na₂SO₄, concentrated in vacuo and purified by flash chromatography on silica gel (PE/EtOAc=2:1) to give compound T (120 mg, 80%) as a yellow solid.

¹HNMR (400 MHz, DMSO-d₆): δ=1.30-1.51 (m, 15H), 7.10-7.20 (m, 4H), 7.41-7.46 (m, 2H), 7.70-7.73 (m, 2H), 7.87 (s, 1H), 8.55 (s, 1H), 11.60 (s, 1H).
¹³C NMR (100 MHz, MeOH-d₄): δ=24.42, 27.33, 56.69, 80.46, 111.29, 117.97, 120.03, 122.16, 123.41, 126.41, 136.03, 155.51, 166.70.

LCMS (mobile phase: from 95% water and 5% CH₃CN to 5% water and 95% CH₃CN in 6 minutes, finally under these conditions for 0.5 minutes): purity is 97.3%, Retention time=2.782 minutes.
MS Calcd.: 386.2; Found: 387.1 (M+H)⁺.

Preparation of Compounds Q and V

FIG. 3

Compounds U and V were prepared as depicted in Scheme 5 below.

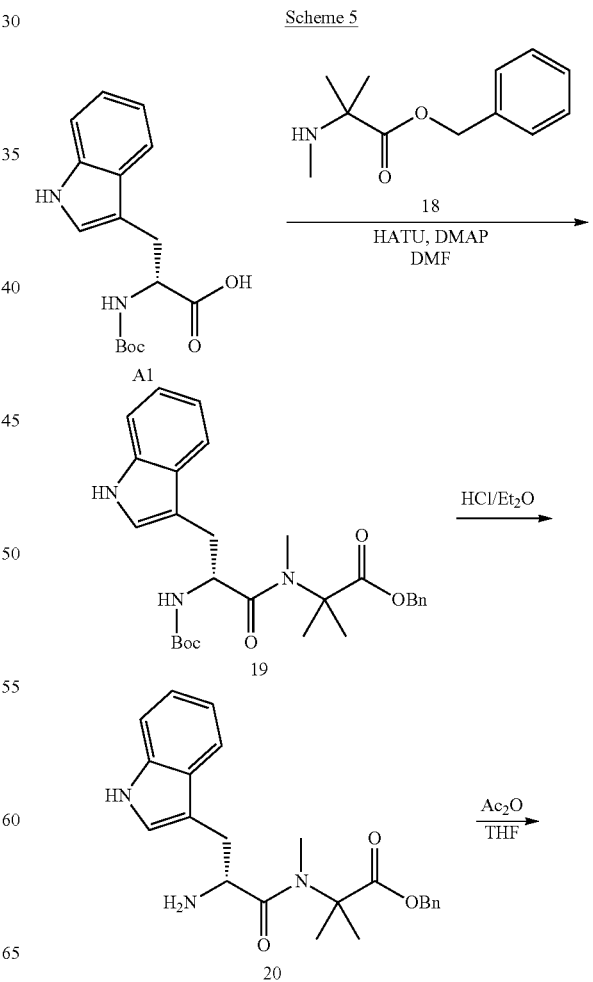

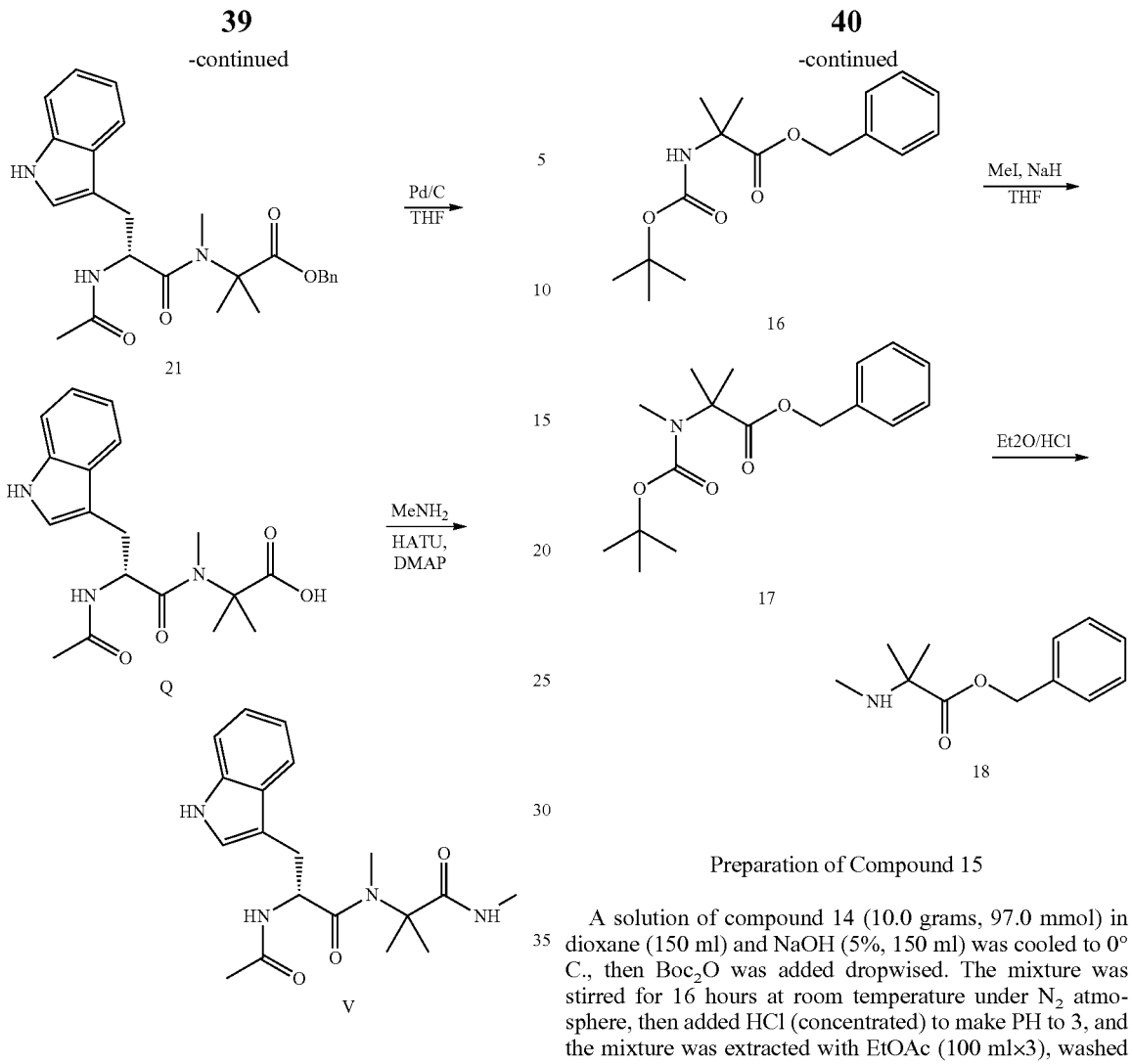

Preparation of Compound 18

Scheme 5

Compound 18 was prepared as depicted in Scheme 6 below.

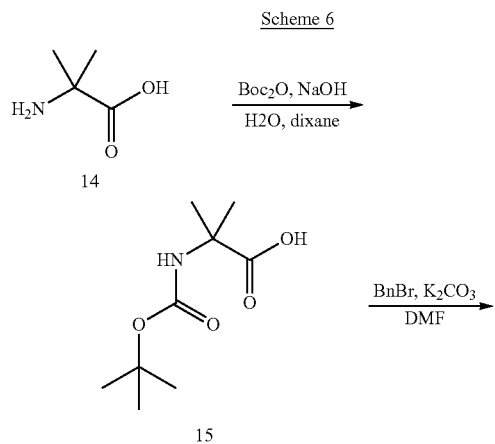

Preparation of Compound 15

A solution of compound 14 (10.0 grams, 97.0 mmol) in dioxane (150 ml) and NaOH (5%, 150 ml) was cooled to 0° C., then Boc$_2$O was added dropwised. The mixture was stirred for 16 hours at room temperature under N$_2$ atmosphere, then added HCl (concentrated) to make PH to 3, and the mixture was extracted with EtOAc (100 ml×3), washed with brine (50 ml), dried over Na$_2$SO$_4$, concentrated in vacuo and purified on silica gel column (PE/EtOAc=5:1) to give the product as white solid (12.1 grams, 61% yield).

Preparation of Compound 16

To a stirred mixture of compound 15 (8.60 grams, 42.3 mmol) and K$_2$CO$_3$ (8.80 grams, 63.5 mmol) in DMF (150 ml) was added BnBr (6.20 ml, 51.0 mmol) dropwise at 0° C. After stirring for 15 hours at room temperature under N$_2$ atmosphere, the reaction mixture was poured into water (200 ml), and extracted with EtOAc (200 ml×3). The combined organic phase was washed with brine (100 ml), dried over Na$_2$SO$_4$ and concentrated in vacuo. To this residue, hexane (50 ml) and the mixture was added and stirred for 30 minutes, filtered to afford compound 16 (8.50 grams, 69%) as a white solid.

$^1$HNMR (400 MHz, CDCl$_3$): δ=1.43 (s, 9H), 1.54 (s, 6H), 5.04 (br, s, 1H), 5.19 (s, 2H), 7.37-7.38 (m, 5H).

Preparation of Compound 17

To a stirred solution of compound 16 (5.00 grams, 17 mmol) in THF (100 ml) was added NaH (5.40 grams, 60%, 136 mmol, washed with hexane) at ice cooled, and the reaction mixture was stirred for 2 hours in ice/water bath, then MeI (4.50 ml, 85.0 mmol) was added dropwise. The mixture was stirred for 15 hours at 30° C. under N$_2$ atmosphere, and was then poured into ice/water (100 ml) slowly and extracted with EtOAc (100 ml×3). The combined organic phase was washed with brine (100 ml×2), dried over $Na_2SO_4$ and concentrated in vacuo to give compound 17 (4.00 grams, 77%) as a yellow oil.

$^1$HNMR (400 MHz, $CDCl_3$): δ=1.45 (s, 9H), 1.47 (s, 6H), 2.93 (s, 3H), 5.16 (s, 2H), 7.33-7.38 (m, 5H).

Preparation of Compound 18

The solution of compound 17 (4.0 grams, 13.0 mmol) in $Et_2O$/HCl (30 ml, 2.5 M) was stirred for 2 hours at room temperature under $N_2$ atmosphere. The solvent was then evaporated and to the residue was added hexane (40 ml) and the mixture was stirred for 30 minutes, and filtered to give HCl salt of compound 18 (2.3 grams, 74%) as a white solid.

$^1$HNMR (400 MHz, $CD_3OD$): δ=1.61 (s, 6H), 2.70 (s, 3H), 5.33 (s, 2H), 7.70-7.50 (m, 5H).

Preparation of Compound 19

To a stirred solution of compound A1 (3.60 grams, 11.8 mmol) and compound 18 (HCl) salt in DMF (100 ml) was added HATU (5.60 grams, 14.8 mmol) and DMAP (3.60 grams, 29.4 mmol) at room temperature, and the mixture was stirred for 16 hours at room temperature under $N_2$ atmosphere, then poured into ice water (100 ml) and extracted with EtOAc (150 ml×2). The combined organic phase was washed with 1N HCl (aq) (100 ml×2), saturated $NaHCO_3$ (100 ml×2) and brine (100 ml), then dried over $Na_2SO_4$, concentrated in vacuo and purified by flash chromatography on silica gel (PE/EtOAc=2:1) to afford compound 19 (2.70 grams, 56%) as a yellow solid.

$^1$HNMR (400 MHz, DMSO-$d_6$): δ=1.32 (d, J=8.8 Hz, 6H), 1.49 (s, 9H), 2.58 (s, 3H), 3.04-3.11 (m, 2H), 4.94-4.99 (m, 1H), 5.10-5.21 (m, 2H), 5.41-5.43 (m, 1H), 6.95 (s, 1H), 7.12-7.21 (m, 2H), 7.29-7.39 (m, 6H), 7.72 (d, J=7.6 Hz, 1H), 8.15 (s, 1H).

Preparation of Compound 20

A solution of compound 19 (500 mg, 1.01 mmol) in $Et_2O$/HCl (2.5 M, 20 ml) was stirred for 2 hours at room temperature under $N_2$ atmosphere, and thereafter the reaction mixture was concentrated in vacuo to give compound 20 (450 mg, crude).

Preparation of Compound 21

A solution of compound 20 (450 mg, crude) and $Ac_2O$ (2.0 ml) and DIEA (1.0 ml) in THF (20 ml) was stirred for 2 hours at room temperature under $N_2$ atmosphere, and thereafter the reaction mixture was concentrated in vacuo and diluted with EtOAc (30 ml), the organic phase was washed with 1 N HCl (aq) (20 ml×2), saturated $NaHCO_3$ (20 ml×2) and brine (20 ml), dried over $Na_2SO_4$, and the solvent was removed in vacuo to afford compound 21 (400 mg, 91%) as a yellow solid.

Preparation of Compound Q

The mixture of compound 21 (500 mg, crude) and 10% Pd/C (250 mg) in THF (20 ml) was stirred for 2 hours at room temperature under $H_2$ (1 atm), then filtered, and the filtrate was concentrated to give Compound Q (250 mg, 88%) as a white solid.

$^1$HNMR (400 MHz, DMSO-$d_6$): δ=1.25-1.31 (s, 6H), 1.79 (s, 3H), 2.83 (s, 3H), 2.85-2.88 (m, 1H), 3.00-3.05 (m, 1H), 4.94-5.00 (m, 1H), 6.98-7.09 (m, 2H), 7.14 (d, J=2.0 Hz, 1H), 7.33 (d, J=8.0 Hz, 1H), 7.58 (d, J=8.0 Hz, 1H), 8.20 (d, J=8.8 Hz, 1H), 10.83 (s, 1H), 11.91 (br s, 1H).

LC-MS (mobile phase: from 95% water and 5% $CH_3CN$ to 40% water and 60% $CH_3CN$ in 6 minutes, finally under these conditions for 0.5 minutes): purity is >95%, Retention time=1.958 minutes.

MS Calcd.: 345.2; Found: 346.1 $(M+H)^+$.

Preparation of Compound V

To a stirred solution of Compound V (230 mg, 0.67 mmol) and $MeNH_2$·HCl (222 mg, 3.33 mmol) in DMF (20 ml) was added HOBT (135 mg, 1 mmol) and DIEA (0.8 ml, 4.70 mmol), then added EDCI (192 mg, 1.00 mmol) at room temperature, and the reaction mixture was stirred for 16 hours at room temperature under $N_2$ atmosphere, concentrated in vacuo and purified by Prep-HPLC to give Compound V (30 mg, 17%) as a white solid.

$^1$HNMR (400 MHz, $CDCl_3$): δ=1.35 (d, J=5.2 Hz, 6H), 1.99 (s, 3H), 2.65 (d, J=4.8 Hz, 3H), 2.74 (s, 3H), 3.21-3.24 (m, 2H), 5.16-5.18 (m, 1H), 5.61 (br s, 1H), 6.48 (br s, 1H), 7.16-7.29 (m, 3H), 7.40 (d, J=7.6 Hz, 1H), 7.70 (d, J=7.6 Hz, 1H), 8.20 (s, 1H).

LC-MS [mobile phase: from 90% water (0.02% $NH_4Ac$) and 10% $CH_3CN$ to 5% water (0.02% $NH_4Ac$) and 95% $CH_3CN$ in 6 minutes, finally under these conditions for 0.5 minutes]: purity is >95%, Retention time=2.090 minutes.

MS Calcd.: 327.2; Found: 328.1 $(M^++H)$.

Preparation of Compound R

FIG. 3

Compound R was prepared as depicted in Scheme 7 below.

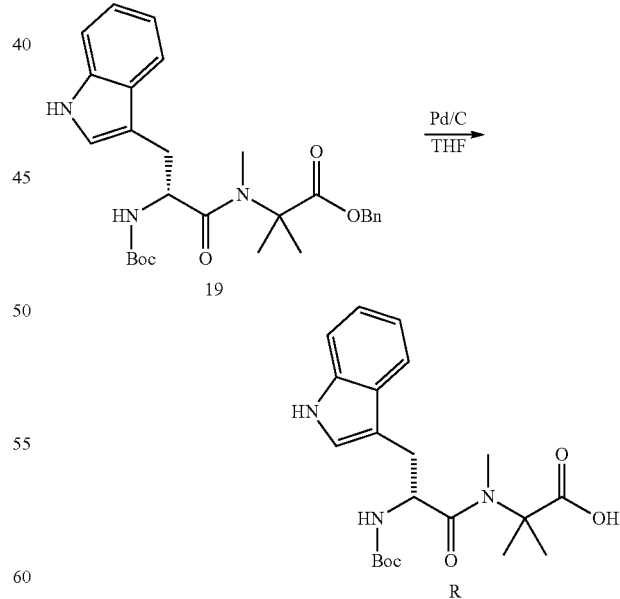

The mixture of compound 19 (1.50 gram, 3.8 mmol) and Pd/C (10%, 400 mg) in THF (40 ml) was stirred for 15 hours at room temperature under $H_2$ (1 atm), then filtered, and the filtrate was concentrated to give compound R (1.20 gram, 80%) as a red solid.

$^1$HNMR (400 MHz, DMSO-d$_6$): δ=1.20-1.32 (m, 15H), 2.87-2.30 (m, 5H), 4.60-4.65 (m, 1H), 6.83-7.16 (m, 4H), 7.33-7.57 (m, 2H), 10.84 (s, 1H), 11.88 (s, 1H).

LC-MS (mobile phase: from 95% water and 5% CH$_3$CN to 5% water and 95% CH$_3$CN in 6 minutes, finally under these conditions for 0.5 minutes): purity is 98.6%, Retention time=3.685 minutes.

MS Calcd.: 403.2; Found: 404.1 (M$^+$+H).

Preparation of Compounds D, E and F

FIG. 3

Compounds D, E and F were prepared as depicted in Scheme 8 below.

Scheme 8

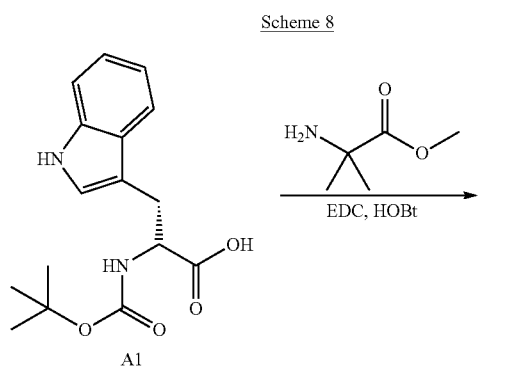

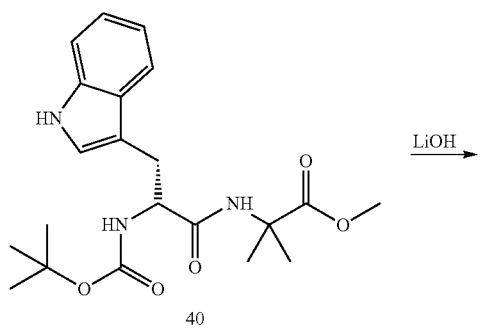

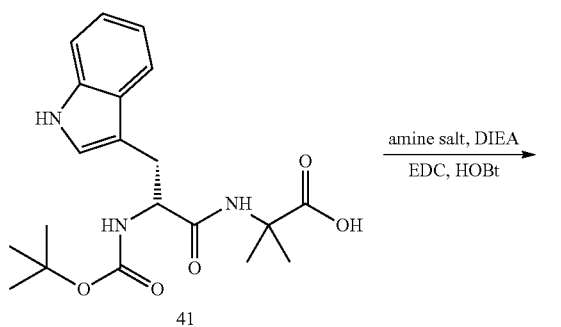

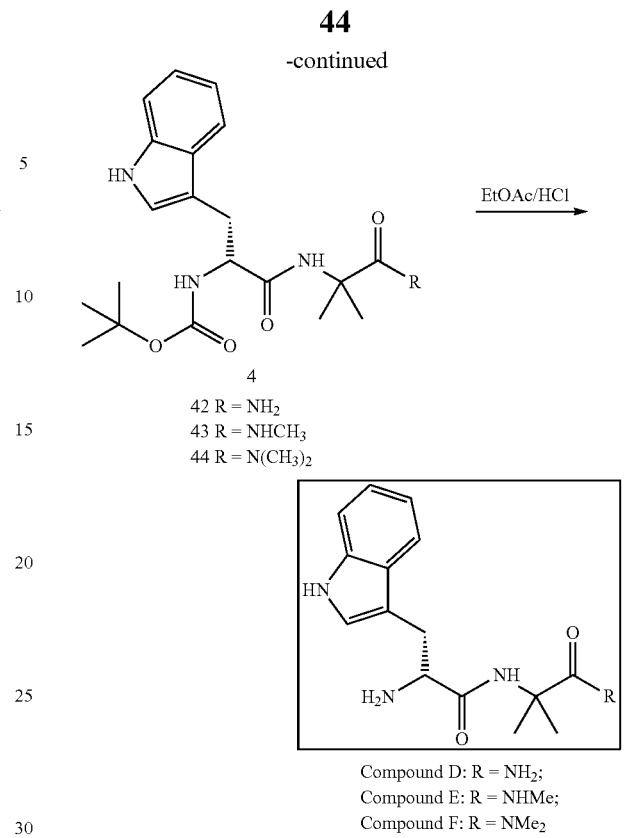

42 R = NH$_2$
43 R = NHCH$_3$
44 R = N(CH$_3$)$_2$

Compound D: R = NH$_2$;
Compound E: R = NHMe;
Compound F: R = NMe$_2$

Preparation of Compound 40

To a stirred solution of compound A1 (2.0 grams, 6.6 mmol) in DMF (10 ml) was added amine (1.1 gram, 7.0 mmol), HOBt (945 mg, 7 mmol), EDC (1.9 gram, 10 mmol) and DIEA (2.6 grams, 20 mmol). After stirring for 16 hours at room temperature under N$_2$ atmosphere, the reaction mixture was poured into ice/water (20 ml) and extracted with EtOAc (20 ml×3), and the combined organic phase was washed with brine (50 ml), dried over Na$_2$SO$_4$ and concentrated in vacuo. The residue was purified on silica gel column (PE:EtOAc=8: 1) to give compound 40 (3.2 grams, 81% yield).

Preparation of Compound 41

To a solution of compound 40 (4.8 grams, 12 mmol) in MeOH (50 ml) and H$_2$O (10 ml) was added LiOH H$_2$O (608 mg, 15 mmol). After stirring for 4 hours at room temperature, HCl (concentrated) was added to the reaction mixture to make PH to 5, water (40 ml) was added and the mixture was extracted with EtOAc (40 ml×3). The combined organic phase was washed with brine (50 ml), dried over Na$_2$SO$_4$ and concentrated in vacuo to give compound 41 as white solid (4.2 grams, 90% yield).

Preparation of Compounds 42, 43 and 44

To a solution of compound 41 (300 mg, 0.77 mmol) in DMF (10 ml) was added amine salt (2.3 mmol, selected according to the desired product), HOBt (157 mg, 1.2 mmol), EDC (2.23 grams, 1.2 mmol) and DIEA (298 mg, 2.3 mmol). After stirring for 16 hours at room temperature under N$_2$ atmosphere, the mixture was poured into H$_2$O (50 ml) and extracted with EtOAc (50 ml×3). The combined organic phase was washed with brine (50 ml), dried over Na$_2$SO$_4$ and concentrated in vacuo. The residue was purified on silica gel column (PE: EtOAc=8:1) to give the product (42, 43 or 44).

Preparation of Compounds D, E and F

A solution of compound 42 (or 43 or 44) in EtOAc/HCl (4N, 10 ml) was stirred for 2 hours at room temperature, then concentrated in vacuo and purified by Prep-HPLC to give the corresponding product as white solid.

Compound D:

90 mg, 51% yield;

$^1$H NMR (400 MHz, DMSO-d$_6$): δ=1.28 (s, 6H), 3.30-3.03 (m, 2H), 4.03 (t, J=7.0 Hz, 1H), 7.20-6.90 (m, 5H), 7.37 (d, J=7.6 Hz, 1H), 7.71 (d, J=7.6 Hz, 1H), 8.25-8.00 (br s, 3H), 8.54 (s, 1H), 11.04 (s, 1H).

LC-MS [mobile phase: from 95% water (0.05% TFA) and 5% CH$_3$CN to 5% water (0.05% TFA) and 95% CH$_3$CN in 6 minutes, finally under these conditions for 0.5 minutes]: purity is >95%, Retention time=2.308 minutes.

MS: Calcd.: 288.1; Found: 289.1 (M$^+$+H).

Compound E:

75 mg, 57% yield;

$^1$H NMR (400 MHz, DMSO-d$_6$): δ=1.27 (s, 6H), 2.52 (s, 3H), 3.30-3.02 (m, 2H), 4.02 (t, J=7.2 Hz, 1H), 7.20-7.00 (m, 3H), 7.38 (d, J=7.6 Hz, 1H), 7.53 (d, J=7.6 Hz, 1H), 7.70 (d, J=8.0 Hz, 1H), 8.35-7.90 (br s, 3H), 8.59 (s, 1H), 11.03 (s, 1H).

LC-MS [mobile phase: from 95% water (0.05% TFA) and 5% CH$_3$CN to 5% water (0.05% TFA) and 95% CH$_3$CN in 6 minutes, finally under these conditions for 0.5 minutes]: purity is >95%, Retention time=2.391 minutes.

MS: Calcd.: 302.1; Found: 303.1 (M$^+$+H).

Compound F:

50 mg, 47% yield;

$^1$H NMR (400 MHz, DMSO-d$_6$): δ=1.32 (s, 3H), 1.34 (s, 3H), 3.10-2.65 (m, 8H), 3.47 (dd, J=7.6, 5.4 Hz, 1H), 7.15-7.00 (m, 3H), 7.34 (d, J=8.0 Hz, 1H), 7.59 (d, J=8.4 Hz, 1H), 8.13 (s, 1H), 10.90 (s, 1H).

LC-MS [mobile phase: from 95% water and 5% CH$_3$CN to 5% water and 95% CH$_3$CN in 6 minutes, finally under these conditions for 0.5 minutes]L purity is 98.3%, Retention time=2.568 minutes.

MS: Calcd.: 316.1; Found: 317.2 (M$^+$+H).

Preparation of Compound W

FIG. 3

Compound W was prepared as depicted in Scheme 9 below, while utilizing benzyloxycarbonyl (Z) as a protecting group of the N-terminus of the dipeptide analog and phenacyl ester (2-phenyl-2-oxoethyl ester, Pac) as a protecting group of the C-terminus of the dipeptide analog, to thereby generate Z-D-Trp-Aib-OPac. Both Z and Pac protecting groups are removed by catalytic hydrogenation.

Scheme 9

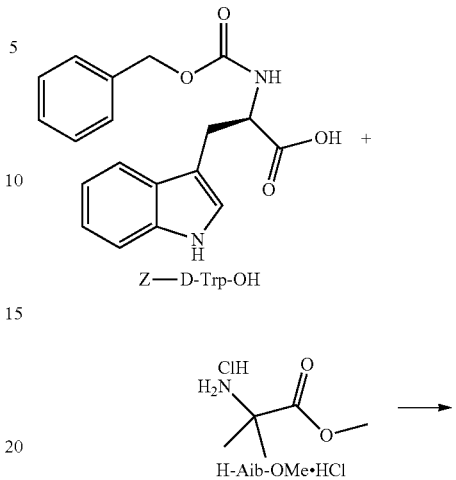

Z—D-Trp-OH

H-Aib-OMe·HCl

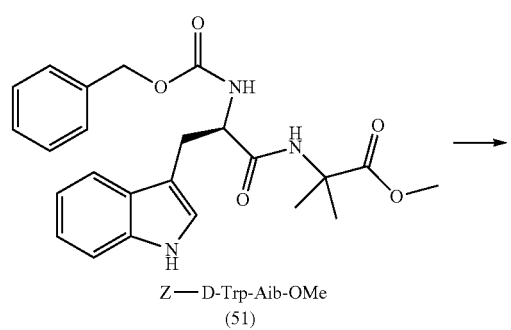

Z—D-Trp-Aib-OMe
(51)

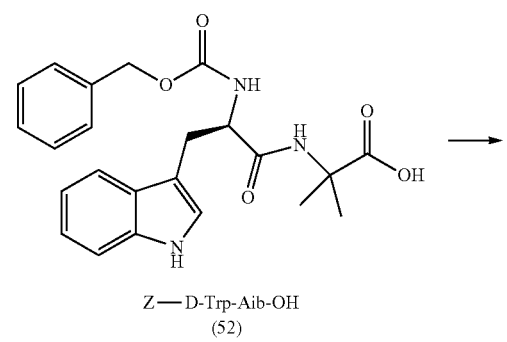

Z—D-Trp-Aib-OH
(52)

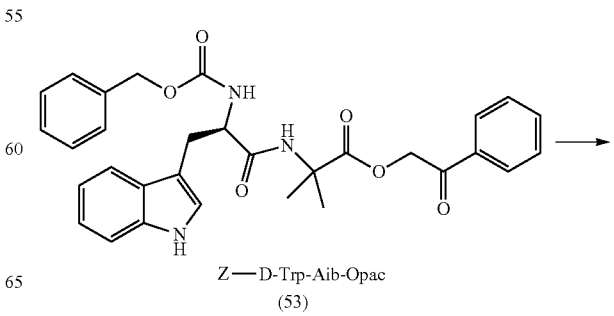

Z—D-Trp-Aib-Opac
(53)

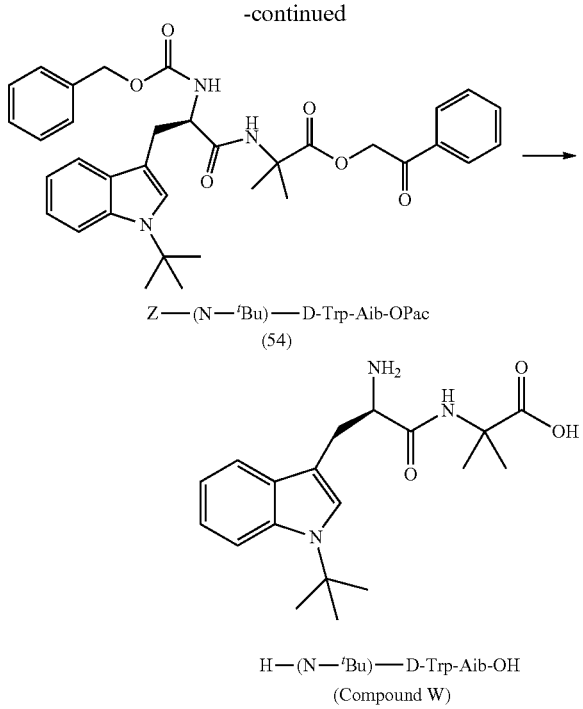

Z—(N—$^t$Bu)—D-Trp-Aib-OPac
(54)

H—(N—$^t$Bu)—D-Trp-Aib-OH
(Compound W)

Preparation of Z-D-Trp-Aib-OMe

Compound 51

33.84 grams (100 mmol) Z-D-Trp-OH was dissolved in 150 ml EtOAc. 30.44 grams (110 mmol) N-(4,6-Dimethoxy-1,3,5-triazin-2-yl)-N-methylmorfolinium chloride was added at 0-5° C. H-Aib-OMe was deliberated from 28.56 grams (186 mmol) hydrochloride salt and was added to the reaction mixture. 20 ml (150 mmol, 1.5 equivalent) triethylamine was also added, and the reaction mixture was stirred at room temperature for a day. The reaction mixture was thereafter worked up by adding 150 ml water, separating phases, washing the organic phase with 150 ml saturated NaHCO$_3$ and 150 ml saturated NaCl, drying on Na$_2$SO$_4$ and evaporating the solvent. Crude Compound 51 was obtained as orange oil (45.0 grams, 103 mmol, 103%), and was purified by column chromatography on silica (using toluene:MeOH 9:1 as eluent), so as to produce Compound 51 as an orange oil (40.0 grams, 91.4 mmol, 91.4% yield).

Preparation of Z-D-Trp-Aib-OH

Compound 52

A solution of 20.0 grams (46 mmol) Z-D-Trp-Aib-OMe in a mixture of 100 ml methanol, 10 ml water and 2.2 grams (55 mmol) NaOH was stirred at room temperature for a day. The reaction mixture was thereafter worked-up by evaporating the solvent, adding 200 ml water to the obtained residue, extracting with 3×50 ml cyclohexane, setting pH of aqueous phase to 3 with 10 ml 85% H$_3$PO$_4$, filtering the formed precipitate while washing precipitate with 400 ml water, and drying in vacuum at 40° C. Compound 52 was obtained as a white solid product (17.0 grams, 40 mmol, 87% yield).

Preparation of Z-D-Trp-Aib-OPac Compound 53

To a solution of 4.23 grams (10 mmol) of Z-D-Trp-Aib-OH (Compound 52) and 1.99 grams (10 mmol) 2'-bromoacetophenone in 20 ml EtOAc, 1.4 ml (10 mmol) triethylamine was added and the reaction mixture was stirred at room temperature overnight. The reaction mixture was thereafter worked-up by adding 50 ml EtOAc, washing the organic phase with 20 ml 1 M KHSO$_4$, 20 ml water, 20 ml 1 M NaHCO$_3$ and 20 ml water, and evaporating the solvent. The obtained crude product was purified by column chromatography on silica (using hexane:EtOAc 1:1 as eluent), to yield Compound 53 as a transparent oil (4.3 grams, 7.9 mmol, 79% yield).

Preparation of Z—(N-$^t$Bu)-D-Trp-Aib-OPac

Compound 54

4.3 grams (7.9 mmol) Z-D-Trp-Aib-OPac (Compound 53) was placed in a metal reactor along with 40 ml dichloromethane and 0.24 ml concentrated H$_2$SO$_4$ as catalyst. Isobutylene was condensed into the reactor at −5° C. (cooled in a salt-ice bath). The reaction mixture was stirred for a day at room temperature and 2.5 bar pressure, and was thereafter worked-up by evaporating the isobutylene, washing the residual organic phase with 50 ml 10% NaOH and evaporating the organic phase. The thus obtained crude product was purified by column chromatography on silica (using CHCl$_3$: MeOH 98:2 as eluent), to afford Compound 54 as a light yellow solid product (2.85 grams, 4.8 mmol, 60% yield).

Preparation of H—(N-$^t$Bu)-D-Trp-Aib-OH

Compound W 1.2 gram (2 mmol) of Z—(N-$^t$Bu)-D-Trp-Aib-OPac (Compound 54) was dissolved in 100 ml MeOH, the solution was placed in a reactor and 0.12 gram SelCat Q6 catalyst (Pd/C-type) was added thereto. The reaction mixture was stirred for a day at room temperature and 1.5 bar H$_2$ pressure and was thereafter worked-up by filtration, washing the catalyst with 2×50 ml hot methanol, combining the organic phases and evaporating the solvent. The solid residue was purified by column chromatography on silica (using toluene:methanol 1:1 as eluent) to afford Compound W as a light yellow solid (126 mg, 0.36 mmol, 18% yield).

$^1$H-NMR (recorded at 11.7 Tesla on a Bruker AVANCE-500 MHz (two-channel) spectrometer at 300K in DMSO): δ=1.35 (s), 1.64 (s), 2.80, 3.07, 3.45 (t), 6.98 (t), 7.07 (t), 7.58 (d), 7.63 (d), 8.37, 8.52.

Example 2

Activity Assays

Peptide Solutions:

D-Trp-Aib analogs as described herein, as well as other peptides tested for comparison, were dissolved in DMSO to a concentration of 50 mM and 100 mM, sonicated for 20 seconds in ice and then diluted with DMSO to their final concentrations.

Oligomer Formation (Hillen Protocol):

Aβ$_{1-42}$ intermediates and globulomers were produced according to Barghorn et al. [J. Neurochem. 2005 November; 95(3):834-47]. Synthetic lyophilized β-amyloid polypeptides (Aβ 1-42, >98% pure) were purchased from Bachem (Bubendorf, Switzerland). To avoid pre-aggregation, synthetic lyophilized Aβ$_{1-42}$ was pretreated with HFIP. Aβ$_{1-42}$ was dissolved in 100% HFIP, sonicated for 20 seconds and incubated for 2 hours at 37° C. under shaking at 100 RPM. After evaporation in a speedVac, Aβ$_{1-42}$ was re-suspended in DMSO, with or without the tested peptide, to 5 mM and diluted with 20 mM NaH$_2$PO$_4$, 140 mM NaCl, pH 7.4, to a final concentration of 400 µM, and 1/10 volume 2% SDS (final concentration of 0.2%). The Aβ globulomers were generated by further dilution with two volumes of H$_2$O and incubation for 18 hours or more. Aβ aggregation products were then separated using a 15% tris-tricine gel and stained using Imperial protein stain.

Western Blot Analysis:

To evaluate the effect of D-Trp-Aib analogs on the transformation of the Aβ$_{1-42}$ into the toxic assemblies, the tested peptides were incubated with Aβ$_{1-42}$ at increasing molar ratios, and the reaction mixtures were resolved on SDS-PAGE followed by western blot analysis by a specific anti Aβ antibody (6E10) (SIGNET).

Thioflavin T Fluorescence Assay:

Fibrillization of Aβ 1-42 polypeptide was monitored using a Thioflavin T (ThT) dye binding assay. A 10 µM Aβ 1-42 solution was prepared as described above and was immediately mixed with the tested analog stock solutions (100 µM), so as to achieve a final concentration of 5 µM for Aβ and various concentrations of the tested analog. For each measurement, ThT was added to a 0.1 ml sample, to give a final concentration of 0.3 µM ThT and 0.4 µM Aβ. The samples were incubated at 37° C. Fluorescence measurements, made after addition of the ThT solution to each sample at 37° C., were carried out using a Jobin Yvon FluoroMax-3 spectrometer (excitation 450 nm, 2.5 nm slit; emission 480 nm, 5 nm slit, integration time of 1 second). Background was subtracted from each sample. Each experiment was repeated in quadruplicate.

Results:

All of the dipeptide analogs as described herein tested using Hillen protocol for Aβ$_{1-42}$ globulomer generation, were found to exhibit inhibition of Aβ$_{1-42}$ globulomer generation to a greater extent as measured for D-Trp-Aib (MRZ99030) at 1:1 (inhibitor:Aβ peptide) molar ratio and even at lower concentrations. All of the tested analogs showed complete inhibition at 20:1 (inhibitor:Aβ peptide) molar ratio.

Figures 5A, 5B:
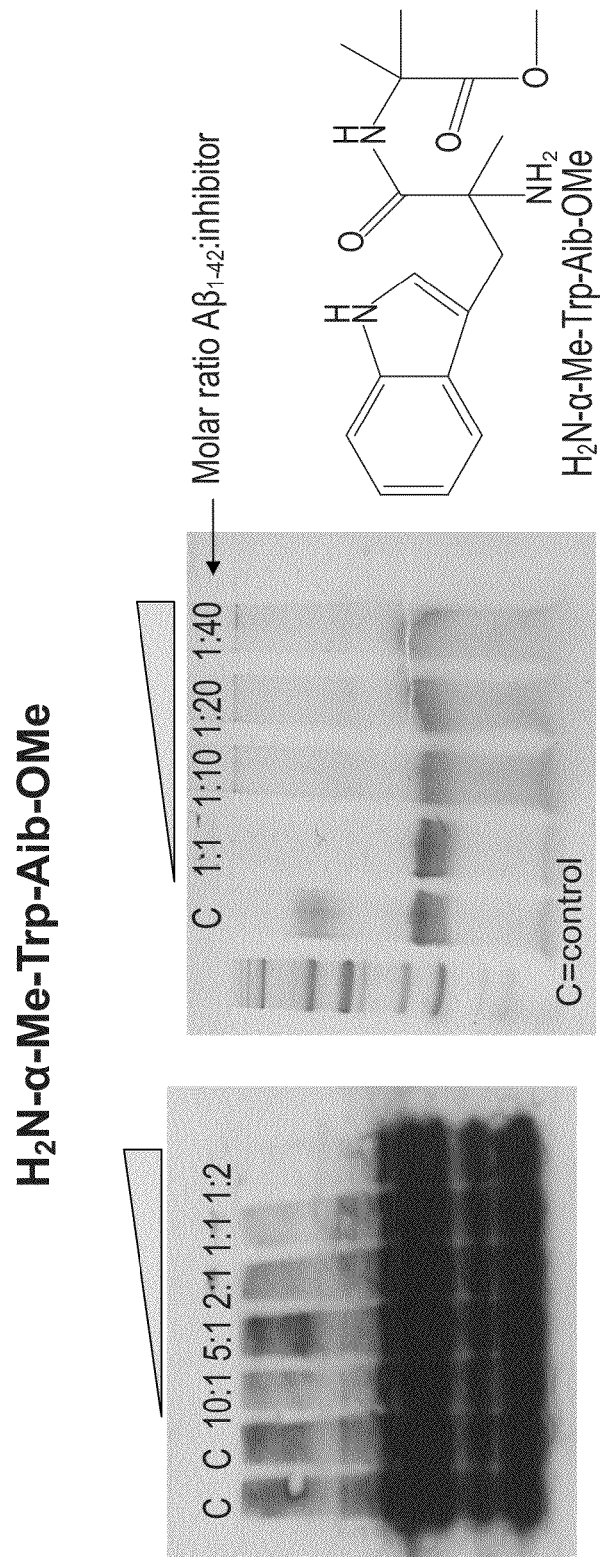
FIGS. 5A-B present Western Blot Analyses (FIG. 5A) and data obtained using a 15% tris-tricine gel and Imperial protein staining (FIG. 5B), demonstrating the effect of Compound 2, $H_2N$-α-Me-Trp-Aib-OMe on globulomer inhibition at various inhibitor:Aβ peptide molar ratio, obtained using the Hillen protocol.

Compound 2, H$_2$N-α-Me-Trp-Aib-OMe (see, Table 1 above), showed complete globulomer inhibition at 1:1 (inhibitor:Aβ peptide) molar ratio, using the Hillen protocol (see, FIG. 5A for data obtained using Western Blot Analyses and FIG. 5B for data obtained using a 15% tris-tricine gel and Imperial protein staining).

Figure 6:
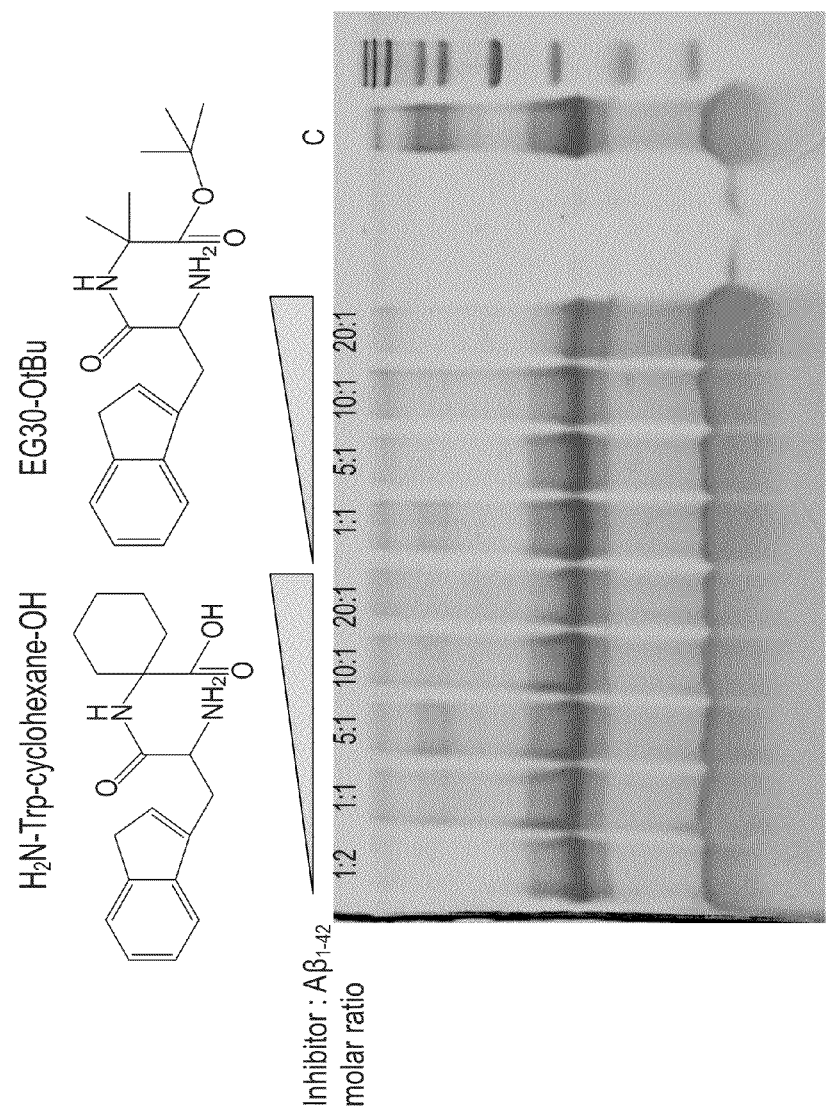
FIG. 6 presents data demonstrating the effect of Compounds 1 and 7 in inhibiting $Aβ_{1-42}$ fibril formation at various inhibitor:Aβ peptide molar ratio, using the Hillen protocol.

Compounds 1 and 7 (see, Table 1 hereinabove) were shown, using the Hillen protocol, to inhibit Aβ$_{1-42}$ fibril formation at a 10:1 and 20:1 (inhibitor:Aβ peptide) molar ratio (see, FIG. 6).

Figure 7:
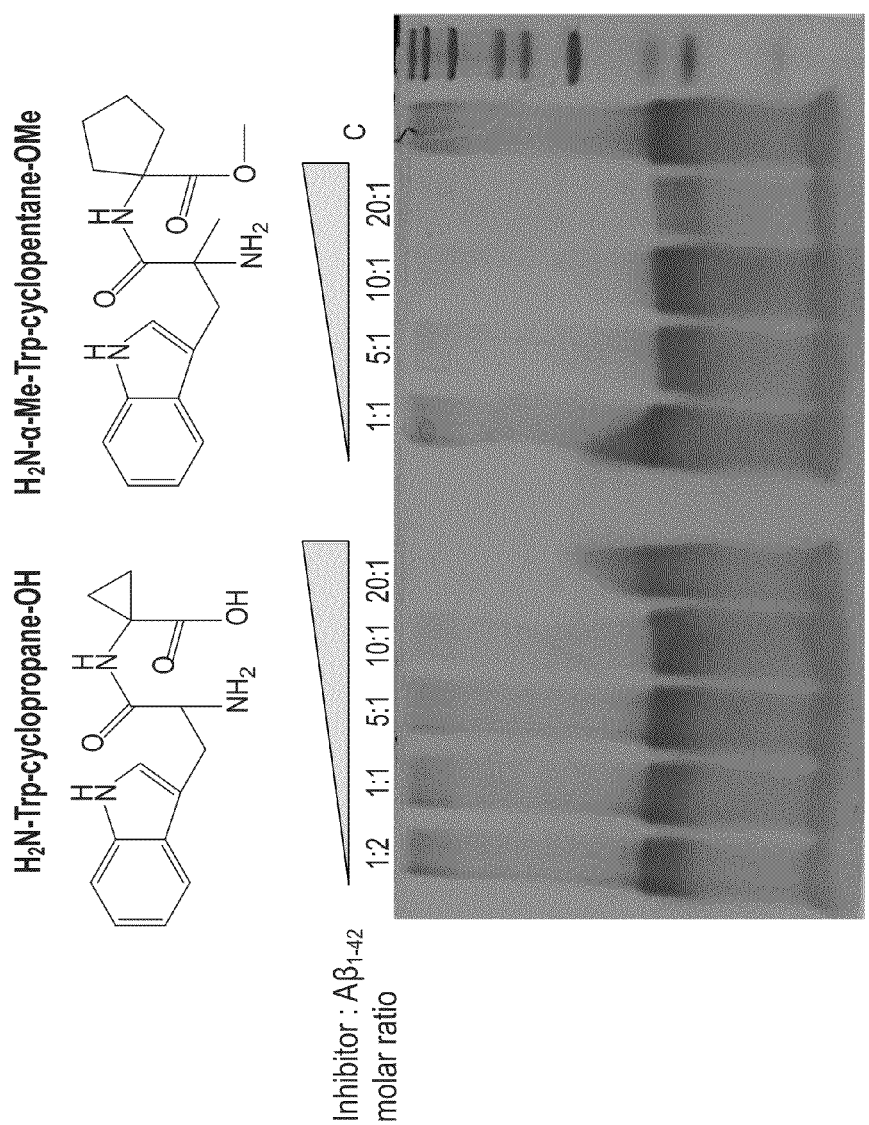
FIG. 7 presents data demonstrating the effect of Compounds 3 and 5 in inhibiting $Aβ_{1-42}$ fibril formation at various inhibitor:Aβ peptide molar ratio, using the Hillen protocol.

Compounds 3 and 5 (see, Table 1 hereinabove) were shown, using the Hillen protocol, to inhibit Aβ$_{1-42}$ fibril formation at a 10:1 (inhibitor:Aβ peptide) molar ratio (see, FIG. 7).

Figure 8:
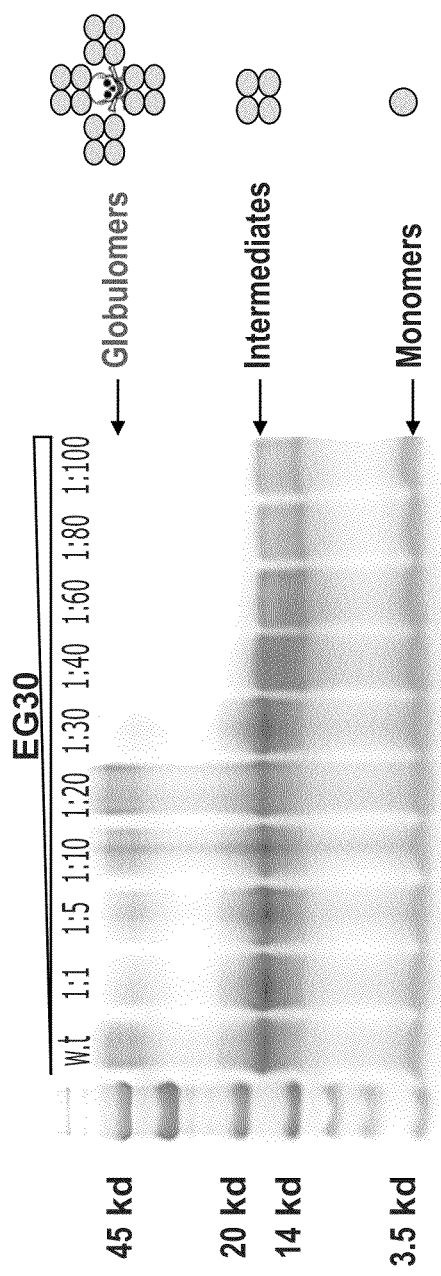
FIG. 8 presents comparative data demonstrating the effect of D-Trp-Aib (EG30) in inhibiting $Aβ_{1-42}$ fibril formation at various inhibitor:Aβ peptide molar ratio, using the Hillen protocol.

For comparison, data obtained for the inhibition of Aβ$_{1-42}$ globulomer generation as measured for D-Trp-Aib (EG30), using the Hillen protocol, showed complete inhibition only at 40:1 (inhibitor:Aβ peptide) molar ratio (see, FIG. 8).

For further comparison, it is noted that the following tested peptides did not show any activity in inhibiting Aβ$_{1-42}$ globulomer generation: dF-dF-Aib; Y-Aib-Aib; Aib-Y-Y; dY-Aib; and N-Y-Y-P.

Example 3

Activity Assays

SPR Binding Assay

Surface Plasmon Resonance (SPR) studies were performed using a BIACORE X100 biosensor instrument (GE Lifesciences, Uppsala, Sweden), equipped with two flow cells on a sensor chip. Aβ monomers were covalently coupled to one flow cell of CM7 sensor chips (GE Lifesciences, Uppsala, Sweden) via primary amines using the Amine Coupling Kit (GE Lifesciences, Uppsala, Sweden). As a control, ethanolamine was immobilized on the reference channel. Three different chips were used and immobilization levels for Aβ were comparable (21605RU, 22180RU and 21929RU, respectively). One RU represents about 1 pg/mm$^2$ of the analytes on the surface matrix of the sensor chip.

The tested compounds were dissolved in DMSO and diluted further in DMSO to give 1000× concentrated stock solutions. The stock solutions were diluted 1:1000 in HBS-EP buffer which contains 0.01M HEPES, pH7.4, 0.15M NaCl, 3 mM EDTA, and 0.005% of surfactant P20. HBS-EP+ 0.1% (v/v) DMSO was used as assay running buffer. The test solutions were injected over the sensor chip in concentrations ranging from 0.1 nM to 300 nM at a flow rate of 10 µl/min for 180 seconds at 25° C. Concentrations were tested in duplicate.

The RUs elicited by the compound injected into the ethanolamine control flow cell was set as reference response and subtracted from the RUs elicited by the same compound injected to the Aβ saturated flow cell. The relationships between each RU obtained at the steady state of binding (plateau of the binding curve) and each concentration of the compound were plotted.

After the analyte injection was stopped, HBS-EP buffer was flowed over the chip for 180 s to allow the bound analyte to dissociate from the immobilized Aβ and the dissociation curves were obtained. After the dissociation phase, regeneration solution (1M NaCl, 50 mM NaOH) was injected and flowed over the chip for 30 seconds to remove the residual bound analytes from the immobilized Aβ.

BIACORE X100 control software Ver 1.1 was used to record the binding curves and BIACORE X100 evaluation software Ver 1.1 to analyze the curves (plot each RU at the steady state vs. concentration of analyte, fit the plot, determine K$_D$ values). The dissociation equilibrium constant K$_D$ of the analyte to the immobilized Aβ was determined from the steady-state levels estimating the maximum RU R$_{max}$ and calculating the K$_D$ as the concentration of the compound that elicited one-half of the R$_{max}$.

Table 4 below presents the IC-50 values obtained by performing repeating tests for exemplary compounds as described herein.

TABLE 4
| Compound | Structure | SPR binding IC50 [nM] +/− SD (repeats) |
|---|---|---|
| EG030 | 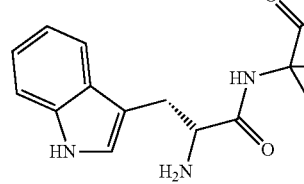 | 29.6 ± 1.7 (5) |
| D | 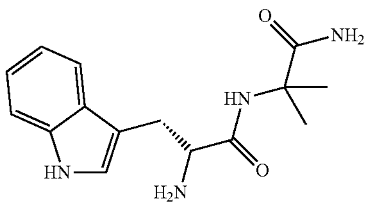 | 12.2 ± 8.5 (4) |
| E | 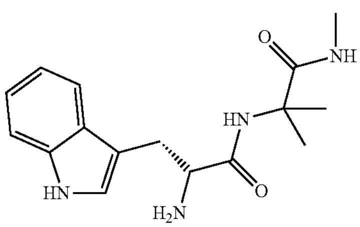 | 40.2 ± 3.4 (2) |
| F | 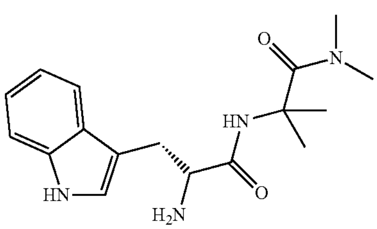 | 4.2 ± 0.0 (3) |
| A | 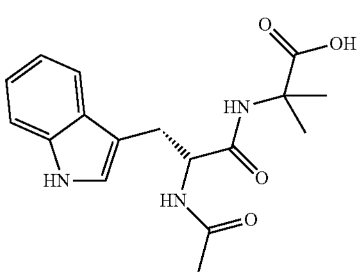 | 2.8 ± 0.8 (7) |
TABLE 4-continued
| Compound | Structure | SPR binding IC50 [nM] +/− SD (repeats) |
|---|---|---|
| C | 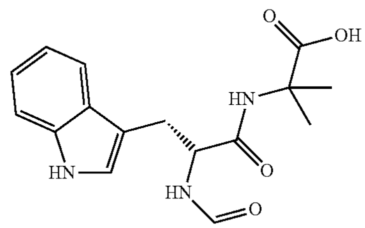 | 3.9 ± 0.1 (2) |
| B | 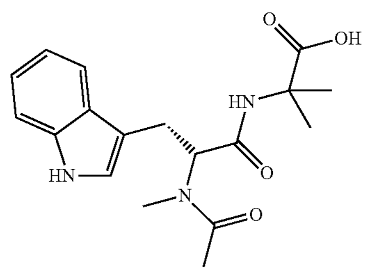 | 56.4 ± 32.7 (2) |
| U | 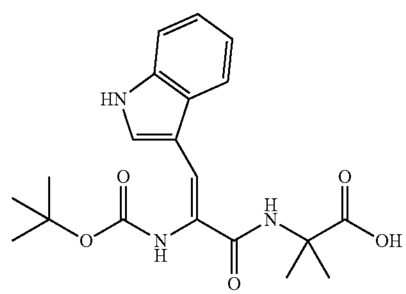 [SMILES: CC(C)(C)OC(=O)N/C(=C\c1c[nH]c2ccccc12)C(=O)NC(C)(C)C(=O)O] | 6.2 ± 1.9 (3) |
| T | 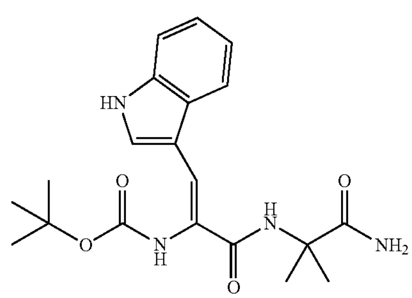 [SMILES: CC(C)(C)OC(=O)N/C(=C\c1c[nH]c2ccccc12)C(=O)NC(C)(C)C(N)=O] | 1.5 ± 0.6 (2) |

TABLE 4-continued

| Compound | Structure | SPR binding IC50 [nM] +/− SD (repeats) |
|---|---|---|
| R | (Ac-Trp-Aib-OH structure with indole) | 4.3 ± 1.0 (2) |
| Q | (Boc-Trp-Aib-OH structure with indole) | 3.8 ± 1.4 (2) |
| V | (Ac-Trp-Aib-NHMe, N-methylated structure with indole) | 0.5 ± 0 (1) |

Example 4

Pharmacological Parameters

The aqueous solubility of exemplary dipeptide analogs as disclosed herein was tested at pH 7.4. The data obtained in presented in Table 5 below, and indicate that all of the tested compounds showed good solubility above 250 μM.

Exemplary peptide analogs as disclosed herein were tested for membrane permeability in MDCKII cells transfected with human PGP, for evaluating intestinal absorption. The data obtained in presented in Table 5 below, where A-B is the apical-basolateral flux and AI is the asymmetry index.

The metabolic stability of exemplary peptide analogs as disclosed herein was tested in Human and Rat liver microsomes (HLM and RLM, respectively). The obtained data is presented in Table 5 below, as % of compound remaining after 30 minutes). All of the peptides were found sufficiently stable.

TABLE 5

| Dipeptide | ADME Solubility pH 7.4 (μM) | Permeability MDCKII/PGP [$10^{-6}$ cm/s] | | Metabolic Stability (%) | |
|---|---|---|---|---|---|
| | | A-B | AI | HLM | RLM |
| 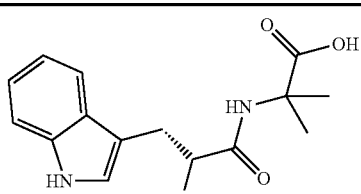 (EG030) | >350 | 1.2 | 0.7 | >100 | >100 |
| 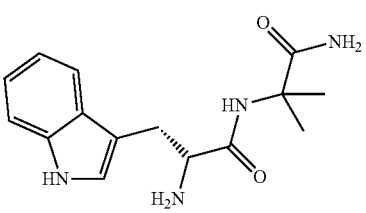 (FIG. 3; D) | >355 | 1.6 | 1.1 | >100 | >100 |

TABLE 5-continued

| Dipeptide | ADME Solubility pH 7.4 (μM) | Permeability MDCKII/PGP [10⁻⁶ cm/s] | | Metabolic Stability (%) | |
|---|---|---|---|---|---|
| | | A-B | AI | HLM | RLM |
| (FIG. 3; E) | 315 | 2.3 | 2.3 | | |
| (FIG. 3; F) | 273 | 1.5 | 4.9 | | |
| (FIG. 3; A) | 253 | 1.5 | 0.7 | 90 | >100 |
| (FIG. 3; C) | 222 | 1.3 | 0.7 | 87 | >100 |
| (FIG. 3; B) | >278 | 1.3 | 0.8 | | |

TABLE 5-continued
| Dipeptide | ADME Solubility pH 7.4 (μM) | Permeability MDCKII/PGP [$10^{-6}$ cm/s] | | Metabolic Stability (%) | |
|---|---|---|---|---|---|
| | | A-B | AI | HLM | RLM |
| 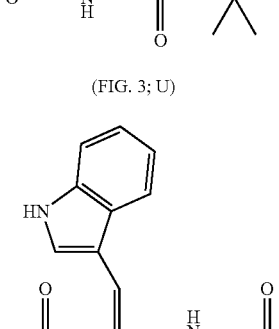 (FIG. 3; U) | >280 | 2.1 | 1.2 | 95 | 81 |
| 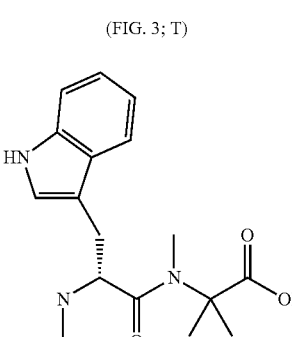 (FIG. 3; T) | >282 | 10.6 | 1.6 | | |
| 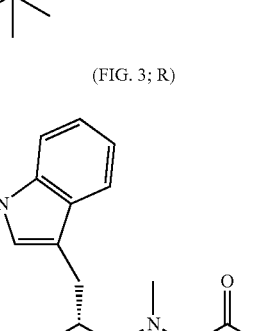 (FIG. 3; R) | 239 | 1.4 | 0.3 | 100 | 87 |
| 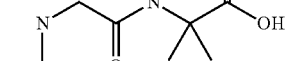 (FIG. 3; Q) | >286 | 0.7 | 1 | 88 | >100 |

| Dipeptide | ADME Solubility pH 7.4 (μM) | Permeability MDCKII/PGP [10⁻⁶ cm/s] | | Metabolic Stability (%) | |
|---|---|---|---|---|---|
| | | A-B | AI | HLM | RLM |
| (FIG. 3V) | 280 | 0.7 | 4.4 | | |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A dipeptide analog comprising a tryptophan (Trp) moiety coupled to a beta-sheet breaker moiety, with the proviso that said dipeptide analog is not a Trp-Aib dipeptide or ester thereof, wherein said beta sheet breaker moiety has a chemical structure selected from the group consisting of:

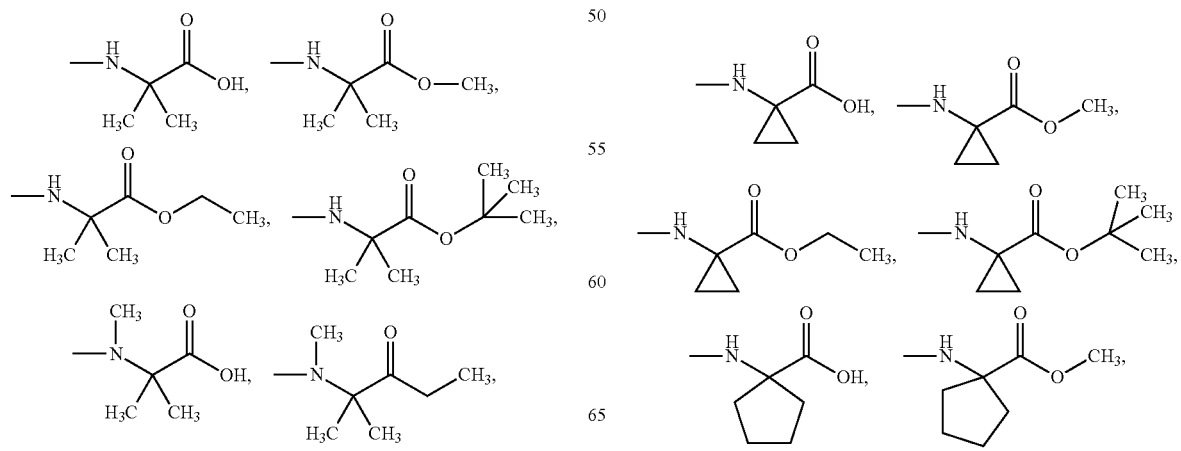

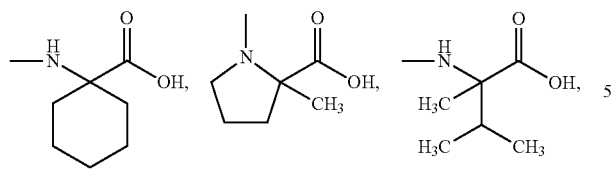
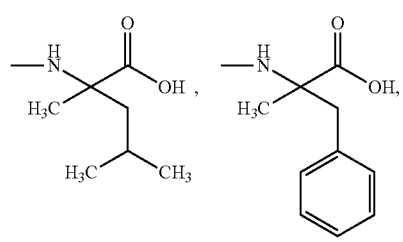
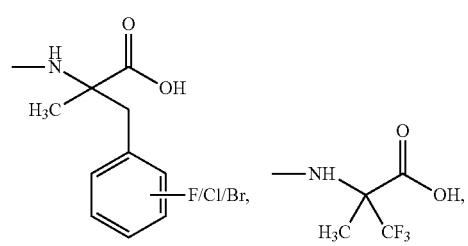
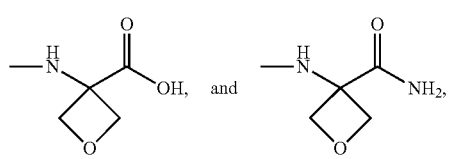
and wherein said Trp moiety has a chemical structure selected from the group consisting of:
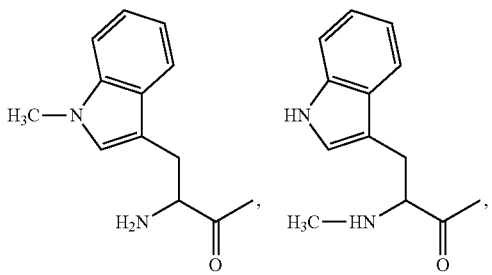
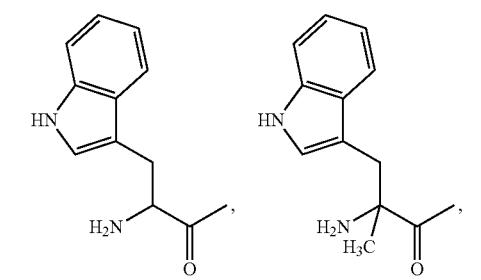
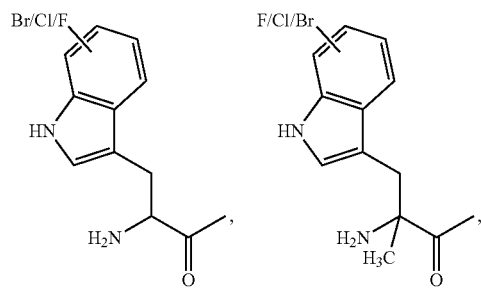
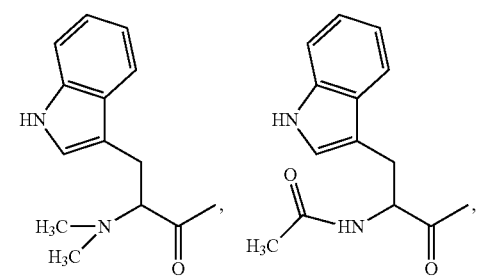
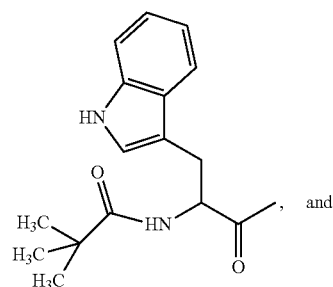
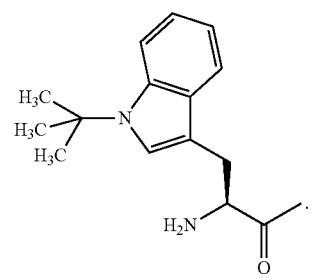
2. The dipeptide analog of claim 1, represented by a chemical structure selected from the group consisting of:
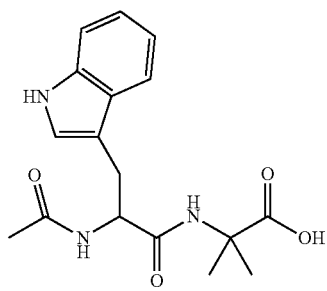

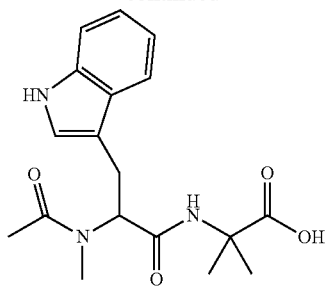
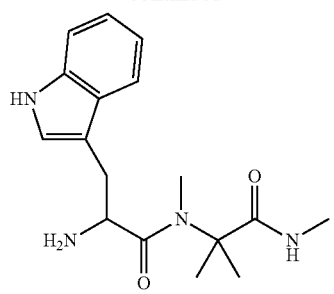
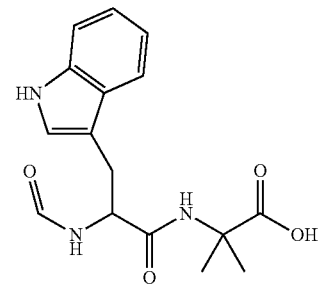
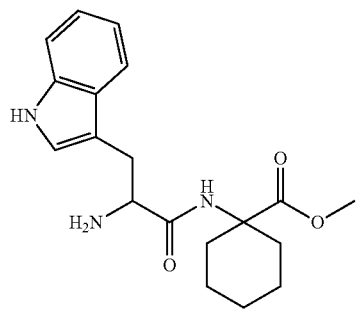
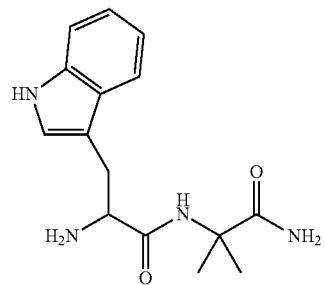
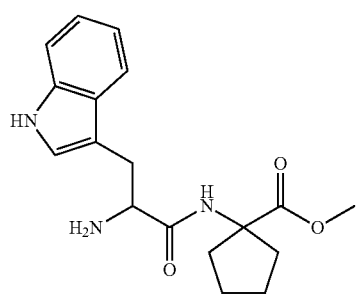
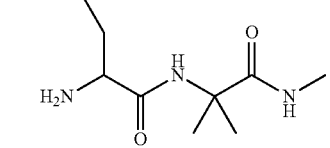
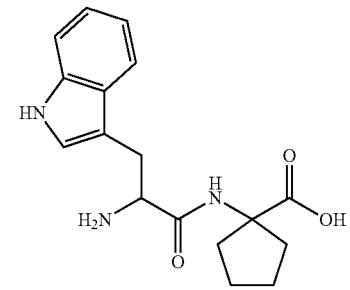
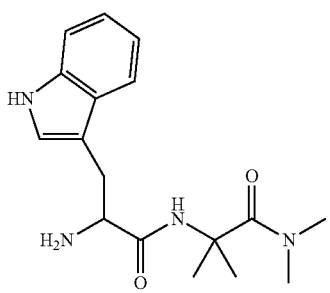
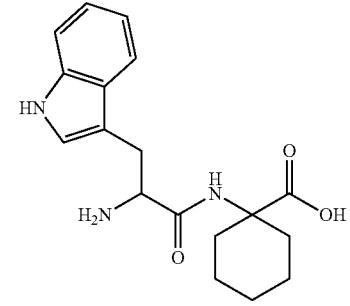

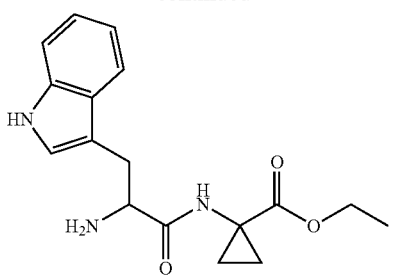
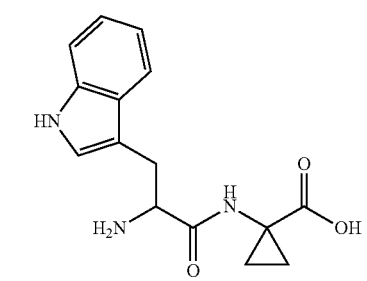
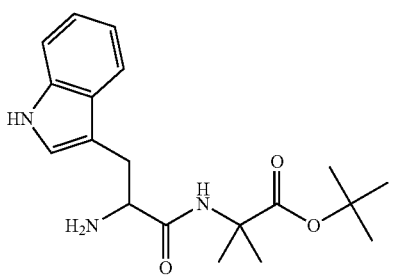
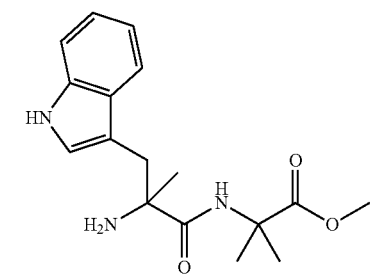
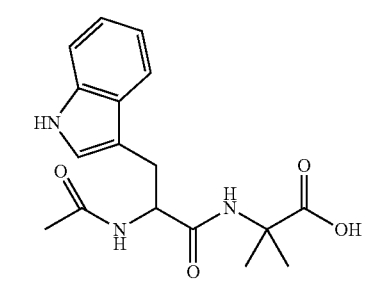
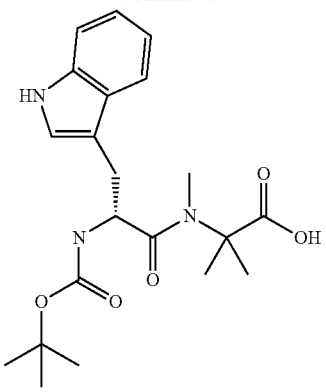 [SMILES: CN(C(=O)[C@@H](Cc1c[nH]c2ccccc12)NC(=O)OC(C)(C)C)C(C)(C)C(=O)O]
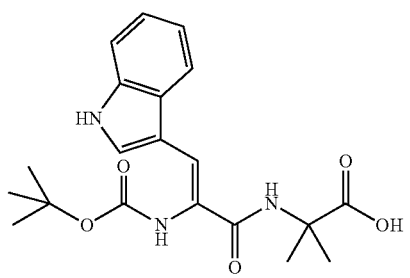
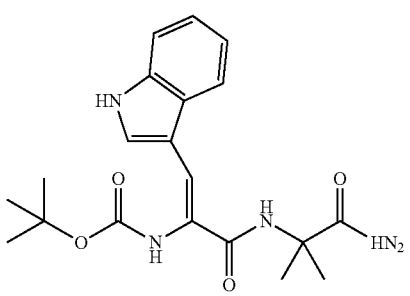 [SMILES: CC(C)(C)OC(=O)N/C(=C\c1c[nH]c2ccccc12)C(=O)NC(C)(C)C(N)=O]
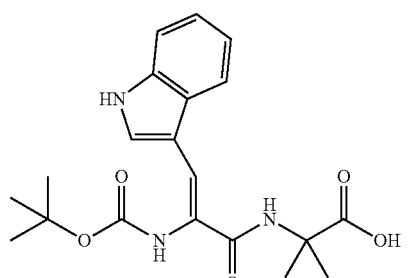
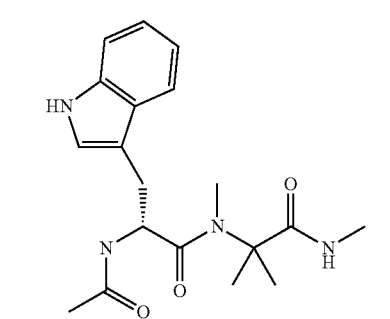 [SMILES: CNC(=O)C(C)(C)N(C)C(=O)[C@@H](Cc1c[nH]c2ccccc12)NC(C)=O]

-continued
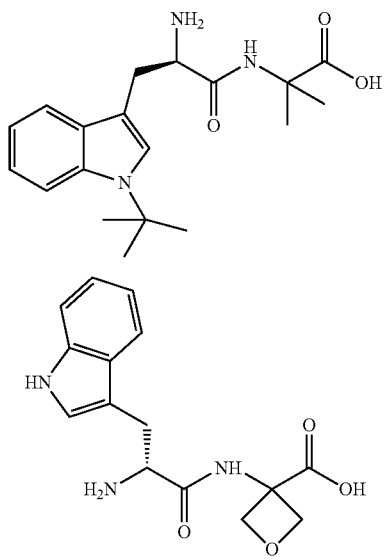
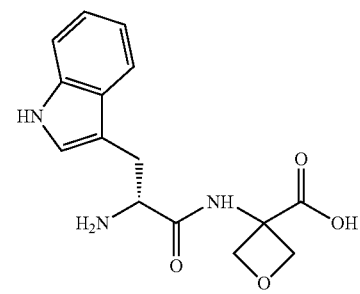
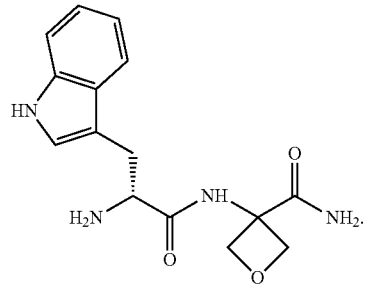
3. The dipeptide analog of claim 1, wherein said beta sheet breaker moiety has a chemical structure selected from the group consisting of:
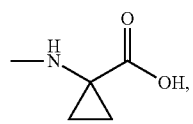 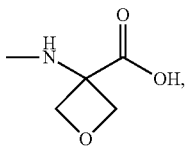
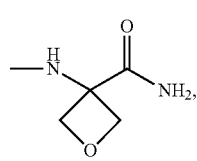 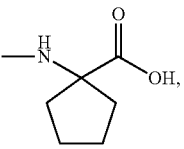
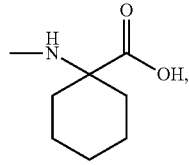 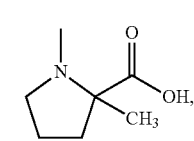
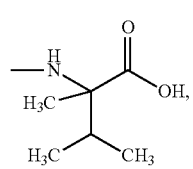 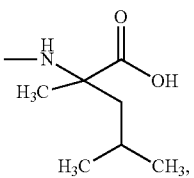
-continued
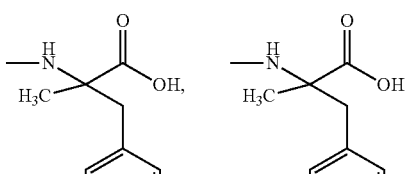
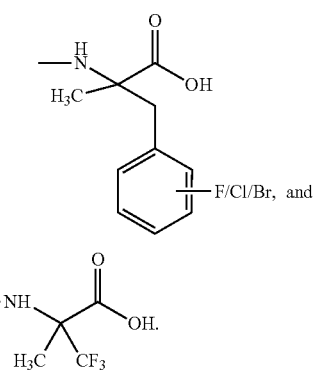
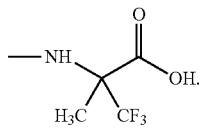
4. The dipeptide analog of claim 1, wherein said Trp moiety has a chemical structure selected from the group consisting of:
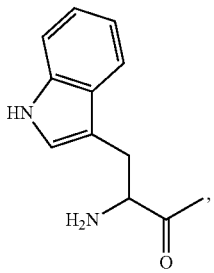 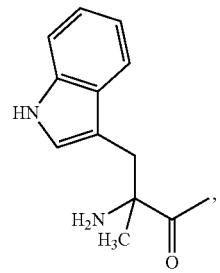
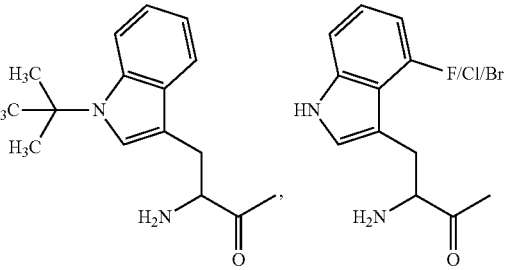
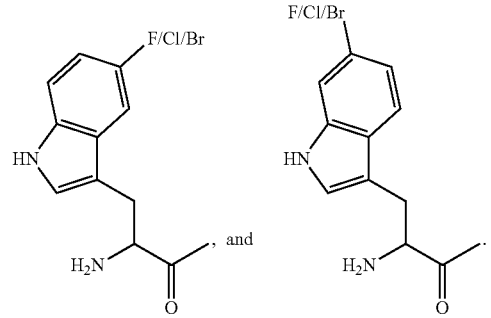

5. The dipeptide analog of claim 3, wherein said Trp moiety has a chemical structure selected from the group consisting of:

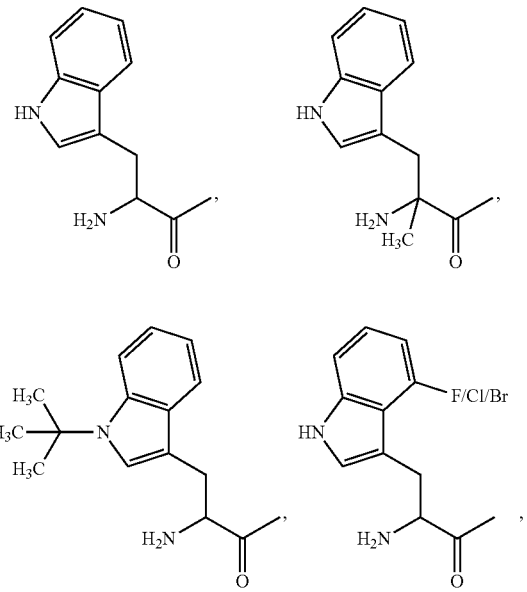

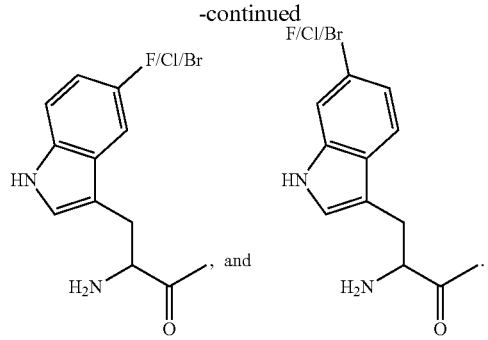

6. A pharmaceutical composition comprising the peptide analog of claim 1 and a pharmaceutically acceptable carrier.

7. The pharmaceutical composition of claim 6, being packaged in a packaging material and identified in print, in or on said packaging material, for use in the treatment of an amyloid-associated disease or disorder.

8. A method of inhibiting amyloid fibril formation in a subject in need thereof, the method comprising administering to the subject a therapeutically effective amount of the dipeptide analog of claim 1.

9. A process of preparing the dipeptide analog of claim 1, the process comprising coupling said tryptophane moiety and said beta-sheet breaker moiety, thereby preparing the dipeptide analog.

* * * * *